US006383733B1

(12) United States Patent
Beug et al.

(10) Patent No.: US 6,383,733 B1
(45) Date of Patent: *May 7, 2002

(54) METHODS OF SCREENING FOR PHARMACOLOGICALLY ACTIVE COMPOUNDS FOR THE TREATMENT OF TUMOUR DISEASES

(75) Inventors: Hartmut Beug; Martin Oft, both of Vienna (AT); Ernst Reichmann, Epalinges (CH); Karl-Heinz Heider, Stockerau (AT)

(73) Assignee: Boehringer Ingelheim International GmbH, Ingelheim am Rhein (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,716

(22) PCT Filed: Apr. 4, 1997

(86) PCT No.: PCT/EP97/01699

§ 371 Date: Feb. 16, 1999

§ 102(e) Date: Feb. 16, 1999

(87) PCT Pub. No.: WO97/37678

PCT Pub. Date: Oct. 16, 1997

(30) Foreign Application Priority Data

Apr. 5, 1996 (DE) ......................................... 196 13 691

(51) Int. Cl.$^7$ ........................ C12Q 1/00; G01N 33/53; G01N 33/567; C12N 15/00; C12N 15/09

(52) U.S. Cl. ............................. 435/4; 435/7.1; 435/7.2; 435/7.21; 435/320.1; 435/325; 436/63; 436/64

(58) Field of Search ............................. 435/4, 7.1, 7.2, 435/7.21, 325, 320.1; 436/63, 64

(56) References Cited

FOREIGN PATENT DOCUMENTS

| EP | 604181 | 6/1994 |
|---|---|---|
| WO | WO 91/19513 | 12/1991 |
| WO | WO 94/25588 | 11/1994 |
| WO | WO 95/19987 | 7/1995 |
| WO | WO 96/07657 | 3/1996 |

OTHER PUBLICATIONS

Braunwalder, A.F. et al., "Measurement of the Protein Tyrosine Kinase Activity of c–src Using Time–Resolved Fluorometry of Europium Chelates," *Analytical Biochem.* 238:159–164 (1996).
Buchmann, A. et al., "Progression of Squamous Carcinoma Cells to Spindle Carcinomas of Mouse Skin Is Associated with an Imbalance of H–ras Alleles on Chromosome 7," *Cancer Res.* 51:4097–4101 (1991).

Castle, V. et al., "Antisense–mediated Reduction in Thrombospondin Reverses the Malignant Phenotype of a Human Squamous Carcinoma," *J. Clin. Invest.* 87:1883–1888 (1991).
Wrana, J. L. et al., "Mechanism of activation of the TGF–β receptor," *Nature* 370:341–347 (1994).
Zambruno, G. et al., "Transforming Growth Factor–β1 Modulates β1 and β5 Integrin Receptors and Induces the de novo Expression of the αvβ6 Heterodimer in Normal Human Keratinocytes: Implications for Wound Healing," *J. Cell Biol.* 129: 853–865 (1995).
International Search Report for International Application No. PCT/EP97/01699, mailed Jul. 18, 1997.
Whitman M. and Melton, D.A., "Involvement of p21$^{ras}$ in Xenopus mesoderm induction," *Nature* 357:252–254 (1992).
Wong, S.Y. et al., "Thrombospondin and Other Possible Related Matrix Proteins in Malignant and Benign Breast Disease. An Immunohistochemical Study," *Amer. J. Pathol.* 140:1473–1482 (1992).
Wrana, J.L. et al., "TGFβ Signals through a Heteromeric Protein Kinase Receptor Complex," *Cell* 71:1003–1014 (1992).
Vogelstein, B, and Kinzler, K.W., "The multistep nature of cancer," *Trends in Genetics* 9:138–141 (1993).
Wargotz, E.S. and Norris, H.J., "Metaplastic Carcinomas of the Breast. III. Carcinosarcoma," *Cancer* 64:1490–1499 (1989).
Welch, D.R. et al., "Transforming growth factor β stimulates mammary adenocarcinoma cell invasion and metastatic potential," *Proc. Natl. Acad. Sci. USA* 87:7678–7682 (1990).
Thompson, T.C. et al., "Transforming Growth Factor β1 as a Biomaker for Prostate Cancer," *J. Cell. Biochem.* 16H (Suppl.):54–61 (1992).
Thompson, T.C. et al., "Transgenic Models for the Study of Prostate Cancer," *Cancer* 71 (Suppl.):1165–1171 (1993).
Thorburn, A. et al., "HRas–dependent Pathways Can Activate Morphological and Genetic Markers of Cardiac Muscle Cell Hypertrophy," *J. Biol. Chem.* 268:2244–2249 (1993).
Stacey, D.W. et al., "Dominant Inhibitory Ras Mutants Selectively Inhibit the Activity of either Cellular or Oncogenic Ras," *Mol. Cell. Biol.* 11:4053–4064 (1991).

(List continued on next page.)

Primary Examiner—Anthony C. Caputa
Assistant Examiner—Alana M. Harris
(74) Attorney, Agent, or Firm—Sterne, Kessler, Goldstein & Fox P.L.L.C.

(57) ABSTRACT

Pharmaceutical compositions containing as active compound a substance which inhibits the activity of TGFβ on tumour cells of epithelial origin, for the treatment of epithelial, invasive tumour diseases which are characterized by a reversible transition of the cells from an epithelial, non-invasive state into a fibroblastoid, invasive state. The pharmaceutical composition contains a TGFβ inhibitor, preferably combined with an Ras inhibitor. Process for screening substances for the treatment of epithelial, invasive tumour diseases.

14 Claims, 18 Drawing Sheets

OTHER PUBLICATIONS

Stoler, A.B. et al., "The Conversion of Mouse Skin Squamous Cell Carcinomas to Spindle Cell Carinomas Is a Recessive Event," *J. Cell Biol.* 122:1103–1117 (1993).

Thompson, A.M. et al., "Transforming growth factor β1 is implicated in the failure of tamoxifen therapy in human breast cancer," *Br. J. Cancer* 63:609–614 (1991).

Schultz–Cherry, S. et al., "Thrombospondin Binds and Activates the Small and Large Forms of Latent Transforming Growth Factor–β in a Chemically Defined System," *J. Biol. Chem.* 269:26775–26782 (1994).

Slamon, D.J. et al., "Expression of Cellular Oncogenes in Human Malignancies," *Science* 224:256–262 (1984).

Sonnenberg, A. et al., "In Vitro Differentiation and Progression of Mouse Mammary Tumor Cells," *Cancer Res.* 46:5913–5922 (1986).

Sanford, K.K. et al., Sarcomatous Change and Maintenance of Differentiation in Long–Term Cultures of Mouse Mammary Carcinoma, *J. Natl. Can. Inst.* 26:1139–1183 (1961).

Sato, Y. et al., "Characterization of the Activation of Latent TGF–β by Co–cultures of Endothelial Cells and Pericytes or Smooth Muscle Cells: A Self–regulating System," *J. Cell Biol.* 111:757–763 (1990).

Schoenenberger, C.–A. et al., "Integrin expression and localization in normal MDCK cells and transformed MDCK cells lacking apical polarity," *J. Cell Sci.* 107:527–541 (1994).

Payne, P.A. et al., "An activated c–Ha–ras allele blocks the induction of muscle–specific genes .whose expression is contingent on mitogen withdrawal," *Proc. Natl. Acad. Sci. USA* 84:8956–8960 (1987).

Quilliam, L.A. et al., "Identification of Residues Critical for Ras(17N) Growth–Inhibitory Phenotype and for Ras Interaction with Guanine Nucleotide Exchange Factors," *Mol. Cell. Biol.* 14:1113–1121 (1994).

Roberts, A.B. and Sporn, M.B., "Mechanistic Interrelationships between Two Superfamilies: The Steroid/Retinoid Receptors and Transforming Growth Factor–β," *Cancer Surveys* 14:205–220 (1992).

Nishihara, K. and Tsuneyoshi, M., "Undifferentiated Spindle Cell Carcinoma of the Gallbladder: A Clinicopathologic, Immunohistochemical, and Flow Cytometric Study of 11 Cases," *Hum. Pathol.* 24:1298–1305 (1993).

Oft, M. et al., "TGF–β1 and Ha–Ras collaborate in modulating the phenotypic plasticity and invasiveness of epithelial tumor cells," *Genes & Develop.* 10:2462–2477 (Oct. 1996).

Parker, T.G. et al., "Peptide Growth Factors Can Provoke 'Fetal' Contractile Protein Gene Expression in Rat Cardiac Myocytes," *J. Clin. Invest.* 85:507–514 (1990).

Miettinen, P.J. et al., "TGF–β Induced Transdifferentiation of Mammary Epithelial Cells to Mesenchymal Cells: Involvement of Type I Receptors," *J. Cell Biol.* 127:2021–2036 (1994).

Monia, B.P. et al., "Sequence–specific antitumor activity of a phosphorothioate oligodeoxyribonucleotide targeted to human C–raf kinase supports an antisense mechanism of action in vivo," *Proc. Natl. Acad. Sci. USA* 93:15481–15484 (Dec. 1996).

Murthy, U. et al., "Expression of TGF–α/EGF and TGF–β Receptors in Human Colon Carcinoma Cell Lines," *Int. J. Cancer* 44:110–115 (1989).

LeJeune S. et al., "Amphiregulin, Epidermal Growth Factor Receptor, and Estrogen Receptor Expression in Human Primary Breast Cancer," *Cancer Res.* 53:3597–3602 (1993).

Lin, H.Y. et al., "Expression Cloning of the TGF–β Type II Receptor, a Functional Transmembrane Serine/Threonine Kinase," *Cell* 68:775–785 (1992); erratum, *Cell* 70:1068 (1992).

Matsui, K. et al., "Lung Carcinoma With Spindle Cell Components: Sixteen Cases Examined by Immunohistochemistry," *Hum. Pathol.* 23:1289–1297 (1992).

Kohl, N.E. et al., "Selective Inhibition of ras–Dependent Transformation by a Farnesyltransferase Inhibitor," *Science* 260:1934–1937 (1993).

Kohl, N.E. et al., "Protein farnesyltransferase inhibitors block the growth of ras–dependent tumors in nude mice," *Proc. Natl. Acad. Sci. USA* 91:9141–9145 (1994).

Kohl, N.E. et al., "Inhibition of farnesyltransferase induces regression of mammary and salivary carcinomas in ras transgenic mice," *Nature Med.* 1:792–797 (Aug. 1995).

Kern, F.G. et al., "Growth factor receptors and the progression of breast cancer," *Semin. Cancer Biol.* 1:317–328 (1990).

Keski–Oja, J. et al., "Transforming Growth Factors and Control of Neoplastic Cell Growth," *J. Cell. Biochem.* 33:95–107 (1987).

Kim, S.–J. et al., "Promotor Sequences of the Human Transforming Growth Factor–β1 Gene Responsive to Transforming Growth Factor–β1 Autoinduction," *J. Biol. Chem.* 264:7041–7045 (1989).

Heatley, M. et al., "Vimentin expression in benign and malignant breast epithelium," *J. Clin. Pathol.* 46:441–445 (1993).

Hoosein, N.M. et al., "Differential Sensitivity of Subclasses of Human Colon Carcinoma Cell Lines to the Growth Inhibitory Effects of Transforming Growth Factor–β1," *Exper. Cell Res.* 181:442–453 (1989).

Jenkins, D.C. et al., "A novel cell–based assay for the evaluation of anti–ras compounds," *Br. J. Cancer* 68:856–861 (1993).

Guarino, M. et al., "Carcinosarcoma of the oesophagus with rhabdomyoblastic differentiation," *Histopathol.* 22:493–498 (1993).

Hand, P. H. et al., "Monoclonal antibodies of predefined specificity detect activated ras gene expression in human mammary and colon carcinomas," *Proc. Natl. Acad. Sci. USA* 81:5227–5231 (1984).

Hay, E.D., "An Overview of Epithelio–Mesenchymal Transformation," *Acta Anat.* 154:8–20 (1995).

Eaton, S., and Simons, K., "Apical, Basal, and Lateral Cues for Epithelial Polarization," *Cell* 82:5–8 (1995).

Fakhrai, H. et al., "Eradication of established intracranial rat gliomas by transforming growth factor β antisense gene therapy," *Proc. Natl. Acad. Sci. USA* 93:2909–2914 (1996).

Furth, M.E. et al., "Monoclonal Antobodies to the p21 Products of the Transforming Gene of Harvey Murine Sarcoma Virus and of the Cellular ras Gene Family," *J. Virology.* 43:294–304 (1982).

Caulin, C. et al., "Chronic Exposure of Cultured Transformed Mouse Epidermal Cells to Transforming Growth Factor–$β_1$ Induces an Epithelial–Mesenchymal Transdifferentiation and a Spindle Tumoral Phenotype," *Cell Growth & Differen.* 6:1027–1035 (1995).

DeBortoli, M.E. et al., "Amplified Expression of p21 ras Protein in Hormone–Dependent Mammary Carcinomas of Humans and Rodents," *Biochem. and Biophys. Res. Comm.* 127:699–706 (1985).

de Brito, P.A., et al., "Carcinosarcoma (Malignant Mixed Müllerian (Mesodermal) Tumor) of the Female Genital Tract: Immunohistochemical and Ultrastructural Analysis of 28 Cases," *Hum. Pathol.* 24:132–142 (1993).

Andrejauskas, E. and Moroni, C., "Reversible abrogation of IL–3 dependence by an inducible H–ras oncogene," *Embo J.* 8:2575–2581 (1989).

Antonelli–Orlidge, A. et al., "An activated form of transforming growth factor β is produced by cocultures of endothelial cells and pericytes," *Proc. Natl. Acad. Sci. USA* 86:4544–4548 (1989).

Beham, A. et al., "Distribution of cytokeratins, vimentin and desmoplakins in normal renal tissue, renal cell carcinomas and oncocytoma as revealed by immunoflurescence microscopy," *Virchows Archiv. A. Pathol. Anat.* 421:209–215 (1992).

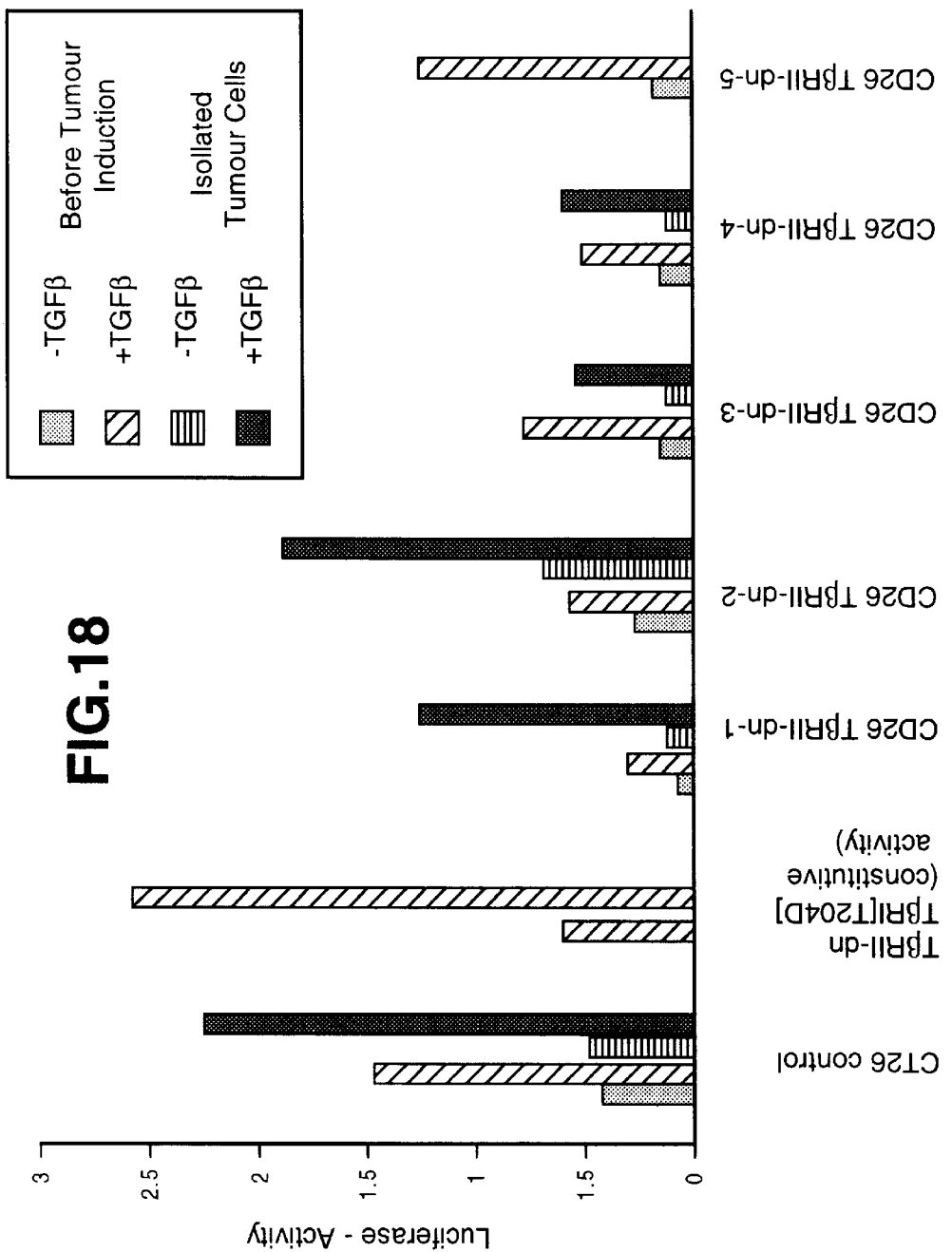

METHODS OF SCREENING FOR PHARMACOLOGICALLY ACTIVE COMPOUNDS FOR THE TREATMENT OF TUMOUR DISEASES

FIELD OF THE INVENTION

The invention relates to the field of tumour therapy.

BACKGROUND OF THE INVENTION

More than 80% of tumours occurring in man are of epithelial origin. The formation of epithelial tumours (carcinomas) is a multi-stage process which is illustrated most clearly in the progression of human colon carcinoma (Powell, et al., 1993) and skin tumours in mice (Wright, et al., 1994). Carcinomas are assumed to start from individual cells or small groups of cells in which mutations have occurred. These cells develop into benign, epithelial hyper- or dysplastic regions. The progression of these hyperplastic regions into a carcinoma in situ, which may then acquire invasive and metastatic properties, requires a number of further mutations in the tumour cell. Characteristically these cells acquire the ability to break down their basal membrane proteolytically, to develop from a stationary polarised cell into a non-polarised cell capable of migrating in the tissue, to survive in the bloodstream and form metastases at remote sites (Liotta, et al., 1991; Liotta and Stetler-Stevenson, 1991).

Although deep changes in gene expression are involved in the many changes in the architecture and behaviour of malignantly transformed cells, none of these newly acquired properties occurs only in invasive tumour cells. Attachment to the basal membrane, proteolysis thereof and migration through the basal membrane and the underlying mesenchyme are important stages in normal processes, e.g. in the implantation of the trophoblast, in movements of configuration during development of the embryo, in the development of the mammary gland and the reorganisation of epithelia during wound healing (Aznavoorian et al., 1993).

For a better understanding of the development and progression of carcinomas it is crucial to understand how the deregulation of these normal processes takes place in cell invasion and metastasisation.

Studies in recent years have contributed to an understanding of the molecular mechanisms involved in the modulation of the epithelial phenotype in normal and pathological situations (Reichmann, et al., 1992; Frisch, 1994). Moreover, exogenous polypeptide factors such as Scatter Factor (SF)/Hepatocyte growth factor (HGF) and New-Regulin/HER-Regulin play important roles in the changes in the migration and differentiation properties of epithelial cells (Birchmeier et al., 1993; Hartmann et al., 1994; Soriano et al., 1995). only recently, Transforming Growth Factor 1 (TGFβ1) was identified as another potent modulator of the phenotype of breast epithelial cells (Miettinen et al., 1994; Zambruno et al., 1995).

TGFβ1 belongs to a large super-family of multifunctional polypeptide factors. The TGFβ family itself consists of three genes, TGFβ1, TGFβ2 and TGFβ3, which have extremely high homology with one another. In mammals the TGFβ-super-family also includes the various TGFβ genes as well as the embryonic morphogenes, such as e.g. the family of the activins, "Müllerian Inhibitory Substance", and the bmp family ("Bone Morphogenetic Protein"), which play important roles both in regulating embryo development and in the reorganisation of epithelia (Roberts and Sporn, 1992). TGFβ1 inhibits the growth of many cell types, including epithelial cells, but stimulates the proliferation of various types of mesenchymal cells. In addition, TGFβs induce the synthesis of extracellular matrix proteins, modulate the expression of matrix proteinases and proteinase inhibitors and change the expression of integrins. Moreover, TGFβs are expressed in large amounts in many tumours (Derynck et al., 1985; Keski-Oja et al., 1987). This strong occurrence in neoplastic tissues could indicate that TGFβs are strategic growth/morphogenesis factors which influence the malignant properties associated with the various stages of the metastatic cascade. TGFβs inhibit the growth of normal epithelial and relatively differentiated carcinoma cells, whereas undifferentiated tumour cells which lack many epithelial properties are generally resistant to growth inhibition by TGFβs (Hoosein et al., 1989; Murthy et al., 1989). Furthermore TGFβ1 may potentiate the invasive and metastatic potential of a breast adenoma cell line (Welch et al., 1990), which indicates the role of TGFβ1 in the tumour progression. The molecular mechanisms underlying the effect of TGFβs during the tumour cell invasion and metastasisation do, however, require further explanation.

The formation of breast cancer (mammary carcinoma) in humans involves the overexpression of (mutated or, more often, non-mutated) ras-genes and the overexpression of receptor-tyrosinekinases, which activate the Ras-signal transmission pathway (De Bortoli et al., 1985; Kern et al., 1990; LeJeune et al., 1993).

SUMMARY OF THE INVENTION

The aim of the present invention was to provide new pharmaceutical compositions for tumour therapy.

The solution to the problem started from the following findings obtained from the tests carried out:

1. The activity of TGFβ on the tumour cell, in cooperation with (i) the expression of oncogenic Ras, with (ii) the overexpression of normal Ras or of receptor tyrosinekinases which activate the Ras signal transmission pathway or with (iii) other oncogenes activated in the tumour cell, lead to a conversion of epithelial cells into fibroblastoid cells with invasive potential.

2. The autocrine production of TGFβ by the converted cells leads to the maintenance of the degenerate, invasive cell status.

3. Interruption of the transmission mediated by the TGFβ-receptor signal prevents "epithelial-fibroblastoid conversion" (EFC) and the concomitant invasiveness and may change cells which have already undergone an EFC and are growing in a stably invasive manner back into epitheloid cells which are no longer growing invasively (fibroblastoid-epithelial conversion; FEC).

Within the scope of the present invention, the role of TGFβ1 in the normal development of the mammary glands was investigated with a view to assessing possible side effects of TGFβ1 inhibitors.

Within the scope of the present invention, it was shown, on the one hand, that Ha-Ras-transformed breast epithelial cells (EpRas-cells) undergo a transition (conversion) from the epithelial to the fibroblastoid (or mesenchymal) state in the formation of tumours in mice. This transition is hereinafter referred to as EF-transition or EF-conversion ("Epithelial-Fibroblastoid Cell Conversion", EFC). Such an EF-conversion has also been demonstrated in vitro. For this, EpRas cells were cultivated in type I collagen gels. In the absence of serum these cells developed into three-dimensional, cystic hollow structures, the walls of which consisted of a single-thickness layer (monolayer) of polarised epithelial cells. TGFβ1 caused these same Ras-transformed cells to develop into disorganised strands consisting of spindle-shaped cells with fibroblastoid properties. In non-transformed epithelian cells TGFβ1 was unable to cause such changes. The converted cells were highly invasive both in collagen gels and in chicken heart invasion assays. Surprisingly it was found that, once the fibroblastoid cells had undergone the conversion, they themselves produced large amounts of TGFβ1. If this self-produced TGFβ1 was inactivated by a TGFβ1 neutralising antibody, the cells changed back into a polarised, epithelial phenotype. This cell behaviour indicates that the converted fibroblastoid phenotype is maintained by TGFβ1, the TGFβ1 acting through an autocrine loop.

It was also shown, within the scope of the present invention, that the mechanism observed in vitro also applies in vivo: tumour cells which had undergone an EF-conversion themselves produced TGFβ1. Moreover, TGFβ1 is capable of triggering and sustaining the invasive phenotype of Ha-Ras-transformed breast epithelial cells in experimentally induced tumours.

Moreover, it was shown within the scope of the present invention that in human tumours of various origins (kidney cell carcinoma, breast cancer) there were indications of the occurrence of "Epithelial-Fibroblastoid Cell Conversion" (EFC) (75% of the kidney cell carcinomas investigated and 25–60% of the breast tumours coexpressed the general epithelial marker cytokeratin and the mesenchymal marker vimentin). It was also shown that all these tumours themselves produce TGFβ1. This is an indication that the results obtained with the model system used in the present invention also apply to human tumours.

Fourthly, it has been shown within the scope of the present invention that total inhibition of the signal transmission induced by the TGFβ receptor can be achieved using a dominant-negative TGFβ-receptor chain II (TβRII-dn). Such expression of TβRII-dn led to the elimination of the malignant, invasive phenotype, not only in Ras-transformed mouse-breast epithelial cells, but also in a number of already mesenchymal, invasively growing carcinoma cell lines in humans and mice and to the complete inhibition of the formation of tumours or metastases obtained by these lines in the experimental animals.

DETAILED DESCRIPTION OF THE INVENTION

The present invention is thus based on the following findings:

Numerous mutations in protooncogenes and tumour suppressor genes participate in carcinogenesis (Vogelstein and Kinzler, 1993). However, little is known about how specific oncogenic mutations are connected with defined changes in the phenotype of the cell and the manner in which these changes then contribute to tumour cell invasion and metastasisation. Within the scope of the present invention it was first demonstrated, using a model system, that the Ras-oncoprotein dramatically changes the cell reaction of breast epithelial cells to TGFβ1 both in collagen gels and in developing tumours. This modified reactivity of the cells causes TGFβ1 to induce an EFC. Once converted, these fibroblastoid cells themselves produced high concentrations of TGFβ1 and thus retained their own mesenchymal and invasive properties.

The theoretical validity of this principle could then be demonstrated in a number of unrelated tumour models in humans and mice. In these tumour cells, other oncogenes very probably take on the function of Ha-Ras. It has been shown that in all these cells both TGFβ1 and the interruption of any existing autocrine stimulation by TGFβ1 dramatically influences the tumour cell phenotype: TGFβ also leads to an increase in invasive growth in these cells, whereas switching off the TGFβ-receptor or the signal transmission pathways activated by it led to reformation of the EFC, i.e. to a fibroblastoid-epithelial conversion (FEC) and/or to loss of the invasive, tumour-producing cell phenotype.

The experiments carried out within the scope of the present invention originally started from the observation that Ras-transformed mouse breast epithelial cells convert into invasive spindle cells during tumour formation. Similar spindle cell tumours have been described in the brain, skin, colon and breast, both in humans and in animal models (Buchmann et al., 1991; Guldberg, 1923; Sandford et al., 1961; Sonnenberg et al. 1986; Stoler et al. 1993). The origin of these spindle cell carcinomas is still unclear, although some researchers believe that these often highly invasive tumours constitute a separate class of tumour of fibroblastoid origin, whilst other authors assume that these tumours are of epithelial origin.

In the model system used within the scope of the present invention the spindle cell tumours first used clearly originated from the epithelial donor-cells injected into the animal. Spindle cells originating from the tumour survived the selection in G418 and expressed cell- and tissue-specific cytokeratins, confirming their donor cell status and their epithelial origin. Moreover, the tests carried out showed that the injected epithelial cells and the converted fibroblastoid tumour cells came from the same cell clone and re-integration of the retroviral vector into other sites of the genome could be ruled out as a possible cause of the changes. What was almost more important was that the fibroblastoid phenotype of the converted cells was absolutely stable under standard culture conditions and that the cells changed back to polarised epithelial cells efficiently after neutralisation of the TGFβ1 activity. This rules out genetic or epigenetic changes being responsible for the cell conversion. The most probable explanation for the dramatic change in the phenotype in vivo is that an interaction between the Ras-transformed cells and mesenchymal cells surrounding them leads to the conversion of the epithelial cells into fibroblastoid cells. Within the scope of the present invention it has thus been shown that EFC is a mechanism which is relevant to carcinogenesis in certain tumours.

Within the scope of the present invention it has also been shown that TGFβ1 induces EFC both in collagen gels and during tumour development. In the cell model used first, this TGFβ1-induced conversion remarkably requires the cooperation of an activated Ras protein; neither primary breast epithelial cells nor the parental EpH4 cells underwent TGFβ1-induced EFC. From this it can be concluded that EFC is triggered by a synergy of various signal transmission pathways which are activated on the one hand by TGFβ1 and on the other hand by Ha-Ras. This assumption is supported by other findings which indicate that activated Ras proteins have similar effects on cells to members of the TGFβ family. This applies e.g. to myogenic differentiation (Payne et al., 1987) and to the formation of the mesoderm (Whitman and Melton, 1992). In the heart muscle, TGFβ highly regulates genes associated with the growth of the embryonic heart regulated by haemodynamic loading. These effects are at least partly mimicked by activated Ras (Parker et al., 1990; Thorburn et al., 1993), leading one to suppose that Ras and TGFβ can act synergistically, at least in some biological systems.

In connection with this it is interesting that the overexpression of normal and mutated Ras was observed in a considerable number of human carcinomas, including breast cancers (De Bortoli et al., 1985; Hand et al., 1984; Slamon et al., 1984). Furthermore, autocrine production of ligands as well as overexpression and/or constitutional activation of receptor-tyrosinekinases which occur at the start of signal transmission pathways including c-Ras (e.g. HER-1, HER-2), are frequent changes in breast cancers (Kern et al., 1990; LeJeune et al., 1993). Since TGFβ1 is also abundantly present in many human tumours (Derynck et al., 1985; Keski-Oja et al., 1987; Thompson et al., 1991) it may be concluded, on the basis of the results obtained within the scope of the present invention, that Ras- and TGFβ1-induced signals also act synergistically in human tumours. As demonstrated by the results of the experiments carried out within the scope of the present invention, the TGFβ-receptor may also control EFC and invasiveness in tumour cells transformed by oncogenes other than Ras. Another major finding within the scope of the present invention is thus that TGFβ cooperates with various oncoproteins, including Ras, and tyrosinekinases, in regulating the plasticity of the polarised epithelial phenotype.

After serum-free (and TGFβ-free) cell culture in reconstituted collagen gels, EpRas-cells exhibited a great capacity for organogenesis and a high degree of epithelial polarisation. The Ep-Ras cells, however, predominantly formed widened tubuli as well as alveolar cavities, in contrast to the narrow branching tubuli formed by the parental EpH4-cells or by primary breast epithelial cells. This shows that the Ras-oncoprotein on its own, in the absence of TGFβ, is capable of modifying the morphogenetic behaviour of epithelial cells to some extent. In other systems activated Ras has been described as having more powerful effects on epithelial polarity (Eaton and Simons, 1995). Here, transformation with Ras led to disruption of the polar expression of apical proteins, whilst the expression of basolateral marker proteins remained unaffected (Schoenenberger et al., 1994). Since the experiments described above were carried out in the presence of FCS (which itself contains TGFβ1), however, it is difficult to compare them with the results obtained within the scope of the present invention in which no such obvious polarity defects could be observed. Since exogenous TGFβ1 completely destroyed the cell polarity, it is possible that the partial destruction of the polarity in the abovementioned Ras-transformed cell systems can be put down to the TGFβ1-concentrations present in the serum. Nonetheless the morphogenetic behaviour in EpRas-cells is changed slightly, possibly as the result of increased protease activity.

TGFβ completely destroyed the polarity of epithelial cells and caused the cells to become spindle-shaped and invasive. These changes were dependent on the constant presence of TGFβ1, since the spindle cells quickly changed back into polarised epithelial cells when TGFβ1 neutralising antibodies were added. The most important conclusion from these results is that Ras-transformed cells can be switched back and forth by TGFβ1 between a quasi-normal and a highly tumorigenic phenotype. This intense phenotypical plasticity might be characteristic of invasively growing cells in general and might explain why invasive tumour cells often exhibit the migratory properties of fibroblasts. After extravasation these fibroblastoid, migratory cells should be able to develop back into well differentiated secondary tumours in the new environment provided by remotely located tissue (see below). Increased phenotypical plasticity is thus a characteristic of invasive tumour cells.

Another essential finding reached within the scope of the present invention is that EpRas cells have to undergo EFC in order to produce significant amounts of TGFβ1 both in vitro and in vivo. It has been shown that tumour cells are able to maintain their fibroblastoid phenotype by means of the autocrine production of TGFβ1 and that the autocrine TGFβ1 production and effect on the producing cell (autocrine loop) has to be interrupted in order to make the phenotypical re-conversion of the cells possible. The ability of TGFβ1 to induce EFC and then efficiently maintain the invasive phenotype may also explain why the initially epithelial Ras-transformed cells changed progressively and uniformly into spindle cells during the tumour growth.

Shortly after their injection into mice, polarised Ras-transformed epithelial cells neither expressed nor released significant quantities of TGFβ1. As was established by hybridisation in situ and immunohistochemistry, however, the stroma cells surrounding the microtumour expressed the cytokine. These stroma cells could be identified as fibrocyte and endothelial cells, but it must be presumed that other cell types, such as macrophages and lymphocytes, were probably also present; all these cell types are known to produce and release TGFβ1. The most probable conclusion is that the effects of TGFβ1 are regulated primarily at the level of their proteolytic activation. The primary regulation of TGFβ is carried out by factors which control the processing of the latent into the biologically active molecule. However, virtually nothing is known about the TGFβ activation in vivo. The protease plasmin can activate two cell types of latent TGFβ1 in co-culture systems, but only if two different cell types are in direct contact or close together (Antonelli-Orlidge et al., 1989; Sato et al., 1990). This close contact of different cell types should take place in the system used within the scope of the present invention after encapsulation of the tumours by the stroma and to an even greater extent if donor-tumour cells are mixed with stroma cells of the receiver animal during the tumour development (FIG. 2B). Furthermore, thrombospondin (TSP), an extracellular matrix protein, activates latent TGFβ. In this case the activation takes place in the soluble phase and requires no proteolytic activity (Schultz-Cherry et al., 1994). In fact, the role of thrombospondin in supporting the development of cancer and the increased thrombospondin concentrations in malignant breast cancers have been briefly reported (Castle et al. 1991; Wong et al., 1992). It has thus been shown within the scope of the present invention that the autocrine production of TGFβ1, in cooperation with the oncoprotein Ha-Ras, maintains the fibroblastoid phenotype.

The findings and conclusions reached within the scope of the present invention led to the hypothetical model shown in FIG. 9. It is postulated that the TGFβ1 which is relevant to the tumour formation is produced primarily by infiltrating cells of the tumour stroma, such as fibrocytes, endothelial cells, lymphocytes and macrophages. The interaction of the tumour cells with the different cell types of the tumour stroma should trigger the efficient production and/or activation of TGFβ1. This should in turn cause the epithelial tumour cells to change into the fibroblastoid and invasive phenotype. These fibroblastoid cells themselves then start to produce TGFβ1 which acts on them in an autocrine loop and thus both maintains the fibroblastoid phenotype and also makes it easier to recruit other epithelial cells to the EFC. Further mutations or selective mechanisms should cause some of these invasively growing cells to migrate into blood vessels and out again and finally to form secondary tumours at remote sites. This model conforms to findings which show that increased TGFβ1 expression is also involved in the progression to malignancy in a murine prostate cancer model (Thompson et al., 1992; 1993).

The findings described hitherto were obtained in a combined in vitro/in vivo model system using Ras-transformed mouse-breast epithelial cells. Within the scope of other tests, crucial aspects of this model (EFC, TGFβ1 production in the tumour) were detected in a large number of primary human carcinomas of the kidneys and breast. Thus, in the majority of all the kidney cell carcinomas investigated as well as in a percentage of the breast tumours investigated dependent on the degree of malignity, the occurrence of an EFC is demonstrated by the coexpression of cytokeratin (general epithelial marker) and vimentin (mesenchymal marker). Moreover, in all the tumours investigated, the production of TGFβ1 by the tumour cells themselves has been demonstrated both at the protein level by histochemical staining with anti-TGFβ-antibodies and also at the mRNA level by in situ hybridisation and RT-PCR.

By means of another series of tests carried out within the scope of the present invention it has been shown that the TGFβ-receptor generally assumes a central position in the regulation of EMT and invasive tumour cell growth. Not only in Ha-Ras transformed breast epithelial cells, but in a number of other tumours which originate from other epithelial types and wherein it is not known which oncogenes take over the function of Ha-Ras, the TGFβ-receptor has been identified as the crucial regulator of epithelial plasticity as well as of the invasive growth of the tumour cells. Thus, it has been possible to completely inhibit the invasive growth of two human carcinoma cell lines (kidney carcinoma line MZ 1795, nasopharyngeal carcinoma line KB) (presumably caused by secreted TGFβ1) in collagen gels by means of a neutralising anti-TGFβ1-antibody.

The proof of the above hypothesis was finally provided by means of a dominant-negative TGFβ receptor (TβRII-dn). This TβRII-dn constitutes a so-called "kinase-dead" mutant of the receptor chain II which binds to endogenous receptors of type I, but cannot phosphorylate them. In this way all the TβRII-dn-bound TGFβ-receptor chains of type I are inactivated because they cannot activate any signal transmission even after the binding of the ligand (TGFβ1) since the phosphorylation by receptor chain II required for this is absent. If a dominant-negative TGFβ-receptor of this kind is overexpressed in tumour cells, the entire signal transmission proceeding from the TGFβ-receptor can be inhibited in these cells. The expression of TβRII is thus suitable for simulating the activity of inhibiting TGFβ or inhibiting the signal transmission pathway triggered by the activation of the TGFβ-receptor.

At first TβRII-dn was overexpressed in Ha-Ras-transformed mouse-breast epithelial cells (EpRas). All the clones obtained exhibited greatly delayed tumour growth in nude mice. Moreover, the cells isolated from such tumours had an epithelial phenotype and expressed epithelial markers (E-Cadherin, ZO-1) but no mesenchymal markers (vimentin). This shows that the expression of a TβRII-dn inhibited EFC during tumour formation.

After obtaining these results it was useful to check whether switching off the signal transmission of the TGFβ-receptor also works in tumour cells which have already undergone EFC and thus have a stable mesenchymal and invasive phenotype. The colon carcinoma line CT26 in the mouse was selected as an example of such a cell line. This tumour cell line has a very marked tendency to form lung metastases rapidly after subcutaneous injection in mice, so that the animals die from the lung metastases even after the primary tumour has been surgically removed in good time. This cell exhibits mesenchymal morphology, grows into disordered chains and strings of spindle-shaped cells in the collagen gel and expresses no epithelial markers apart from basal cytokeratins. Instead the cells have a high vimentin expression. If the dominant-negative TGFβ-receptor (TβRII-dn) is overexpressed in these cells, the cells form smaller or larger compact clumps in the collagen gel and grow on plastic as epitheloid cells which form hemicysts (domes) and express large amounts of E-cadherin and ZO-1. The cells were thus obviously changed back, by the TβRII-dn, into cells with an epithelial phenotype (fibroblastoid-epithelial conversion, FEC).

A corresponding activity of the dominant-negative TGFβ-receptor (TβRII-dn) was also observed in vivo. When different, TβRII-dn expressing clones of CT26 cells were injected into mice, the tumour formation was delayed by different amounts depending on the clone. In many clones tumour formation only occurred after 6–8 weeks, as opposed to 1–2 weeks in the case of animals injected with control CT26 cells without TβRII-dn. However, the activity of the TβRII-dn was even more dramatic when the primary tumours were removed from the mice at a certain size and the formation of metastases was expected. In this experiment metastases did not develop in any of the mice injected with TβRII-dn expressing CT26 cells (even after more than 18 weeks) whereas the control animals died of lung metastases within 2–4 weeks after excision of the tumour.

The decisive conclusion from these experiments for the present invention is that inhibiting the signal transmission mediated by the TGFβ-receptor can not only prevent the occurrence of an EFC and the resulting acquisition of invasive properties, but also change any existing, invasively growing tumour cells back into a benign state in which they are no longer invasive.

To sum up, the findings obtained within the scope of the present invention indicate that the increased sensitivity and altered reactivity of the cells, compared with the ability of TGFβ to modify the epithelial phenotype, generally represents a characteristic of epithelial tumour cells. This altered reactivity can be brought about by Ras-(onco)proteins, but also by tyrosinekinases which activate Ras, as well as by other as yet unknown oncoproteins. This altered oncogene-induced mode of reaction to normal environmental signals, such as e.g. those induced by TGFβ1, should lead to altered gene expression in the tumour cell and also incorrect transmission or interpretation of signals between tumour and stroma cells. This abnormal "crosstalk" between tumour cells and their immediate environment would appear to be the driving force for what is commonly known as tumour progression.

Furthermore, the results of the experiments show that activated Ras, overexpressing receptor-tyrosinekinases which activate the Ras signal transmission pathway as well as other, possibly unknown oncogenes co-operate both in the normal development and also in the carcinogenesis with the TGFβ1-receptor. This would appear to involve processes such as the induction/activation of stromal TGFβ1 by the interaction of epithelial and mesenchymal cells as well as EF conversion, induced and maintained by TGFβ1.

The main difference between normal and oncogene-transformed tumour cells should therefore be as follows: TGFβ1 has a physiological, strictly regulated function during the morphogenesis of normal cells. In the tumour cell the transformation by oncogenes causes degeneration of the function of TGFβ1, i.e. constitutive, highly abnormal morphogenetic changes are triggered in the cells.

The present invention thus relates to a pharmaceutical composition containing as active compound a substance which inhibits the activity of TGFβ on tumour cells of epithelial origin, for treating epithelial, invasive tumour diseases which are characterised by a reversible transition of the cells from an epithelial, non-invasive state into an invasive state.

In one embodiment of the invention the pharmaceutical composition also contains substances which inhibit the expression of oncogenic Ras and/or the overexpression of normal Ras or the activity of Ras-activating receptor tyrosinekinases in the cells.

In epithelial invasive tumour diseases the tumour cells have an increased phenotypical plasticity, i.e. they are able to undergo transitions from the epithelial, non-invasive state to the fibroblastoid, invasive state (EF conversion) and vice versa (FE conversion).

The substance which inhibits the activity of TGFβ on the cells or the signal transduction mediated by activation of the TGFβ-receptor is hereinafter referred to as "TGFβ inhibitor".

TGFβs, like the other members of the TGFβ super-family of multifunctional polypeptide factors such as e.g. activins, Bone Morphogenetic Proteins (bmp's), etc., exert their effect by binding to specific cell surface receptors. The type I and type II TGFβ receptors form heterodimeric complexes after binding of the ligand, thereby initiating the signal transmission. The type II receptors, which are assigned to the group of the receptor serine/threonine-kinases in terms of their activity, bind the ligands, but require association with the type I receptors which constitute serine-threonine-kinases in order to be able to pass on the signal obtained from the ligand. Whereas the type II receptors are responsible for the ligand specificity, the functionally different type I receptors heterodimerise with several type II receptors. In this ligand-induced heterodimerisation the type II-receptor chains phosphorylate the type I receptors on serine/threonine groups and thereby activate them. This cooperation of the type II-receptor with a particular type I-receptor causes activation of specific signal transmission pathways and as a result leads to a transcriptional response to the signals transmitted to the cell by the ligands.

The activity of a TGFβ inhibitor is based on the fact that it blocks the cell response triggered by the receptor activation, i.e. it prevents the TGFβ-receptor system from being activated and hence the cell signal transmission pathway from being actuated.

Since it is the type I receptors which are responsible for the specific transcriptional response which eventually produces the fibroblastoid phenotype after the binding of the ligands to the type II receptor, and to the type I receptor, the type I receptor represents one of the target molecules for the TGFβ inhibitor. Because of the need for phosphorylation of the type I receptor by the type II receptor (and on the basis of the results obtained with dominant negative type II receptors whose serinekinase activity has been destroyed by mutation, the type II receptor is also a possible target molecule for inhibitors.

Other mechanisms for the activity of a TGFβ inhibitor are thus based on preventing the interaction between the ligand TGFβ and the type II receptor, preventing the signal transmitted from the type II receptor to the type I receptor which brings about the activation of the type I receptor. Finally, blocking the binding of TGFβ to the type I receptor, inhibiting the activity of the type I receptor or inhibiting an effector molecule of the signal transmission pathway activated by the type I receptor are all possible methods of attacking inhibitors.

Examples of inhibitors are antibodies which neutralise the TGFβ, particularly monoclonal antibodies, TGFβ antisense-RNA molecules (Fakhrai et al., 1996) or dominant-negative TGFβ receptors of type I or II.

The invention relates, according to a further aspect, to screening processes for identifying pharmacologically active substances for treating epithelial, invasive tumour diseases which are characterised by a reversible transition of the cells from an epithelial, non-invasive state into an invasive state.

One method of finding suitable, particularly low-molecular, inhibitors, comprises determining, in a first step, which of the type I receptors is responsible for the transition from the epithelial to the fibroblastoid state of the cells. To do this, the EpRas-cell line used within the scope of the present invention (or one of the other cell lines used which are capable of bringing about the EF conversion or have already undergone one), is interrogated to see which TGFβ-type I/II receptor it expresses. This interrogation may be carried out by RT-PCR ("Reverse Transcriptase Polymerase Chain Reaction") using oligonucleotides, derived from known TGFβ-type I or type II receptors, as PCR primers in order to amplify the relevant receptor-DNA from EpRas-DNA and thus identify the TGFβ-type I or type II receptor expressed in these cells. The experiments described in the Examples with a dominant-negative mutant of the human type II receptor TβR-II (only this chain occurs in all the known receptors for TGFβ1,2,3; Wrana et al., 1992, Wrana et al., 1994) confirm that this TGFβ-type II receptor subtype (as such) is necessary, directly or indirectly, for the signal transmission which leads to the EF conversion. This TGFβ-type II receptor subtype thus constitutes one of the target molecules for the TGFβ inhibitor. This satisfies an esential precondition for establishing a cellular or biochemical screening assay which can be used to screen specifically for substances which inhibit this target molecule.

Next, an investigation is carried out in a cell which is undergoing the EF conversion or in which the EF conversion can be reversed by inhibiting the TGFβ receptor signal transmission to determine which of the processes taking place in the cell by EF conversion or reversal thereof is most suitable for establishing a screening assay. Appropriately the EpRas cells used in the Examples or the CT26 cells which are also well characterised within the scope of the present invention may be used.

The effects to be expected can be divided into two groups: the first group includes the effects of TGFβ on normal mesenchymal and epithelial cells, e.g. in wound healing, described in the literature. The second group of changes are those which occur in particular with the activity of TGFβ on transformed cells (such as e.g. in the experiments described within the scope of the present invention). Whereas the TGFβ effects of the first group can be adduced for a primary HTS screen ("High Throughput Screen"), any inhibitor candidates found must be tested without fail for their inhibiting activity on the TGFβ effects of the second group.

The TGFβ effects of the first type include i) the induction of extracellular matrix proteins, such as fibronectin, laminin, elastin; ii) the induction of the protease inhibitor PAI (Plasminogen Activator Inhibitor) and hence the inhibition of cell protease activity, and iii) an inhibition of cell growth and induction of programmed cell death (apoptosis) in certain cell types. These include in particular normal epithelial cells as well as only slightly degenerate, essentially still epitheloid tumour cell lines. The induction of PAI-1 expression as well as the TGFβ-induced apoptosis are possible procedures which may be used to design a cell assay system for screening substances which may act as TGFβ receptor inhibitors. The effect chosen is used directly as a system for demonstrating the inhibiting activity of the substance.

In order to find out whether the EF conversion in the EpRas-cell line used within the scope of the present invention triggered by the activation of the TGFβ receptor system is transmitted via the same type I/type II receptors as the induction of PAI (or another molecule regulated by TGFβ) in untransformed cells, e.g. in the normal starting cell line EpH4 (also used within the scope of this invention), it is possible to check e.g. whether the induction of PAI (or another molecule) or the growth inhibition which is very marked in this cell line is blocked by a dominant-negative mutant of the same type I or II receptor which also blocks the EF conversion. In the case of the CT26 cells which overexpress the dominant-negative type II receptor (TβRII-dn), it has been shown that, in the TβRII-dn expressing CT26 clones which reverted to epithelial cells, activation of a PAI-1 promoter-controlled reporter gene was completely inhibited by TGFβ-1. The extent of the PAI-I inhibition of the inhibition of reporter gene expression by PAI-I correlated directly with the ability of the different clones to form tumours in the animal. Moreover, a special CT26 clone, which had recovered complete TGFβ-1-inducibility of the PAI-1 promoter-reporter gene construct after lengthy passage in vitro (presumably by repressing the TβRII-dn expression) also regained the ability to form metastasising tumours in the mouse.

The confirmation of the correlation between EFC, tumour formation and TGFβ receptor type II function using the TβRII-dn experiments provides the prerequisite for a screening assay based on a PAI-1 reporter gene test cell. This test cell, which is a human or animal cell, is stably transformed with a plasmid, in which a reporter gene, e.g. the luciferase gene, is under the control of the regulatory sequence of the PAI gene (or a gene which codes for another molecule regulated by TGFβ, e.g. for an extracellular matrix protein). The test cell is also transformed with the human type I or type II receptor, which was shown, after further tests, to be most efficient both at triggering the EF conversion and also at inducing PAI or another molecule regulated by TGFβ. The human TGFβ type II receptor used for the construction of the TβRII-dn is one of the possible target molecules for a TGFβ inhibitor. The control cell used is expediently a parallel-cell clone in which the PAI-1-promoter controlled reporter gene is activated by another receptor not related to the TGFβ receptor (e.g. members of the FGF (fibroblast growth factor) receptor-tyrosinekinase family).

If a substance which wholly or partially inhibits the TGFβ-induced reporter gene expression is found in a screening assay of this kind, it can be concluded that either the selected ligand-activated type I/type II receptor or the signal transmission mediated by this receptor is blocked by this substance. The same substance should not have any influence on the slight basal reporter gene expression in the control cell in which the reporter gene has been activated not by TGFβ, but by FGF. The test systems in which the reporter gene activation is measured can be used in robotised High Throughput Screen (HTS) processes.

A second possible way of measuring the blocking of the TGFβ receptor function by test substances can easily be measured by the removal of the growth inhibition and apoptosis brought about by TGFβ. Since TGFβ efficiently induces apoptosis in normal EpH4 cells under certain conditions, effective inhibitors of the TGFβ receptor should act as survival or growth stimulating factors. EpH4 cells in which another apoptosis-inducing receptor has been expressed may be used as control cells. The Fas receptor, which efficiently induces apoptosis in virtually all cell types after the binding of a special Fas ligand, is particularly suitable. The removal of an apoptotic effect by effective TGFβ receptor inhibitors has the advantage that it can easily be measured in commercially obtainable test systems (e.g. in the MTS assay which detects the number of live, metabolically active cells), and that toxic substances (which cause rather than prevent cell death) can easily be identified as such. Thus, this test system is also suitable for HTS primary screens.

Another possible cell assay system with which substances can be tested for their inhibiting activity on the EF conversion triggered by activation of the TGFβ receptor system, is based on the expression of proteins which are characteristic of the fibroblastoid cell type after EF conversion and are thus an indicator of the occurrence of EF conversion. One example of this is vimentin (Reichmann et al, 1992): it has been shown within the scope of the present invention that expression thereof goes hand in hand with the EF conversion triggered by cooperation of Ras and TGFβ. Other examples of other markers of the fibroblastoid phenotype are the loss of the expression of E-Cadherin mRNA as well as the de-novo expression of fibronectin and diverse proteases (UPA, TPA, Reichmann et al, 1992). A suitable test cell transformed by Ras or another oncogene is transformed with a plasmid in which a reporter gene is under the control of the vimentin gene promoter or of promoters of one of the other fibroblastoid marker genes mentioned. The modulation of the reporter gene expression by a test substance should then correlate with the modulation of the EC conversion brought about by the same inhibitors.

Another possible way of finding substances which inhibit the activation of the TGFβ receptor system uses the expression of TGFβ itself as a detection system. This assay principle is based on the finding reached within the scope of the present invention that the activation of the TGFβ receptor system in oncogene expressing cells by the ligand TGFβ causes the autocrine production of TGFβ which acts on the cells in an autocrine loop. In an assay of this kind, which can detect both the activation of the TGFβ receptor system and also the induction of the autocrine TGFβ loop brought about by the expression of Ras (the activity of substances which inhibit TGFβ expression, in a test of this kind, do this on the basis of their effect on the activation of the TGFβ receptor system and their effect on Ras), the cells contain a reporter gene construct which is under the control of the TGFβ gene promoter (Kim et al, 1989).

Biochemical assays in which TGFβ inhibitors are identified, the activity of which is based on the fact that they inhibit the TGFβ signal transmission pathway, may be carried out as follows, for example: in an assay format the autophosphorylation of the TGFβ receptor type II or the cytoplasmic domain thereof which contains the kinase domain is measured in vitro on serine or threonine groups, in the presence and in the absence of test substances (potential TGFβ inhibitors), a kinase assay of this kind being carried out using methods known from the literature, e.g. as described by Lin et al., 1992, or Braunwalder et al., 1996, and using a receptor (or a domain thereof) prepared by recombinant methods, e.g. in *E. coli*. In an alternative assay format, the ability of the TGFβ receptor type II to phosphorylate the TGFβ receptor type I or its so-called GS domain (Wrana et al., 1994), is measured, again according to the known principle of kinase assays, in the presence and absence of potential inhibitor. The modification of an assay of this kind for a High Throughput Format can be carried out using commercially available technologies such as filter plates, FLASH plates (Amersham) or SPA (Scintillation Proximity assay)-Beads (Amersham).

In one of the test systems described, inhibitors of the TGFβ receptor found in the primary screen are expediently tested for their specificity in secondary screens. This can be done particularly by direct inhibition of the TGFβ-dependent EF conversion of EpRas cells in collagen gels. Another possibility is the incubation of converted EpRas cells (e.g. from mouse tumours) plated out at low density on plastic dishes with the inhibitor of the TGFβ receptor found. Effective substances should trigger the conversion of fibroblastoid into epithelial cells even in the presence of TGFβ. The same substances should cause re-epithelialisation (FE conversion) in CT26 cells. Finally, particularly suitable active substances in mice which were injected with CT26 cells can be tested to see whether they slow down the growth of the primary tumour or metastasisation after excision of the primary tumour.

The substance which inhibits the expression or the function of oncogenic Ras and/or the overexpression of normal Ras (or the consequences of this overexpression) and/or the activation of normal Ras by receptor tyrosinekinases in the cells is hereinafter referred to as "Ras inhibitor".

Ras inhibitors for the purposes of the present invention either inhibit Ras directly, by inhibiting the activation/function of Ras itself or by inhibiting the activation/function of a Ras-effector molecule which acts below Ras in the Ras signal transmission pathway. Examples are inhibitors of Raf, such as Raf antisense-oligonucleotides (Monia et al., 1996). For cases where the activation of Ras cannot be put down to a change in Ras itself, but it due to the constitutive activation of receptor-tyrosinekinases acting above Ras, inhibition of Ras-activation can also be brought about by inhibiting these receptors. Examples of receptors of this kind are the receptor-tyrosinekinases EGF receptor ("Epidermal Growth Factor Receptor") and homologous receptors such as HER-2, HER-3 or HER-4. Examples of chemical compounds which inhibit the EGF receptor can be found in WO 96/07657. Known Ras inhibitors are monoclonal antibodies (Furth et al., 1982), dominant-negative mutants (Stacey et al., 1991; Quilliam et al., 1994) and antisense-RNA. Examples of low-molecular Ras inhibitors are inhibitors of Ras-Farnesyl transferases (Kohl et al., 1993; Kohl et al., 1994; Kohl et al., 1995).

In order to screen for other low-molecular Ras inhibitors, genes coding for mutations of the Ras proteins H-Ras, K-Ras or N-Ras, which lead to constitutive activation of Ras, are introduced into mammalian cells, e.g. by means of retroviral vectors, and the selective cytotoxic activity of test substances on the ras-transformed cells is determined. A suitable method of identifying ras inhibitors is described e.g. in der EP-A 604 181.

Examples of Ras-transformed cell lines which may be used as test cells for the identification of Ras inhibitors, have also been described by Andrejauskas and Moroni, 1989, as well as by Jenkins et al., 1993.

Ras inhibitors can also be identified with an assay based on the EpRas-cell line used within the scope of the present invention. For this, the cells contain a reporter gene construct in which the reporter gene is under the control of the regulatory sequence of the TGFβ gene. First of all TGFβ is applied to the cells in order to bring about the EF conversion. Then the cells are treated with the test substances. Test substances which are capable of inhibiting the activity of the reporter gene can be assumed to be Ras inhibitors. This can then be confirmed in secondary screens in which the substances are investigated to see whether they can inhibit the TGFβ-induced EF conversion of EpRas cells in collagen gels or reverse the EFC which has already taken place.

The pharmaceutical compositions according to the invention can be used, firstly, to prevent the cells from changing into the fibroblastoid state and becoming invasive, thus preventing or reducing their tumorigenicity. Secondly, the pharmaceutical compositions according to the invention can also be used to bring about the conversion of existing fibroblastoid and invasively growing tumour cells into non-malignant or less malignant epithelial cells.

The pharmaceutical composition according to the invention may be used on the one hand to prevent the transformation of the cells from the epithelial, non-invasive state into a fibroblastoid, invasive state. One example of this is its administration after surgical removal of a primary tumour to prevent any tumour cells present from becoming invasive and producing further tumours by metastasisation. Moreover the pharmaceutical composition according to the invention can also slow down tumour growth by the same mechanism, as has been shown with the aid of the TβRII-dn expressing CT26 cells.

The pharmaceutical composition according to the invention may, on the other hand, be used to reverse an EF conversion of the cells which has already taken place. Once the conversion has taken place, TGFβ maintains the fibroblastoid state by means of an autocrine loop. The administration of a TGFβ inhibitor on its own in this case switches off the autocrine loop and thus reverses the fibroblastoid, invasive state of the cell into the normal, epithelial state. However, this reversal is temporary, and there is no fundamental change to the transformed state of the cell brought about by Ras or other oncogenes. This means that when the TGFβ inhibitor is removed the EF conversion could start up again. If, on the other hand, an oncogene inhibitor, e.g. a Ras inhibitor or an HER-1/2 inhibitor, is administered, possibly in addition to the TGFβ inhibitor, the transformed state of the cell is cancelled, the cell behaves like a normal epithelial cell and reacts correspondingly normally to TGFβ, i.e. the effect of TGFβ on the cell cannot bring about EF conversion and even leads to growth inhibition of the tumour cell.

The conjecture that TGFβ (receptor) inhibitors could cause slowing down or even inhibition of tumour growth is supported by the following state of affairs: most tumours constantly produce TGFβ (see below) which is released into the environment and has an immunosuppressant effect there, i.e. inhibits the function of cytotoxic T-lymphocytes and other cells of the immune system. If the TGFβ receptor inhibitor causes the transformation of invasive tumour cells into non-invasive, more epithelial cells, these should switch off the secretion of TGFβ and thus be more easily attacked and lysed by cytotoxic T cells.

In order to achieve optimal activity, the pharmaceutical composition according to the invention preferably contains a combination of TGFβ inhibitor and Ras inhibitor.

In the transition of epithelial cells into the fibroblastoid state, fibroblastoid marker proteins, e.g. vimentin, are expressed more intensely. The increase in the expression of these markers (see below) is thus one of the diagnostic parameters for tumour diseases which can be treated using the pharmaceutical composition according to the invention.

These tumour diseases include adenocarcinomas of the breast (Heatley et al., 1993), kidney cell carcinomas (Beham et al., 1992), carcinosarcomas of the breast (Wargotz and Norris, 1989), carcinosarcomas of the oesophagus (Guarino et al., 1993) or of the female genital tract (de Brito et al., 1993), epitheloid sarcomas as well as spindle cell carcinomas of various locations, e.g. lung carcinomas with spindle cell components (Matsui et al., 1992) or spindle cell carcinomas of the gall bladder (Nishihara et al., 1993).

The pharmaceutical composition according to the invention is preferably used to treat breast tumours and kidney cell carcinomas.

The pharmaceutical compositions according to the invention are administered to humans in doses of 0.01 to 100 mg/kg body weight, preferably 0.1 to 15 mg. Apart from the active compounds the pharmaceutical composition contains the usual inert carriers and excipients. The skilled person will find methods of formulating pharmaceutical preparations in the relevant textbooks, such as Remington's Pharmaceutical Sciences, 1980.

FIGURE SUMMARY

FIGS. 1A–1D conversion of EpRas cells into fibroblastoid cells during tumour formation in mice.

Figure 1:
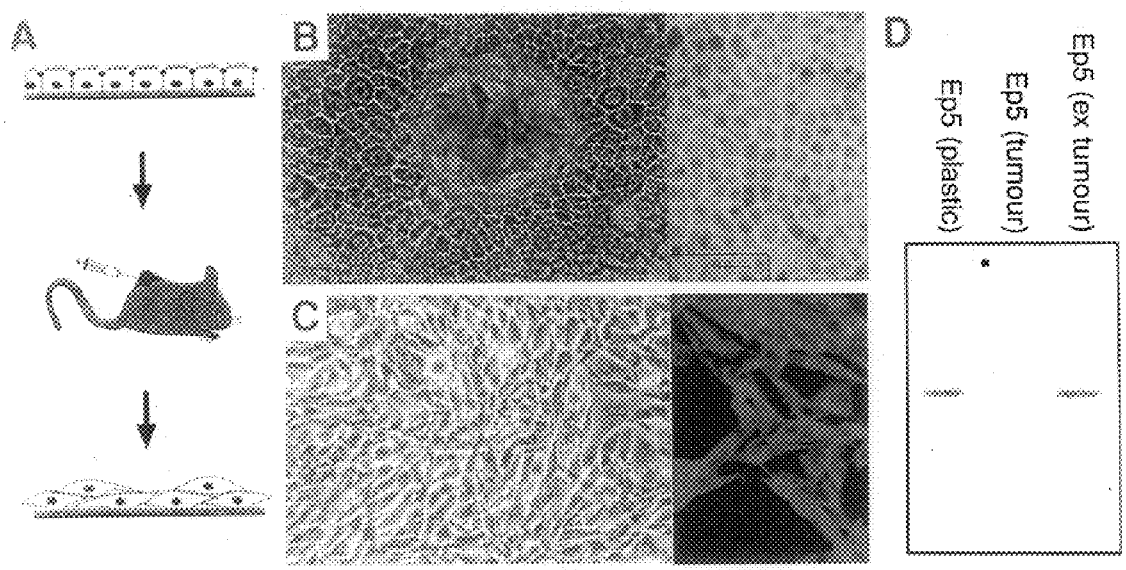
FIG. 1A is a schematic diagram illustrating the strategy which was used to study the epithelial-fibroblast conversion (EFC) of Ras cells in vivo.
FIG. 1B is a photomicrograph showing cells of the clone Ep5 before subcutaneous injection.
FIG. 1C is a photomicrograph showing that Ep5 cells isolated from a tumour 28 days after injection.
FIG. 1D is a Southern Blot analysis of the EpRas-clone (Ep5): (i) before injection (Ep5 plastic), (ii) removed from the tumour (Ep5, tumour), and (iii) removed from the tumour and recultivated for 5 days in G418 (Ep5, ex tumour).

FIGS. 2A–2H Conversion epithelial/mesenchymal (EFC) during tumour development: time scale and behaviour of donor and receiver cells: after 3 days (FIGS. 2A and 2E), 7 days (FIGS. 2B and 2F), 15 days (FIGS. 2C and 2G) and 28 days (FIG. 2H). FIG. 2D is a photomicrograph showing parental EpH4 cells 15 days after subcutaneous injection.

FIGS. 3A–3D Organogenesis and epithelial polarity are destroyed by serum or TGFβ1.

FIG. 3A is a photomicrograph showing Ep4H cells in a serum-free collagen gel.

FIG. 3B is a photomicrograph showing EpRas cells in a serum-free collagen gel.

FIG. 3C is a photomicrograph showing cells after the addition of 10% FCS.

FIG. 3D is a photomicrograph showing EpRas cells grown with TGFβ1 (5 ng/ml).

FIGS. 4A–4F TGFβ1 destroys the cell polarity in Rastransformed breast epithelial cells.

FIG. 4A is a transmission electron micrograph of EpRas cells in serum-free collagen gel.

FIG. 4B is a photomicrograph of a frozen section through an alveolar cyst formed by EpRas cells in serum-free collagen gel.

FIG. 4C is a photomicrograph of a Lowicryl section through an alveolar cyst formed by EpRas cells in serum-free collagen gel.

FIG. 4D is a transmission electron micrograph of disordered strings of EpRas cells after treatment with TGFβ1.

FIG. 4E is a photomicrograph of a frozen section through disordered strings of EpRas cells after treatment with TGFβ1.

FIG. 4F is a photomicrograph of a Lowicryl section through disordered strings of EpRas cells after treatment with TGFβ1.

FIGS. 5A–5D Fibroblastoid EpRas cells are highly invasive in the chicken embryo heart invasion assay. FIGS. 5A–5D are photomicrographs of in vivo fluorescence-labeled cells co-cultured for 7 days with chicken embryo heart fragments: non-tumorogenic epithelial starting cells (EpH4 cells) (FIGS. 5A–5B), non-converted epithelial EpRas cells (FIG. 5C), and converted fibroblastoid cells after TGFβ1 treatment (FIG. 5D).

FIGS. 6A–6F TGFβ1 maintains the fibroblastoid phenotype of converted EpRas cells via an autocrine loop. FIGS. 6A–6D are photomicrographs of a cell clone, from fibroblastoid cells isolated from a tumour and grown in medium containing 1% FCS, on day 1 (FIG. 6A), day 3 (FIG. 6B), day 5 (FIG. 6C) and day 10 (FIG. 6D). FIGS. 6E–6F are photomicrographs of the same cells after a further 8 days in collegian gels, in the absence (FIG. 6E) and in the presence (FIG. 6F) of TGFβ1 neutralizing antibodies.

FIGS. 7A–7B Converted EpRas cells produce high concentrations of TGFβ1.

FIG. 7A shows a semi-quantitative PCR analysis for TGFβ1 -mRNA.

FIG. 7B show TGFβ1 concentrations in cell culture supernatants as measured by Western Blot and ELISA FIGS. 8A–8F TGFβ1 triggers the transition from the epithelial to the fibroblastoid state as well as the invasiveness of the cells in experimentally induced tumours.

FIGS. 8A–8B are photomicrographs of frozen sections of a tumour on day 4.

FIGS. 8C–8D are photomicrographs of frozen sections of a tumor on day 15.

FIG. 8E is a photomicrograph of EpRas cells injected subcutaneously into nude mice without 3-Elvax Slow Release Pellets charged with recombinant (active) TGFβ1.

FIG. 8F is a photomicrograph of EpRas cells injected subcutaneously into nude mice with 3-Elvax Slow Release Pellets charged with recombinant (active) TGFβ1.

Figure 9:
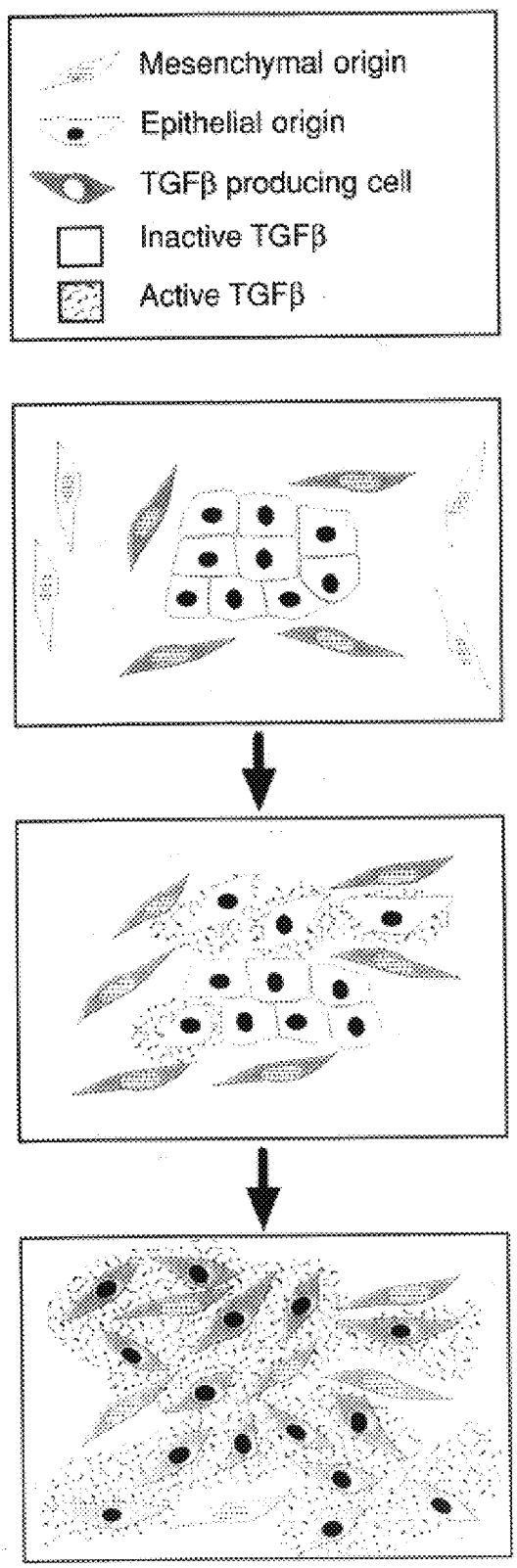

FIG. 9 model for the activity of TGFβ1 in tumour development

FIGS. 10A–10D TGFβ1 induces in vitro morphogenesis and apoptosis in normal mammary gland epithelial cells.

FIG. 10A is a photomicrograph showing that, in the absence of additional TGFβ1, the cells do not form any tubular structures.

FIG. 10B is a photomicrograph showing that, in the presence of 0.1 ng/ml of TGFβ1 the cells form branched structures, but these branched structures lack lumina.

FIG. 10C (lower magnification on the left, higher magnification on the right) is a photomicrograph showing that higher concentrations of TGFβ1 cause cell death (apoptosis).

FIG. 10D is a photomicrograph showing that, if the TGFβ1 is removed, on day 7 by washing, from cultures having the structures shown in FIG. 10C, the cells form distinct hollow structures.

Figure 11:
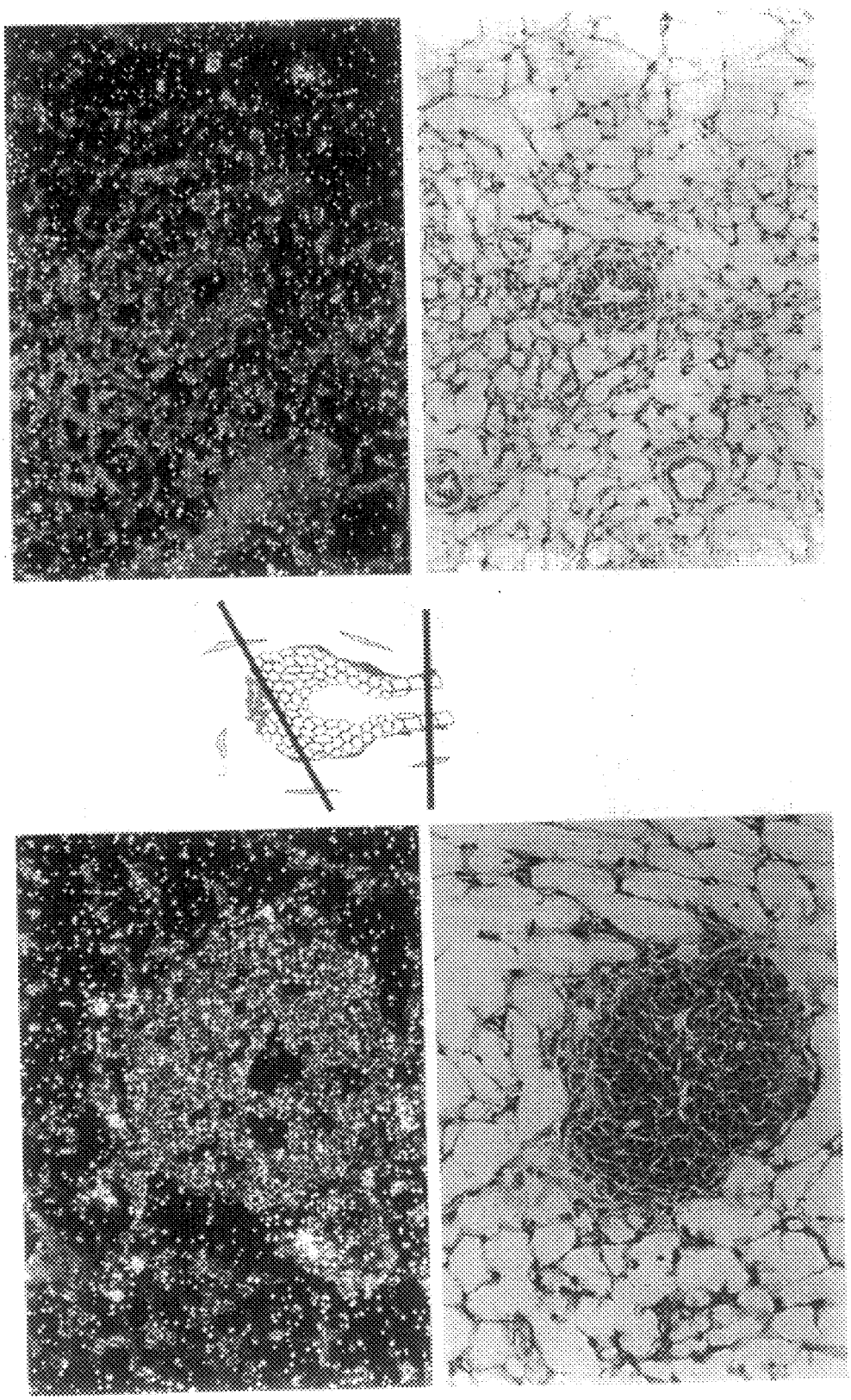

FIG. 11 In vivo expression of TGFβ1 during the formation of the normal breast

Figure 12:
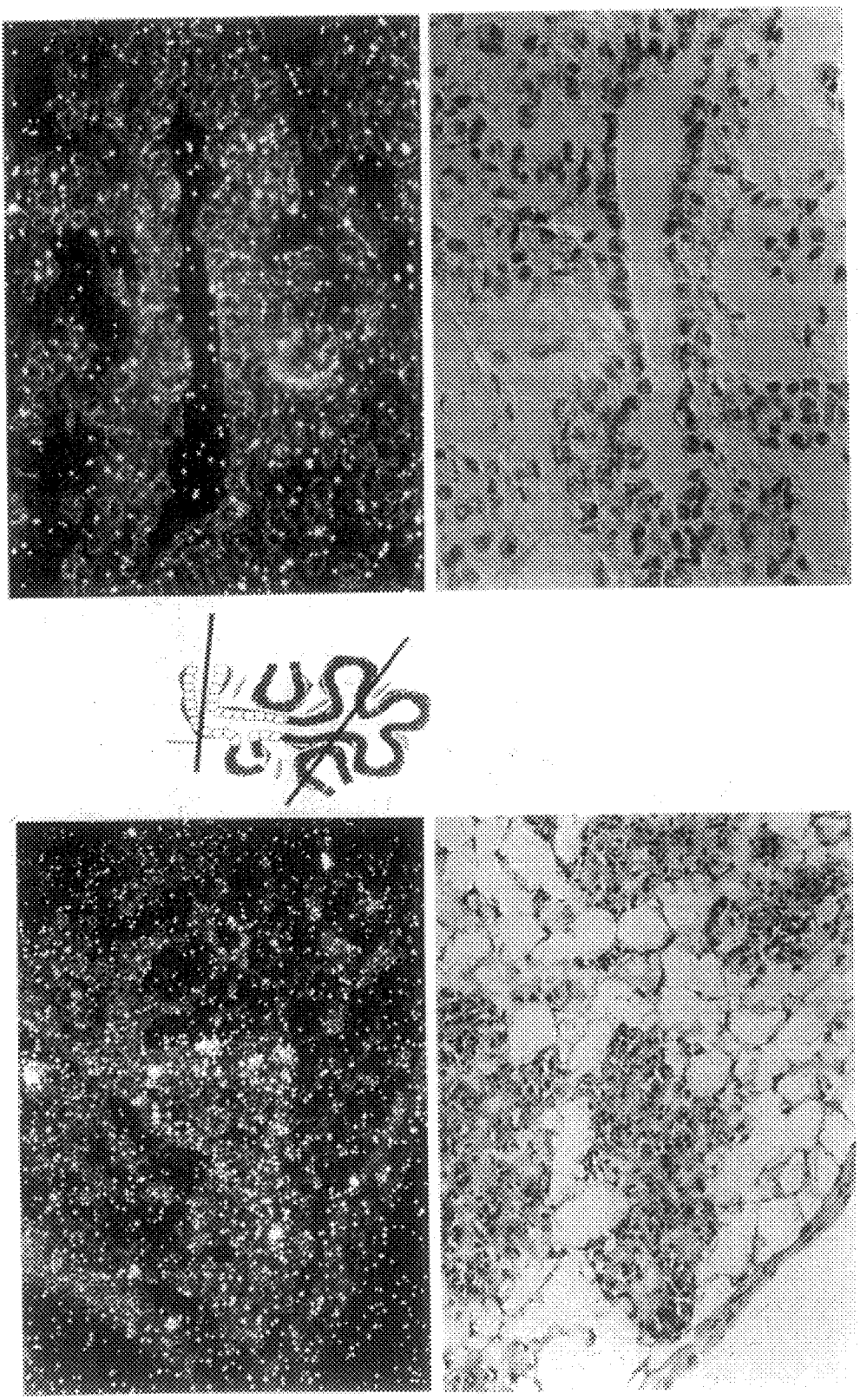
Figure 13:
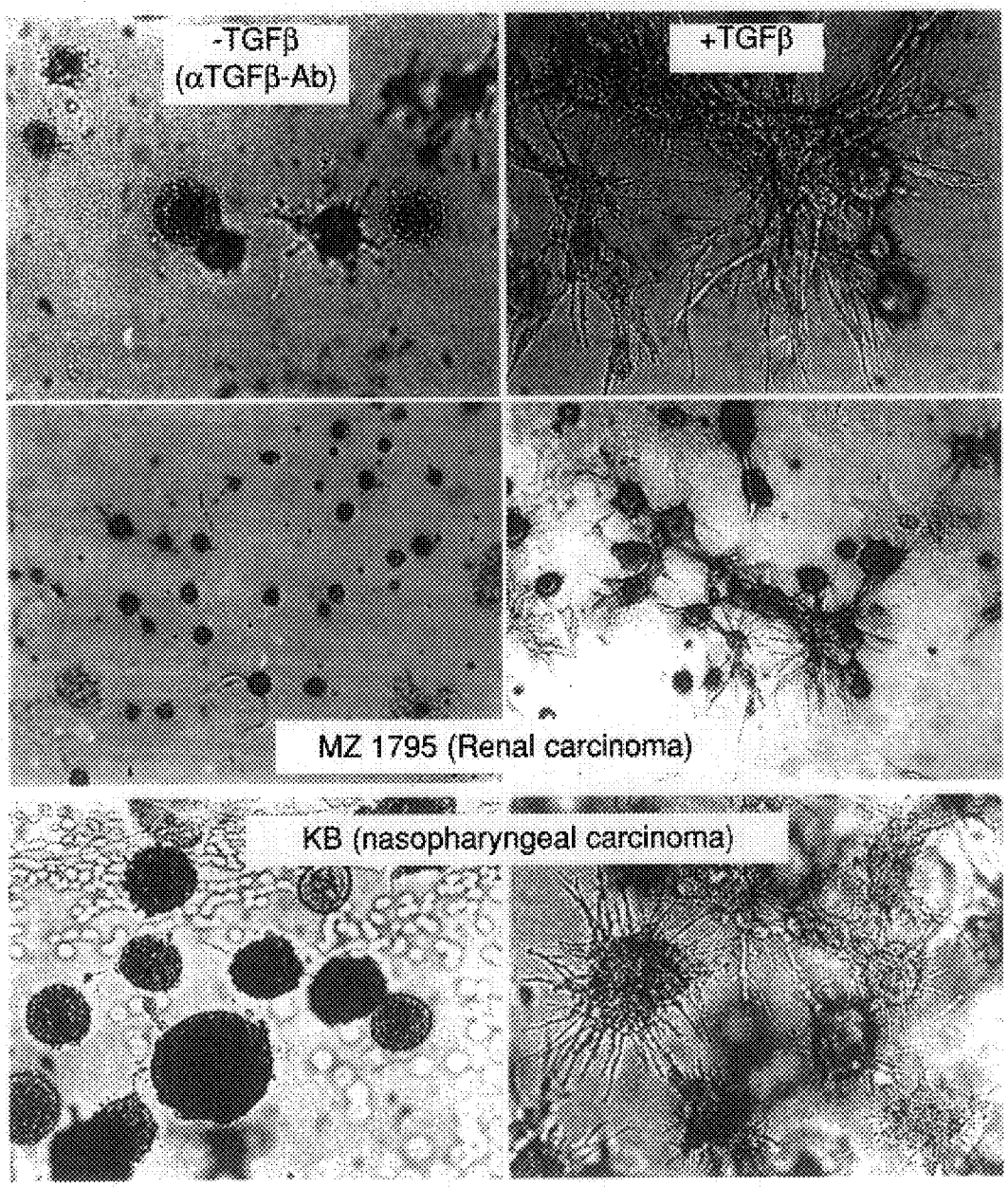
Figure 14:
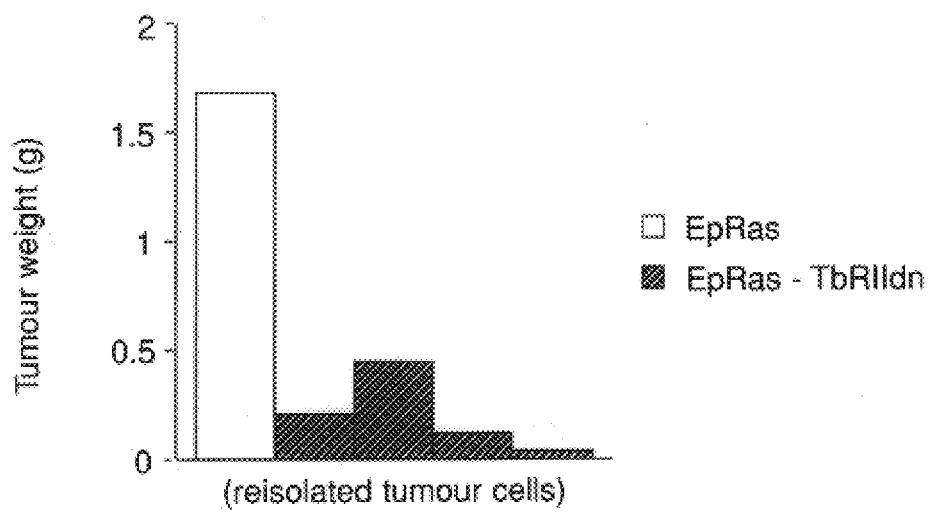
Figure 14:
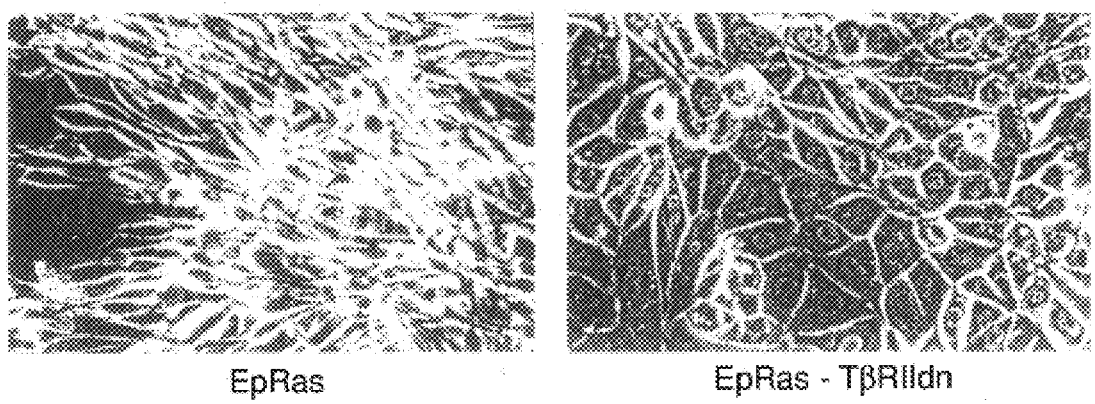
Figure 15:
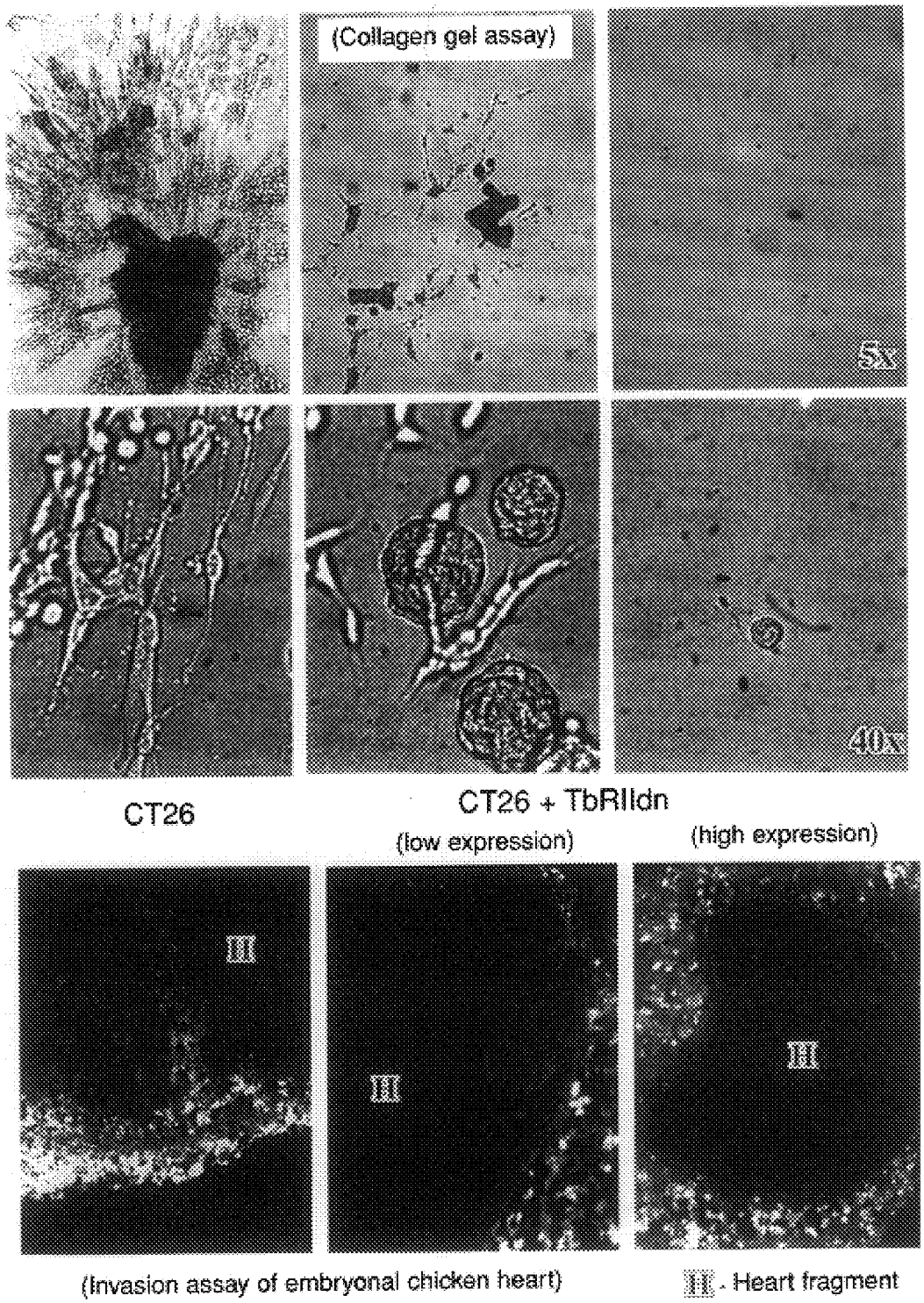
Figure 16:
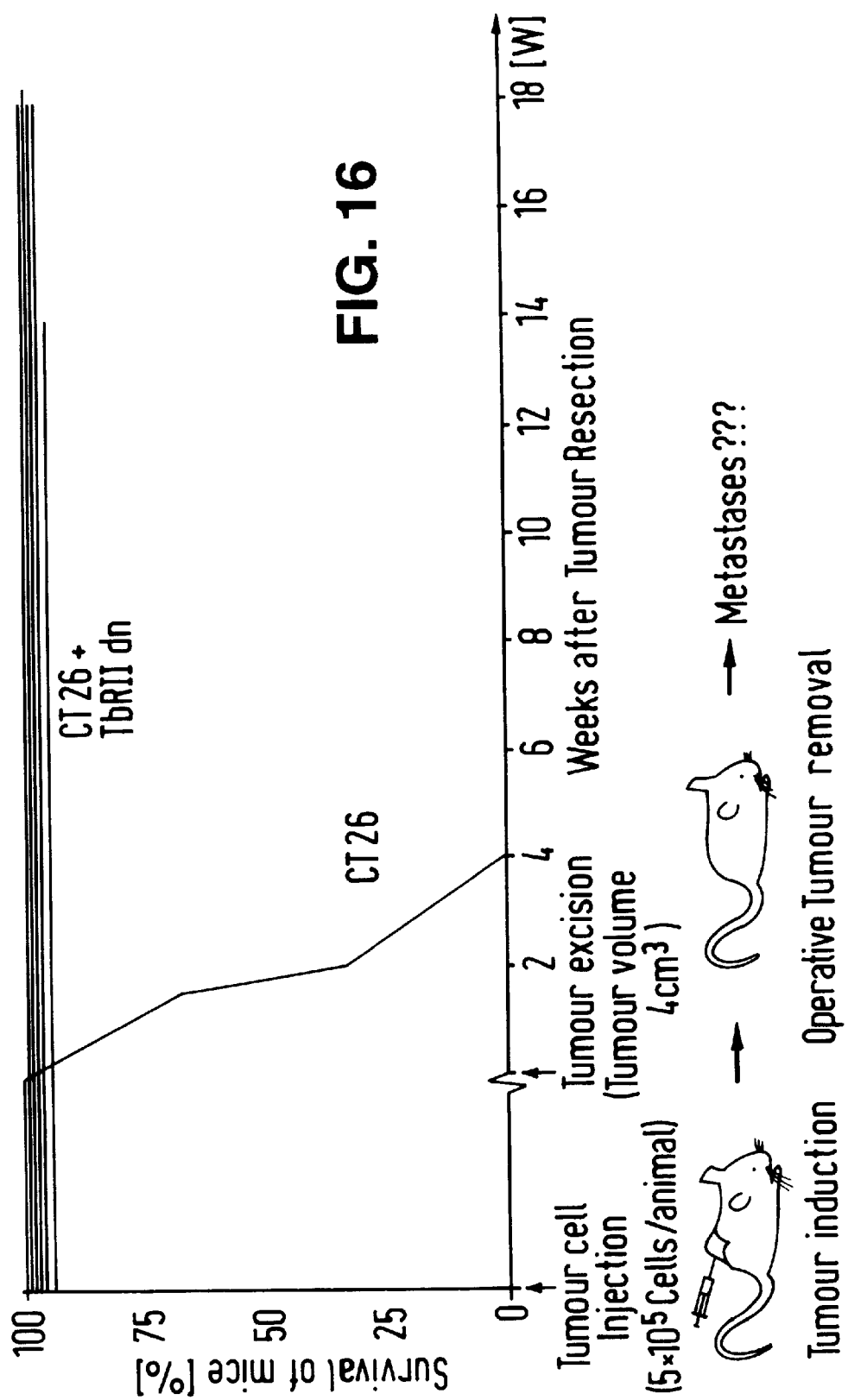
Figure 17:
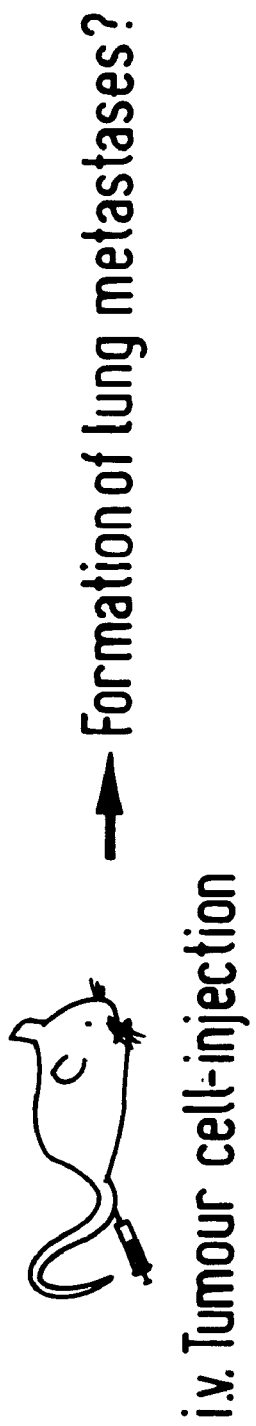
Figure 17:
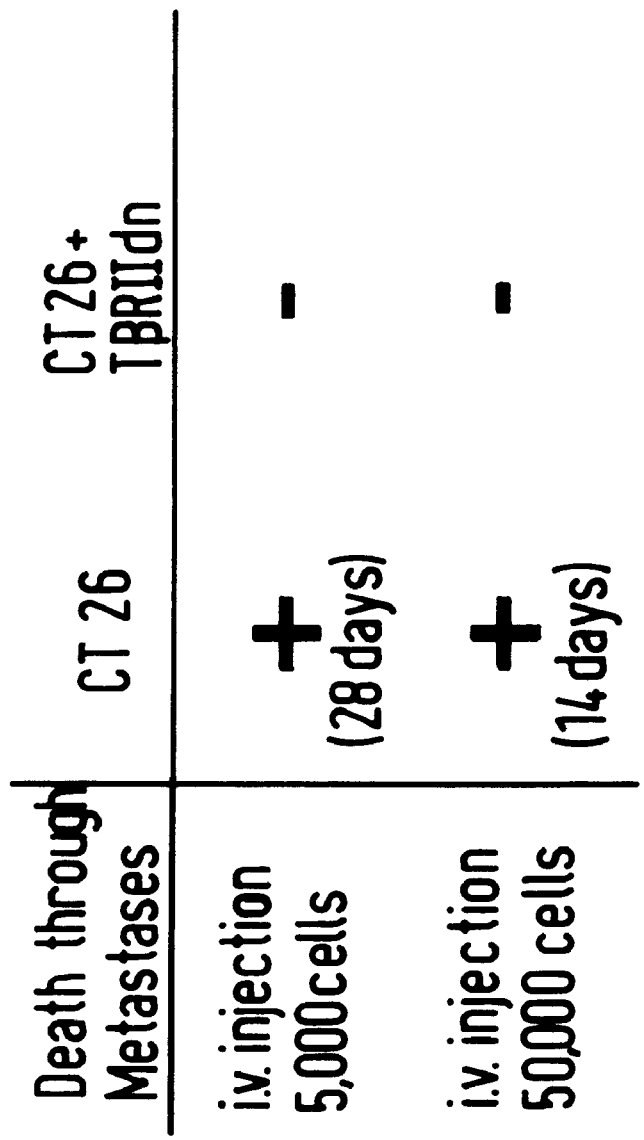

FIG. 12 In vivo expression of TGFβ1 during the breakdown of the fully developed mammary gland after ablactation FIG. 13 inhibition of the invasivity of human tumour cells by TGFβ-neutralising antibodies FIG. 14 expression of a dominant-negative TGFβ-receptor (TβRII-dn) in Ras-transformed breast epithelial cells inhibits EFC and tumour growth FIG. 15 expression of TβRII-dn in mouse-colon carcinoma cells (CT26) prevents growth in collagen gels and invasivity in vitro FIG. 16 expression of TβRII-dn in CT26 cells inhibits metastasisation in vivo FIG. 17 TβRII-dn expressing CT26 cells are incapable of forming metastases in the lung even after intravenous injection FIG. 18 expression of a PAI-1-promoter-reporter construct in CT26− and CT26+TβRII-dn cells ]

EXAMPLES

In the following Examples, the following materials and methods were used unless otherwise stated:

a) Cell Culture

EpRas cells were prepared by infecting the parental breast epithelial cell line EpH4 (a subclone of the spontaneously immortalised breast epithelial cell line Ep1 (Reichmann et. al, 1992) selected for the strong impression of a polarised phenotype) with a helper-free, v-Ha-Ras expressing retroviral vector (Redmond et al., 1988). The selection and expansion of the polarised epithelial clones was carried out as described by Reichmann et al., 1992. For this the cells were cultivated on plastic dishes in growth medium (Dulbecco's modified Eagles medium; (DMEM), containing 10% FCS (Boehringer Mannheim) and 20 mM HEPES, and subcultivated in a ratio of 1:3 twice a week. For the induction of hemicyst(dome) formation EpRas cells and cells of the parental line EpH4 were cultivated at high density for one week without subcultivation.

The human tumour cell lines MZ 1795 (kidney carcinoma; Seliger et al. 1996) and KB (nasopharyngeal carcinoma ATCC CCL17; Derynck et al., 1985) were obtained from the ATTC. They were cultivated in the same medium as the mouse EpH4 cells.

The mouse colon carcinoma line CT26, the establishing of which was described by Brattain et al., 1980, was also cultivated in the same medium as the mouse-EpH4 cells.

In order to express the human, dominant negative TGFβ receptor type II (TβRII-dn, Wrana et al., 1992) in mouse-EpH4 and CT26 cells, the corresponding cDNA (Wrana et al., 1992) was inserted in the helper-free retrovirus vector pbabe-puro (Morgenstern and Land, 1990). The retrovirus-DNA was transfected into BOSC 23 packaging cells (Pear et al, 1993) and the virus-producing, Mitomycin-C treated BOSC 23 cells cocultivated with EpH4 or CT26 cells. Infected clones were selected with G418 and expanded in Dulbecco's modified Eagles medium (DMEM), containing 20% FCS (Boehringer Mannheim) and 20 mM HEPES. The expression of the TβRII-dn protein was detected in the Western Blot using a haemagglutinin (HA) epitope present in the construct.

b) Growth of Organotypical Cell Structures in Collagen Gels

Semiconfluent cultures of the cells to be analysed were trypsinised and adjusted to a final concentration of $4 \times 10^4$ cells per ml with ice-cold growth medium. Equal volumes of the cell suspension and an acidified solution of rat's tail collagen type 1 (Sigma) were mixed at 4° C., applied to 35 mm tissue culture dishes and incubated for 30 min at 37° C., in order to allow the solution to set to a gel. To allow the cells to form organotypical structures, the collagen gels were covered with a serum-free medium (MEGM; Promocel) containing bovine pituary extract (BPE), recombinant epidermal growth factor (EGF), hydrocortisone and insulin (in the concentrations recommended by the manufacturer). Where stated, 5 or 10% FCS or 5 ng/ml recombinant TGFβ1 (literature) were added. The medium covering the collagen gels was changed every two days. In order to neutralise the TGFβ1 produced by the cells or cell structures in the collagen gels a monoclonal antibody against TGFβ1 (Genzyme) or control antibody is used in concentrations of up to 50 μg/ml.

c) Tumour Induction in Mice and Re-isolation of Cells from Tumours or Collagen Gels Confluent EpRas or EpH4 cells were trypsinised and counted. Then $10^5$ cells, suspended in 0.1 ml PBS, were injected subcutaneously or into the mammary gland of 5 week old BALB/c mice or nude mice. The mice were killed after different lengths of time (between 3 and 28 days) and the tumours (or tissue zones which the injected cells contained) were excised. For the subsequent histological analysis the tissue was immediately flash-frozen in liquid nitrogen. To isolate the tumour cells for further growth in the tissue culture, the tissue was cut into small pieces under sterile conditions using two opposing scalpels and digested with 2 mg/ml collagenase type 1 (Sigma) for 1 hour at 37° C. In order to remove the remaining host cells which lacked the retroviral neomycin or hygromycin resistance markers of the donor cells, the cells obtained from the tumours were grown for the first 5 days in the presence of G418 or hygromycin. The collagen gels were digested with collagenase in a similar manner, in order to isolate the cells for the subsequent tissue culture.

For tumour induction with CT26 cells or CT26-TβRII-dn cells, $1 \times 10^6$ cells per animal were injected subcutaneously into nude mice under the skin of the back. The size of the detectable tumours was determined every 3 days and the animals were killed when the tumours exceeded a sze which was tolerable for the wellbeing of the animals.

In another experiment $1 \times 10^6$ cells per animal were injected into syngenic mice (Balb/C). After the primary tumour reached a size of 4 cm3 the tumours were surgically removed so that there was no tumour tissue remaining at the site of the operation. The mice were then further monitored and after their death the presence of lung metastases was investigated.

In a last experiment to demonstrate the ability of the CT26− and CT26−TβRII-dn cells to colonise the lung from the circulation, 5,000 and 50,000 cells of both types were injected i.v. into the caudal vein of syngenic Balb/C mice. After their death the mice were then examined as before for the presence of lung metastases.

d) Antibodies

Rabbit antisera against cytokeratin have been described by Reichmann et al., 1992. Rabbit antiserum and monoclonal rat antibodies against E-Cadherin were prepared as described by Kemler, 1993 and the relevant literature cited therein (Kemler, 1993). Rabbit antiserum which recognises neomycin phosphotransferase was prepared by bacterially expressing neomycin phosphotransferase, purifying it and injecting it into rabbits. After a reasonable time rabbit serum was obtained and used neat for immune staining. The monoclonal mouse antibody against vimentin V3B (Boehringer Mannheim), the monoclonal rat antibody against ZO-1 (Chemicon), the monoclonal mouse antibody against TGFβ 1–3 (Genzyme), the TGFβ 2,3-antibody (Genzyme), the polyclonal antiserum against activated TGFβ (Promega), the TGFβ-neutralising polyclonal rabbit antibody (R&D) as well as the monoclonal TGFβ-antibody (Genzyme) were obtained commercially.

e) Sections and Immunofluorescence

In order to obtain the optimum biological activity from RNA and proteins in the excised tissues and collagen gels, the tumour material and the cell structures containing collagen type I gels were flash-frozen immediately after isolation in liquid nitrogen. Before freezing the collagen gels were soaked for 2 min in medium containing 5% DMSO in order to prevent cell damage as a result of the formation of ice crystals. Cells grown on plastic or frozen sections prepared from tumours or collagen gels were fixed and made pervious for 15 min at −20° C. using acetone/methanol, mixed in the ratio 1/1, air-dried and stored at 4° C. The incubation with the first antibody was carried out for 1 h at 37° C. in PBS which normally contained gelatin, BSA and Tween 20 (0.2% each), in order to prevent non-specific antibody staining. The cells or sections were then covered in Moviol 1–88 (Hoechst) and examined with a Zeiss Axiophot fluorescence microscopy. The photographs were prepared either conventionally or by computer-aided methods using a Kaf 1400 CCD camera (Photometric) and the Adobe Photoshop 3.0 picture developing program.

In order to detect cytokeratin, vimentin and TGFβ in human tumour tissue serial sections of frozen material were analysed immunohistochemically by the ABC method. The immunohistochemical analysis was carried out as described by Heider et al., 1995. Anti-cytokeratin (clone MNF 116; DAKO, Denmark), anti-vimentin (clone V9; DAKO, Denmark) and a mixture of anti-TGFβ1 and TGFβ2 (Santa Cruz, Calif.) were used as the primary antibodies. The results of the staining were evaluated with a Zeiss Axioskop microscope.

For the simultaneous detection of vimentin and cytokeratin in tissue sections, double fluorescence analysis was carried out. Anti-vimentin (clone V9; DAKO, Denmark) and an anti-cytokeratin rabbit serum were used as primary antibodies, whilst Cy3-coupled anti-mouse IgG or FITC-coupled anti-rabbit IgG antibody were used as secondary antibodies. The fluorescence was evaluated using a Zeiss Axiophot 2 microscope with the aid of a Leica Quantimed Q500 picture analysis system.

f) RNA in situ Hybridisation

For the RNA in situ hybridisation the frozen sections were fixed and extracted as described by Oft et al., 1993. For this the sections were fixed in 4% paraformaldehyde in PBS, washed twice in PBS, prehybridised for 2 hours and hybridised overnight with the appropriate $S^{35}$-labelled riboprobe at 52° C. in 50% formamide, 0.6 M NaCl. After washing under stringent conditions ($T_m$−20° C.) the sections were immersed in Kodak NTB liquid emulsion and illuminated for 2 weeks. The slides with the sections were counter-stained with haematoxylin/eosin and analysed under light and dark field illumination using a Zeiss Axiophot microscopes.

In order to prepare the $S^{35}$-labelled riboprobes the hTGFβ1-cDNA (R&D) and the cDNA for neomycin phosphotransferase, excised from a suitable retroviral vector (Redmond et al., 1988), were cloned into the $T_3$–$T_7$ expression plasmids (Bluescript II KS Stratagene) and transcribed in vitro, in the presence of $S^{35}$-UTP for the antisense riboprobe and for the sense control probe.

The non-radioactive in situ hybridisation for TGFβ in sections of human tumour tissue was carried out by means of digoxygenin-labelled probes. The probe (hTGFβ1, see previous paragraph) was labelled by means of the DIG-RNA Labelling Kit made by Boehringer Mannheim according to the manufacturer's instructions. For the hybridisation frozen sections (5–7 μm) were fixed in 4% paraformaldehyde for 10 min, washed twice in PBS and subsequently acetylated for 10 min in 0.5% acetic anhydride. After washing twice in PBS the sections were dehydrated in an ascending alcohol series, air-dried and subsequently incubated for 30 min at 52° C. in a damp chamber. The hybridisation with the probe was carried out for 4 to 6 h at 52° C. in a damp chamber. After hybridisation the slides were washed for 2×10 min in 2×SSC at 52° C. and subsequently the bound probe was made visible by means of anti-digoxygenin antibody according to the instructions of Boehringer Mannheim. The slides were briefly counter-stained with haematoxylin, covered and evaluated with a Zeiss Axioskop microscope.

g) Electron Microscopy

The cells grown in the collagen gels were pre-fixed for 10 min in 3% paraformaldehyde in 0.2 M HEPES pH 7.3 at room temperature. The cells were further fixed on ice in 8% paraformaldehyde in 0.2 M HEPES pH 7.3 for 30–60 min. For the immunocytochemistry the samples were dewatered in ethanol at ever lower temperatures, embedded in Lowicryl HM20 or K4M and polymerised at −35° C. by means of UV-light (Schwarz et al., 1993). To investigate the ultrastructure the cells were post-fixed with 1% osmium tetraoxide in PBS pH 7.2 for 1 h on ice, stained with 1% aqueous uranyl acetate for 1 hour, dewatered in ethanol at room temperature and finally embedded in Epon. For the immunocytochemistry ultrathin sections were stuck to cover glasses (Schwarz, 1994). After the blocking of non-specific antibody binding sites with 0.5% bovine serum albumin and 0.2% gelatin in PBS the sections were incubated with rabbit-anti-Catenin-antibodies and subsequently with Cy3-labelled goat-anti-rabbit IgG. The labelled sections were stained with 4',6-diamino-2-phenylindole (DAPI), to make the nuclei visible under immunofluorescence microscopy.

h) Southern Blot Analysis

Total DNA of cells or tumour material was isolated and processed using standard methods (Maniatis et al., 1982). DNA, extracted from cells before injection, from freshly excised tumour tissue (day 15 after the injection) and from tumour tissue which had been recultivated in vitro in the presence of G418 for 5 days, was digested with the restriction enzyme EcoRI (which cuts the retroviral vector only once), blotted onto a Gene Screen Membrane and hybridised with the cDNAs, coding either for the neomycin-phosphotransferase or for the v-Ha-ras gene.

i) Northern Blot Analysis

The Northern Blot analysis was carried out as described by Chomczynski and Sacchi, 1987; as well as by Reichmann et al., 1992. Total RNA (10 μg per track) was placed on denaturing, formaldehyde-containing gels, blotted onto Gene Screen Membranes and hybridised with the entire coding region of hTGFβ1-cDNA (R&D), which has sufficient homology with mTGFβ1, 2 and 3 to recognise all three mouse-TGFβ-isoforms.

j) Semi-quantitative PCR

Total RNA from cells, grown on plastic, in collagen gels or from tumours, was isolated and processed for the semi-quantitative PCR. A TGFβ1-specific fragment was amplified by means of RT-PCR under semi-quantitative conditions, using -actin primers as the internal control, as described by Leonard et al., 1993. For this the DNA was denatured at 94° C. for 1 min, the primers were annealed at 65° C. for 1 min, and the polymerase reactions were continued at 72° C. for 1 min. The amplification was continued for 20 and 30 cycles. The TGFβ1-specific primers TGGACCGCAA CAACGC-CATC TATCCAGAAAA CC (forward) and TGGAGCT-GAA GCAATAGTTG GTATCCAGGG CT (reverse) (Clontech Inc.) were used. The results of the PCR were quantitatively evaluated on an Image Quant Phospho-Imager. The values were standardised on the control product (-actin) and subsequently correlated with the value from control-3T3-fibroblast.

TGFβ1 was detected in tumour tissue by means of RT-PCR as briefly described (Heider et al., 1996). The TGF β1-specific oligonucleotide GCCCTGGACACCAACTATT GCTTC was used as 5'-primer and the TGF β1-specific oligonucleotide TGCTCCACCTTGGGCTTGC was used as 3'-primer. The amplification products were separated on a 2% ethidium bromide-containing agarose gel and evaluated under UV-light by means of a video camera (MWG Biotech).

k) Transient Transfection of a PAI-1-promoter-reporter Gene Construct

A PAI-1 promoter-reporter construct (reporter gene was luciferase; 3TP-lux, Wrana et al., 1992) was transfected by lipofectamine transfection (Gibco) according to the manufacturer's instructions into CT26 cells or CT26-TβRII-dn cells. 8 hours after transfection TGFβ1 was added for 24 hours, while the controls were left without TGFβ. Then cell lysates were prepared and the luciferase activity was measured in a Berthold Clinilumat as described by Wrana et al., 1992. In order to determine the transfection efficiency all the cells were cotransfected with an CMV-β-Gal reporter gene construct and the luciferase activities obtained were standardised by the β-Gal fluorescence intensity and by the protein concentration of the extract (Bradford).

l) Quantitative Determination of Soluble TGFβ by means of ELISA Assay

In order to determine the TGFβ concentrations by means of ELISA assay, EpH4, polarised EpRas and fibroblastoid EpRas cells, isolated from tumours or converted in vitro with TGFβ, were washed five times with PBS to remove exogenous TGFβ and subsequently grown for 48 hours in serum-free DMEM. Then the cell culture supernatants were collected and the TGFβ1 concentrations were determined by means of a commercially obtainable ELISA-Kit (Promega; G1230) according to the manufacturer's instructions.

m) Immunoblots

In order to determine TGFβ1 in the tissue culture supernatants, 2 ml serum-free cell supernatants were concentrated by ultrafiltration (Centricon 10, Amicon) down to a final volume of 0.1 ml. The concentrated supernatants were mixed with 5-times concentrated SDS-PAGE probe buffer (without mercaptoethanol) and analysed by SDS-PAGE under non-reducing conditions. Equal aliquots of protein (50 µg) were subjected to SDS-polyacrylamide gel electrophoresis; the immunoblot analysis was carried out as described by Hayman et al., 1993.

n) Chicken Embryo Heart Invasion Assay

This assay was carried out as described by Behrens et al., 1993. In order to be able to distinguish invasive donor cells clearly from chicken heart cells, the test cells were charged with a vital fluorescent dye before examination. For this the cells were incubated for 1 hour in a glucose-containing Hanks saline solution containing 10 mM 5,6-carboxy-2',7'-dichlorofluorescein diacetate-succinimidyl ester (Molecular Probes) and $0.2 \times 10^{-6}$ M Pluronic F127. In this way the fluorescent dye is covalently bound to intracellular proteins without affecting the viability or behaviour of the cells, determined by various differentiation and proliferation assays. The labelled cells were grown for 24 hours at high density, scraped off the plastic dish and brought into contact with pre-cultivated heart fragments of 9 day old chicken embryos on the surface of a soft agar layer. After 7 days' cultivation the fragments with the adhering cells were collected, flash-frozen in liquid nitrogen, frozen sections were prepared, fixed in methanol/acetone and the fluorescent cells were determined by epifluorescence microscopy (Axiophot, Zeiss).

o) Implantation of TGFβ1-charged Slow Release Pellets in Mice

In order to expose Ras-transformed breast epithelial cells to activated TGFβ1 very early in tumour development, TGFβ1 -charged Slow Release Elvax Pellets and either EpRas-epithelial cells or normal EpH4H cells were coinjected subcutaneously in mice. For control purposes pellets, charged only with BSA, were coinjected. The pellets were prepared and charged according to the manufacturer's instructions.

Example 1

Ras Expressing Polarised Epithelial Cells Undergo EF Conversion During Tumour Development The tests carried out were suggested by the observation that Ras-transformed mouse-breast epithelial cells (EpRas cells) exhibit two completely different cell phenotypes. When they are grown on plastic substrates, these cells grow as ordered, dome-forming monolayers (hemicysts), indicating a polarised epithelial phenotype (FIG. 1A, B). After being injected into mice, however, these same polarised cells formed tumours consisting of depolarised spindle-shaped cells with the capacity for invasive growth (FIG. 1A, C). In order to obtain further findings as to the mechanisms underlying this phenotypical plasticity, the cell conversion observed was examined in detail by a combination of in vivo and in vitro experimental preparations. The cell clone EpH4 was used for this, which is derived from a well characterised mouse-breast epithelial cell line (Reichmann et al., 1989; Reichmann et al., 1992; Strange et al., 1991). These cells exhibit a stable polarised epithelial phenotype (Reichmann et al., 1994).

When suitable retroviral vectors were used tumorigenic subclones of EpH4 were formed by stable expression of the v-Ha-Ras-oncogene. After the expression of v-Ha-Ras as been confirmed by Western Blot analysis, cells from seven clones (referred to as EpRas-clones) were injected subcutaneously or directly into the mammary glands of Balb/c-mice. Tumours were formed regularly which were palpable 5–7 days after the injection of the cells.

The phenotype of these converted tumour cells was compared with that of the original differentiated clones: before the injection all seven EpRas-clones displayed the expected polarised phenotype (FIG. 1B and Table 1). By contrast, when cells were excised from the tumours and recultivated in the presence of G418, only converted, fibroblastoid cells were obtained (FIG. 1C, Table 1). Although they still expressed cytokeratin to a certain extent, these cells had lost many of their epithelial properties and acquired the expression of fibroblastic markers (FIG. 1C, Table 1). In order to demonstrate that the tumour-cells came from the EpH4 donor cells originally injected, as well as to show that no rearrangement or reintegration of the Ras-containing retrovirus had taken place during the tumorigenesis and subsequent cultivation in vitro, the integration pattern of the retroviral constructs was determined by Southern Blot analysis. For this EpRas cells before injection, cells from a 15-day tumour and re-isolated cells from a 30-day tumour were analysed. When using probes with specificity for the neomycin resistance gene or the ras gene identical integration patterns were obtained in all three cell types (FIG. 1D).

The conversion of EpRas cells into fibroblastoid cells during tumour formation in mice is shown in FIG. 1.

FIG. 1A shows the principle of the strategy which was used in order to study EFC of Ras cells (7 different v-Ha-Ras expressing cell clones were used) in vivo.

FIG. 1B: Before injection cells of the clone Ep5 exhibited the formation of domes on plastic and staining both on E-cadherin (FITC, green fluorescence, appearing dark in the black and white representations), and also on cytokeratin (Texas-Red, red fluorescence). The common staining of both proteins on the periphery of the cell should be noted (yellow staining).

FIG. 1C: Ep5 cells, isolated from a tumour 28 days after the cell injection. These cells display a fibroblastoid appearance and express cytokeratin but no E-cadherin.

FIG. 1D: Southern Blot analysis. The EpRas-clone (Ep5), before injection (Ep5, plastic), removed from the tumour (Ep5, tumour), removed from the tumour and recultivated for 5 days in G418 (Ep5, ex tumour), shows the same retroviral integration pattern (detected with a neomycin-phosphotransferase (NPT) probe).

Example 2

Timing of EF Conversion and Behaviour of Animal Donor and Receiver Cells During Tumorigenesis in vivo Next, the stage of tumour development at which the subcutaneously injected epithelial EpRas cells undergo EF conversion, if at all, was examined. Three days after the injection the EpRas cells formed clearly defined nodules in which the cells expressed characteristic cytokeratins, but no vimentin (FIG. 2A). These epithelial cell nodules were already encapsulated by stroma cells (FIG. 2A). Cells which grew out of these microtumours on plastic and in the presence of G418, still demonstrated epithelial properties. Seven days after the injection it was observed that the solid cell aggregation of Ep-Ras cells was beginning to break up at the edge of the tumour and the epithelial cells were mixed with vimentin-positive stroma cells at the periphery of the microtumours (by inward migration of the stroma cells or outward migration of the donor cells). At this moment the donor cells still displayed epithelial properties, both in the tumour and also after isolation and in vitro cultivation in G418.

15 days after the injection three different cell types could be distinguished (FIG. 2C): about 20% of the tumour cells were green stained vimentin-positive stromal cells. Another 20% expressed only cytokeratins, indicating EpRas cells which have retained the epithelial phenotype. The majority (50–60%) of the tumour mass, however, consisted of cells which co-expressed cytokeratin and vimentin. These cells are in all probability converted or converting EpRas cells. Both the epithelial and also the converted fibroblastoid cells were also obtained after G418 selection. Finally, the epithelial part could no longer be detected, either in situ, or on plastic, in five week old, fully developed tumours. By contrast parental EpH4 cells never formed tumours. When they were injected subcutaneously, the EpH4 cells developed into layers of epithelial cells which sometimes formed lumina and cytokeratins, but expressed no vimentin (FIG. 2D). After a fairly long time these cells necrotised and were reabsorbed by the surrounding stroma.

In order to clearly identify the originally injected donor cells at the three different tumour stages, in situ hybridisation was carried out on the neomycin resistance gene. These experiments showed that all cytokeratin expressing cells originated from donor cells. The frequency of donor cells relative to the stroma cells of the receiver animals increased with the size of the tumour and was greatest in fully developed tumours (FIGS. 2E, F, G, H).

All in all, these data show that both the Ras expressing cells and also the epithelial control cells in vivo initially have an epithelial phenotype. As the development of the Ras cell tumours progresses the Ras-transformed cells progressively acquire fibroblastoid properties. By contrast the non-tumorigenic parental cells stably retain their epithelial properties until they die.

Figure 2:
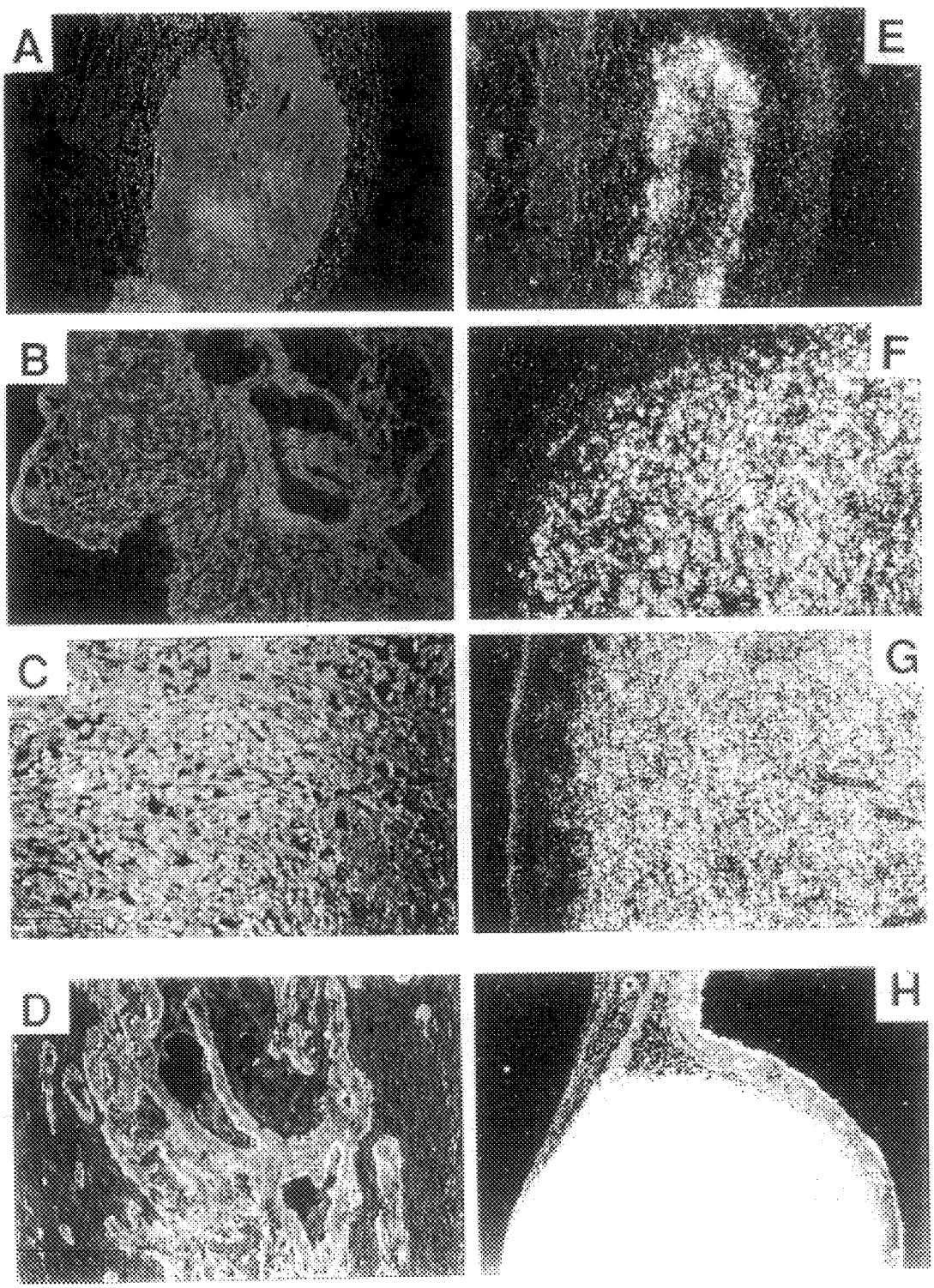

FIG. 2 shows the timing of the epithelial/mesenchymal conversion (EFC) during tumour development and demonstrates the fate of donor and receiver cells during this process.

Differently treated frozen sections of EpRas-tumours (clone Ep2) are shown, which were prepared on day 3 (FIGS. 2A, E), on day 7 (FIGS. 2B, F), on day 15 (FIGS. 2C, G) and on day 28 (FIG. 2H) after the injection. The cell structures formed by non-tumorigenic EpH4 cells 15 days after the injection are shown in FIG. 2D. The sections were examined by immunofluorescence (FIGS. 2A–D) and in situ hybridisation (FIGS. 2E–H). The sections were double-stained with antibodies against a 46 kDa cytokeratin (Texas-Red, red fluorescence) and vimentin (FITC, green fluorescence). It was noted that in 3-day-old tumours the injected epithelial cells (stained red) and the mesenchymal cells of the host (stained green) are clearly separate. In 15-day-old tumours large numbers of cytokeratin/vimentin-double-positive cells are visible (yellow-stained cells). These cells have undergone EFC. RNA-in situ hybridisation using a neomycin-phosphotransferase-probe confirms the donor origin of the tumour cells and shows the increasing density of the tumour cells after EFC (FIGS. 2E–H).

Example 3

Figure 3:
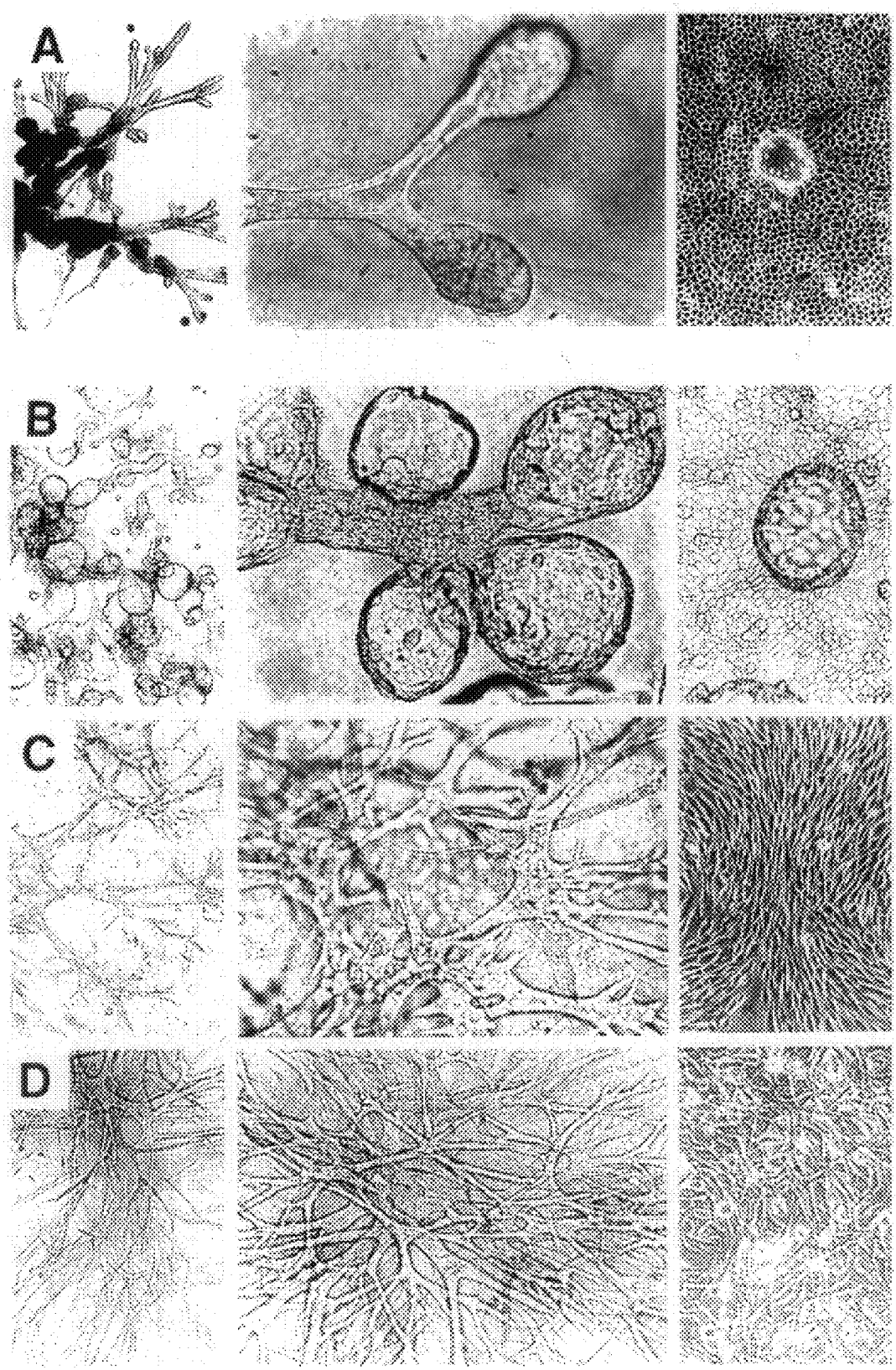

TGFβ1 Induces in vitro EF Conversion in Ras Expressing, but not in Normal Epithelial Cells In order to identify the mechanism underlying the EF conversion, an experimental system was used with which EF conversion can be induced in vitro under defined and physiologically relevant conditions. For this purpose normal EpH4 cells or Ras-transformed subclones of these cells (Ep-Ras clones) were grown in reconstituted collagen type I gels, using serum-free medium. These conditions made it possible to add defined polypeptide growth factors and hormones which are known to be involved in the modulation of the epithelial phenotype. In gels of this kind, normal EpH4 cells developed into organ-like gland channels (tubuli) which frequently terminated in club-shaped hollow swellings. These structures looked very similar to the end buds of the developing mammary gland which are formed by primary breast epithelial cells both in collagen gels and also in vivo (FIG. 3A). These structures could be induced to produce milk proteins efficiently by the addition of lactogenic hormones. When these cells were isolated from the gel and grown on tissue culture plastic, they formed the expected regular epithelial monolayers, which formed recognisable domes, an indication that these cells are able to polarise efficiently (FIG. 3, right-hand Table).

Surprisingly, the EpRas-clones in these serum-free collagen gels also exhibited considerable lumen formation. The lumina were visible as early as 2–3 days after seeding. Thereafter more than 95% of these structures developed relatively large cystic cavities (FIG. 3B, left-hand and centre Table) which resembled the alveoli of the fully developed milk-producing mammary gland. On plastic these cells in turn formed regular epithelial monolayers with domes, and thus exhibited the same epithelial properties as the non-tumorigenic starting cells (FIG. 3B, right-hand Table).

The same EpRas cells behaved completely differently, however, when they were cultivated in 10% foetal calf serum (FCS). Under these conditions they formed elongated, multi-cellular and invasively growing strings of cells which never showed any lumen formation. These strings consisted of non-polarised cells which had lost many epithelial properties (FIG. 3C and FIG. 4) and behave in a strikingly similar manner to the ex vivo fibroblastoid tumour cells. These findings indicated that a factor contained in the FCS, co-operating with the activated Ha-Ras-oncoprotein, brings about the conversion of the epithelial EpRas cells into fibroblastoid cells.

In order to identify this factor or these factors, a number of growth factors (TGFβ, heregulin, scatter-factor/hepatocyte growth factor, acidic and basic FGF, PDGF and TGFβ1) were added to the Ras-transformed cells grown in collagen gels. Surprisingly, TGFβ1 was the only factor which showed striking and long-lasting effects on EpRas cells. When TGFβ1 was added, these cells grew into elongated, branching strings of cells similar to those induced by FCS. On tissue culture plastic these cells exhibited a clear, fibroblastoid phenotype (FIG. 3D). In pH4 control cells and other non-tumorigenic breast epithelial-cell clones, by contrast, TGFβ1 was not able to induce EF conversion.

In order to examine whether the activity in the serum which promotes EF conversion is actually TGFβ1, cultures which contained 5t FCS were incubated with TGFβ1 neutralising antibodies. Under these conditions EpRas cells in turn formed cystic cavities very similar to those shown in FIG. 3B. Thus, the cell-converting activity present in FCS was identified as TGFβ1 and it was shown that TGFβ1 is the only or at least the predominant activity in FCS which can induce EF conversion.

Other ultrastructure and immunohistochemical analyses showed that most of the cystic structures consisted of a monolayer of polarised cells (FIG. 4A). These cells abundantly formed microvilli at their apical domain (the one facing the lumen), indicating a polarised organisation of the cells (FIG. 4A). Moreover, different types of epithelial-cell-typical cell-to-cell contact structures, i.e. tight junctions, characterised by the protein ZO-1, desmosomes (FIG. 4A) and the cell adhesion molecule E-cadherin typical of so-called "adherens junctions" (FIG. 4B) could be detected by their typical lateral or basolateral positions. Similarly, the protein β-catenin associated with E-cadherin showed basolateral localisation in most of the cells (FIG. 4C).

By contrast, the string-like cell structures induced by TGFβ1 consisted of loosely adhering spindle-shaped cells (FIG. 4D, inset picture). None of the epithelial marker proteins and ultrastructurally recognisable contact structures mentioned could be detected (FIG. 4D and Table 1), with the exception of a low, non-polarised expression of E-cadherin (FIG. 4E). The expression of β-catenin was greatly reduced and located chiefly in the cytoplasm (FIG. 4F). Moreover, these cells expressed the expected mesenchymal markers (Table 1).

These results show that Ras-transformed mouse-breast epithelial cells exhibit exceptional plasticity in the phenotype, which ranges from epithelially polarised cells organised into ordered epithelia to fibroblastoid, migratory and invasively growing cells.

FIG. 3 shows the destruction of lumen formation and epithelial polarity by serum and TGFβ1.

Non-tumorigenic EpH4 cells (FIG. 3A) or tumorigenic EpRas cells (clone Ep5, FIGS. 3B–D) were grown in collagen type I matrices. The macroscopically visible structures were photographed 8 days after plating out at low and high magnifications (left-hand and middle Table). Cells isolated from the gels and grown on tissue culture plastic are shown in the right-hand Tables.

FIG. 3A: Ep4H cells form channels and swellings resembling end-buds in serum-free collagen gels. On plastic these cells formed a regular epithelial monolayer and domes (hemicysts).

FIG. 3B: In serum-free collagen gels, wide channels and alveoli-like cysts are formed by EpRas cells.

FIG. 3C: Addition of 10% FCS causes the cells to form invasively growing irregular strings of cells without a lumen. On plastic these cells are similar to fibroblasts and are spindle-shaped.

FIG. 3D: TGFβ1 on its own (5 ng/ml) causes EpRas cells to grow into invasive strings of cells similar to those induced by FCS.

Figure 4:
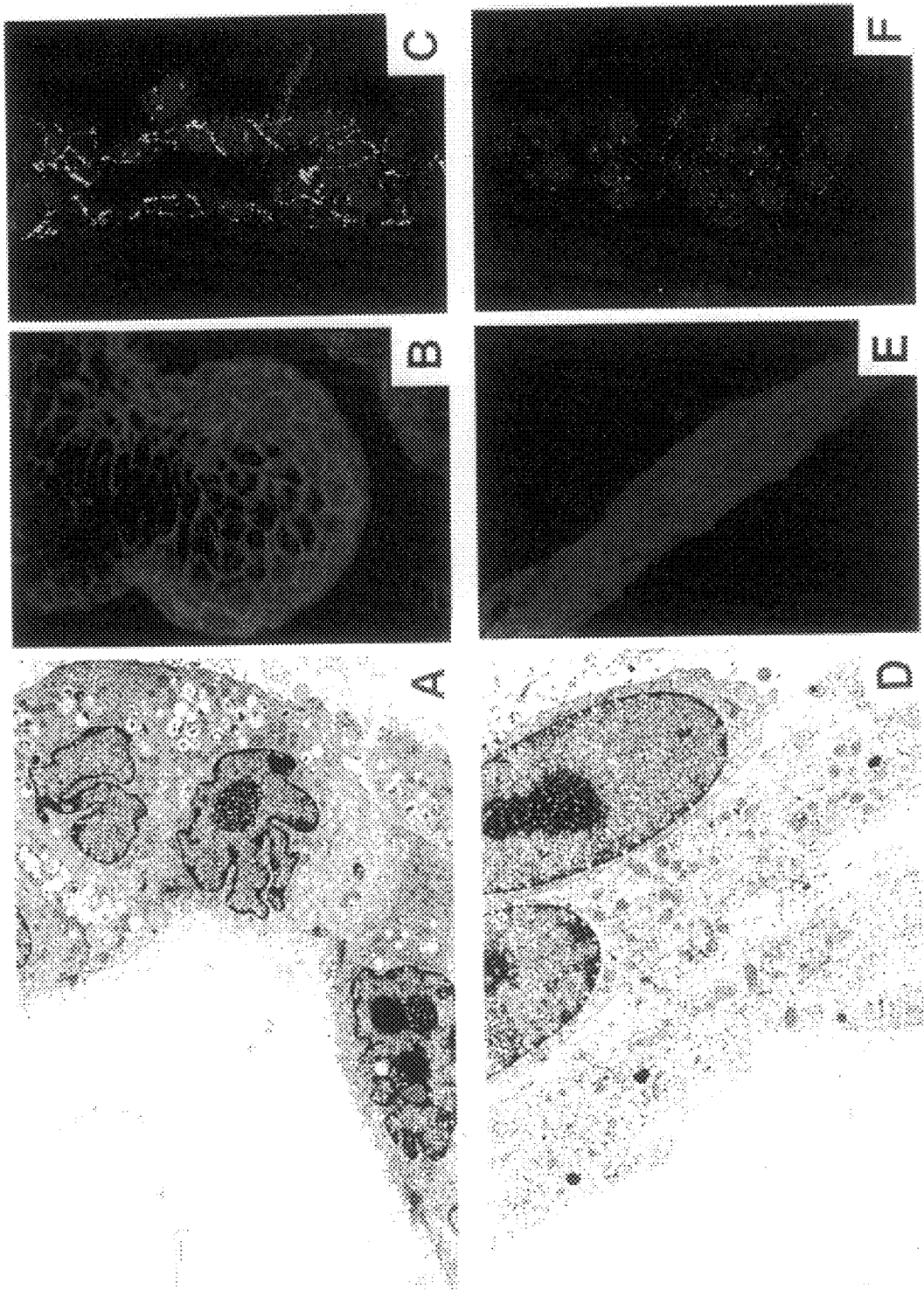

FIG. 4 shows the breakdown of epithelial cell polarity in Ras-transformed breast epithelial cells after incubation with TGFβ1.

Alveoli-like cysts, formed by EpRas cells (clone Ep6) in serum-free collagen gels (FIGS. 4A–C), and disordered strings of cells, formed by the same cells after treatment with TGFβ1 (FIGS. 4D–F), were analysed for their epithelial organisation and formation of cell polarity. Sections through individual structures were photographed at high or low magnifications(inset pictures).

FIG. 4A: Transmission electron microscopy showed that the cysts obtained in the absence of TGFβ1 consisted of a monolayer of morphologically polarised cells which finally comprise the microvilli in their apical domain, facing the lumen (FIG. 4D). The inset picture shows a monolayer cyst of this kind at low magnification. By contrast, the strings of cells induced in the presence of TGFβ1 consist of loosely adhering cells without microvilli, desmosomes or tight junctions.

FIGS. 4B, E: frozen sections through an alveolar cyst which were immunostained with an antibody against the cell adhesion molecule E-cadherin, showed clear basolateral localisation of the E-cadherins in most of the cells. In the TGFβ1-induced strings of cells, E-cadherin is reduced in its expression and is expressed over the entire surface of the fibroblastoid cells.

FIGS. 4C, F: These show Lowicryl sections through structures similar to those shown in FIGS. 4B and E, immunostained with an anti-β-catenin-antibody. The basolateral expression of β-catenin in most of the cells of the cyst (FIG. 4C) and the significantly reduced β-catenin expression which is now localised predominantly in the cytoplasm should be noted (FIG. 4F).

Example 4
Fibroblastoid EpRas Cells are Invasive

EpRas cells which had undergone EFC showed signs of invasive behaviour in collagen gels. In order to obtain definitive proof of this invasive property, the chicken embryo heart invasion assays were used, the relevance of which to in vivo metastasisation has already been documented in detail (Mareel et al., 1979; Mareel, 1983). In this assay the migration of cells into embryo heart fragments was examined (FIG. 5A). In order to identify the penetrating cells clearly, they were labelled with a fluorescent dye (carboxy-dichloro-fluorescein-diacetate). During the incubation period of seven days no parental EpH4 cells migrated into the chicken heart tissue (FIGS. 5A, B). In three different, fully-polarised Ep-Ras-clones, only a vanishingly small proportion of the cells were capable of migrating into the heart tissue (FIG. 5C). The few cells which migrated in were strongly stained with a vimentin antibody, but not with an anti-E-cadherin antibody. This confirms their conversion into a fibroblastoid phenotype, which is not surprising as the co-cultures contained serum. In contrast to the epithelial cells the fibroblastoid cells which had been obtained from tumours ("ex-Tu cells"), or cells which had been induced to EFC by the use of TGFβ1 in vitro, migrated into the heart muscle tissue in large numbers and relatively fast (FIG. 5D).

These results show that EpRas cells are highly invasive after undergoing EFC, while non-converted epithelial cells exhibit only slight invasivity.

Figure 5:
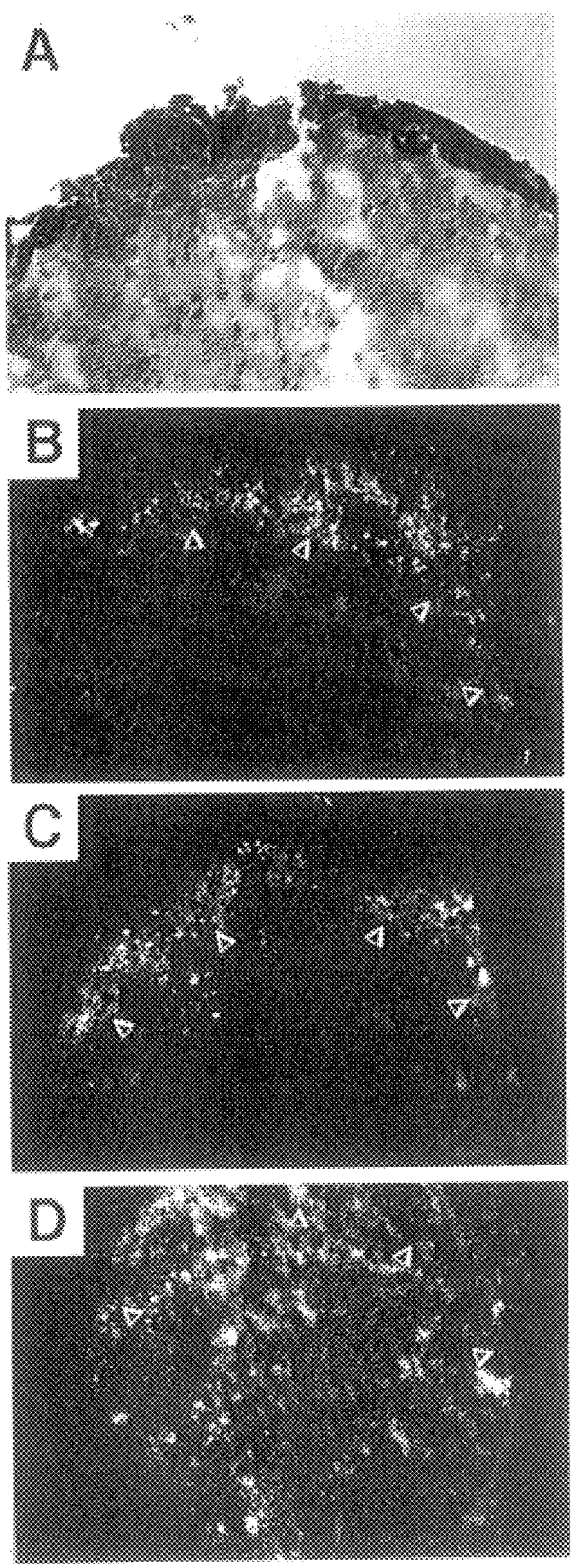

FIG. 5 shows the high invasivity of fibroblastoid EpRas cells in the chicken embryo heart invasion assay.

In vivo fluorescence-labelled cells were co-cultivated with chicken embryo heart fragments in order to test their invasivity, and sections through the fragments were examined histologically 7 days later. The non-tumorigenic epithelial starting cells (EpH4 cells) did not migrate into the heart fragments (FIGS. 5A, B), and non-converted epithelial EpRas cells showed only slight invasivity (FIG. 5C). By contrast the converted, fibroblastoid cells obtained after TGFβ1 treatment were capable of migrating efficiently into the heart fragments (FIG. 5D).

Example 5
TGFβ1 Maintains the Fibroblastoid Phenotype of Converted EpRas Cells through an Autocrine Loop After it had been shown that TGFβ1 converts Ras-transformed epithelial cells into fibroblastoid cells, the question arose as to whether TGFβ1 is also involved in maintaining this phenotype. A possible explanation for the relative stability of the fibroblastoid phenotype (e.g. in cultures on plastic) was the autocrine production of fairly large amounts of TGFβ1 by the converted cells themselves. In order to settle this question, fibroblastoid EpRas cells were cultivated in extremely low concentrations in 1% FCS (in order to minimise the TGFβ1-concentration in the medium). Under these conditions individual cells grow into clearly spatially separated clones. As shown in FIGS. 6A and B, the clones obtained soon after plating out and consisting initially of a few cells had a fibroblastoid morphology at first. As the number of cell clones increased, the cells in the overwhelming majority of the clones gradually changed into cells with an epithelial phenotype (FIGS. 6A to D). This reversion was substantially complete 10 days after plating out (FIG. 6D).

In order to suppress the effects of autocrinally produced TGFβ1 completely and thereby definitively demonstrate that TGFβ1 is really necessary for maintaining the EF conversion, fibroblastoid cells (ex-tumour cells) isolated from a tumour were grown in the presence or absence of TGFβ1 neutralising antibodies in collagen gels. In the absence of the antibodies the fibroblastoid tumour cells formed the expected thin, invasively growing strings of cells (FIG. 6E). The same cells, however, no longer grew invasively and developed into cystic structures consisting of an epithelial monolayer when they were treated for eight days with the neutralising antibodies (FIG. 6F).

Finally the amounts of TGFβ1-mRNA expressed in the cells and the TGFβ1 -protein released into the culture medium were determined. Three different EpRas clones as well as the parental EpH4 clone were grown for five days in collagen gels. When they were treated with 5 ng/ml TGFβ1, the EpRas-clones underwent EFC, while the similarly treated, non-transformed EpH4 cells retained their epithelial phenotype. Analysis of these cells by semi-quantitative PCR (FIG. 7A) or by means of immunoblot (FIG. 7B) showed that the fibroblastoid cells induced by TGFβ1 produced quantities of TGFβ1-mRNA which were comparable with those of control fibroblasts (FIG. 7A). This also applied to EpRas cells which had changed into fibroblastoid cells in tumours. By contrast, parental EpH4 cells and epithelial EpRas cells produced no or only small amounts of TGFβ1-mRNA (FIG. 7A). At the protein level essentially the same results were obtained when serum-free culture supernatants were analysed by ELISA and Western blot (FIG. 7B).

Figure 6:
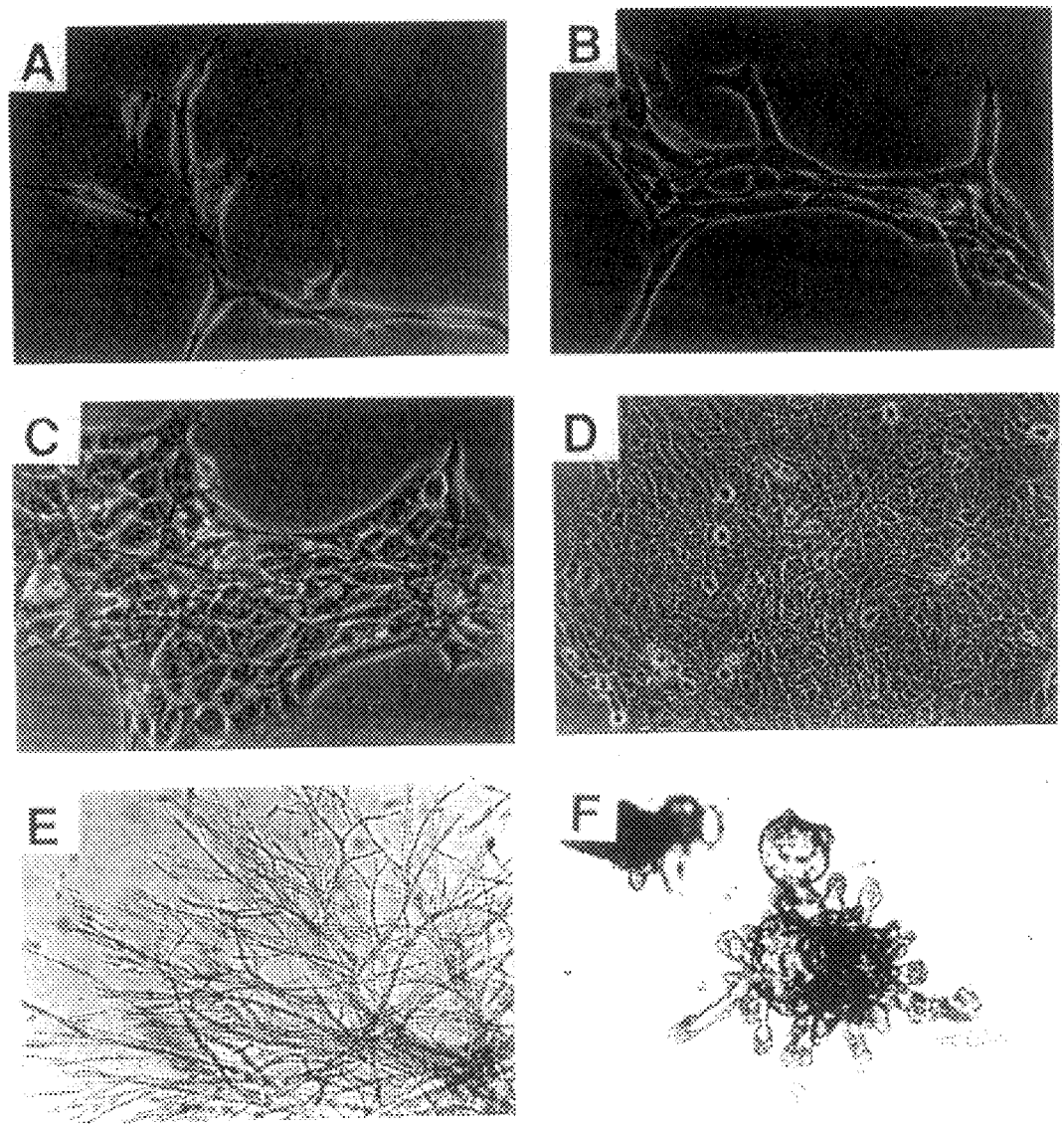

FIG. 6 shows that TGFβ1 maintains the fibroblastoid phenotype of converted EpRas cells through an autocrine loop.

FIGS. 6A–D: clones from fibroblastoid cells isolated from a tumour (ex-tumour cells) gradually change into clones consisting of epithelial cells. In order to produce the clones 500 cells per 100 mm dish were sown in medium containing 1% FCS. The medium was changed daily in order to dilute any autocrine factors. The same typical cell clone was photographed on day 1 (A), day 3 (B), day 5 (C) and day 10 (D) after plating out. The gradual transformation of the fibroblastoid cells into cells with an epithelial morphology is clearly visible.

FIGS. 6E, F: fibroblastoid EpRas cells isolated from a tumour were selected for 5 days in G418 (in order to eliminate any cells originating from the receiver animal) and subsequently seeded into serum-free collagen gels. This was carried out either in the absence (E) or in the presence (F) of TGFβ1 neutralising antibodies. It can be seen that in the presence of a TGFβ1 neutralising antibody the tumour cells develop into lumen-shaped structures, whilst in the absence of the antibody they form the expected disordered strings of cells.

Figure 7:
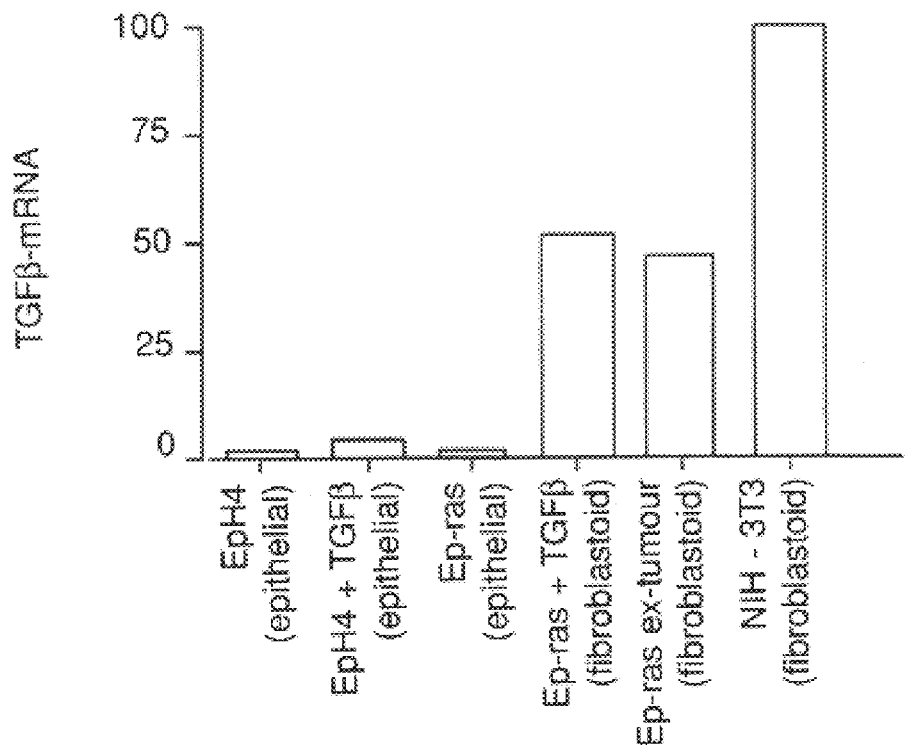
Figure 7:
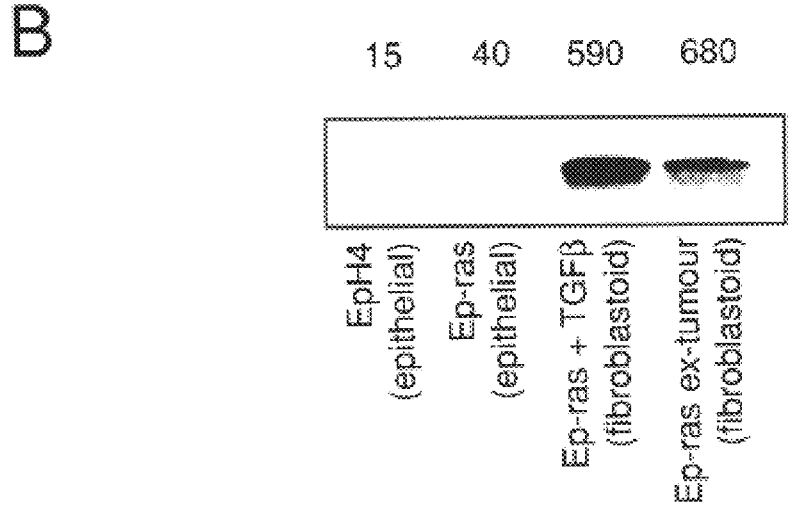

FIG. 7 shows that converted EpRas cells produce high concentrations of TGFβ1.

FIG. 7A: RNA from non-converted (epithelial) and converted (fibroblastoid) EpRas cells (clone Ep5) and also from non-tumorigenic EpH4 cells and NIH-3T3-fibroblasts (ATCC CRL 1658) was used for semi-quantitative PCR analysis. The significant increase in TGFβ1-mRNA in the fibroblastoid cells should be noted. The TGFβ1 expression is recorded as a percentage of the values obtained with NIH-3T3 cells.

FIG. 7B: Similar results were obtained when the TGFβ1-concentrations in cell culture supernatants were analysed by Western Blot and ELISA (the numbers above the Western-Blot gel traces show the quantities of TGFβ1 in ng TGFβ1/ml determined in the ELISA). The data shown in FIG. 7B were confirmed with two other EpRas-clones (Ep2 and Ep6).

In all, these results indicate the major role of TGFβ1 not only in inducing EFC, but also in maintaining the fibroblastoid phenotype.

Example 6

Finally tests were carried out to determine whether TGFβ1 is actually expressed in EpRas tumours and whether TGFβ1 added experimentally in vivo can also bring about EFC and invasivity of the cells. Tumours growing from injected EpRas cells were examined for the expression of TGFβ1, 4 and 15 days after the injection of the cells, by RNA in situ hybridisation and immunohistochemistry. Just 4 days after the injection of the cells increased concentrations of TGFβ1-mRNA were detected at the outer edge of the nodes formed by the EpRas cells (FIG. 8A). The co-expression of TGFβ1 and neomycin phosphotransferase (NPT, which is expressed exclusively by the Ras-transformed donor cells) shown up by double immunofluorescence showed that the great majority of the donor cells (characterised by the red staining on NPT) produced no TGFβ1 (green staining) at this stage of the tumour development. On the other hand, cells of the surrounding tumour stroma originating from the receiver animal and non-epithelial in origin were distinctly positive for TGFβ1 (FIG. 8B). By contrast tumours which had been removed 28 days after the injection showed a relatively high and uniform expression of TGFβ1-mRNA over the entire tumour region (FIG. 8C). In these tumours it was found that the injected EpRas cells themselves produced TGFβ1 because they could be stained with antibodies against both NPT and TGFβ1; they displayed a yellow staining (FIG. 8D). Remarkably, most of the cells which produced TGFβ1 showed a reduced expression of cytokeratin, whereas the majority of the cells with high cytokeratin expression could not be stained with antibodies against TGFβ1. This is further proof that the converted cells are actually whose which also produce TGFβ in the animal at advanced stages of the tumour.

These results show that host cells which surround the tumour tissue are able to initiate cell conversion. The converted tumour cells in turn themselves produce TGFβ, thus speeding up cell conversion and subsequently the invasion processes.

In order to prove this directly, Slow Release Pellets charged with recombinant human TGFβ1 were applied close to the injected EpRas cells. The same TGFβ1 pellets, combined with non-tumorigenic EpH4 cells, were used as controls. Surprisingly, EpRas cells located close to a TGFβ1 pellet were converted into irregularly shaped cells just 4 days after the injection and exhibited extensive migration into the surrounding host tissue. Surprisingly, even at this early stage, many of these cells were positive for vimentin (FIG. 8F). By contrast, identical EpRas cells which had been injected in the absence of exogenous TGFβ1 formed smooth homogeneous nodes of vimentin-negative cells forming close cell contacts (FIG. 8E). As expected, TGFβ1 pellets located close to EpH4 cells could not noticeably influence the phenotype of these non-tumorigenic cells. These in vivo data conform to the results obtained in vitro and lead one to conclude that TGFβ1 has a key role in regulating the plasticity and invasivity of tumour cells.

Figure 8:
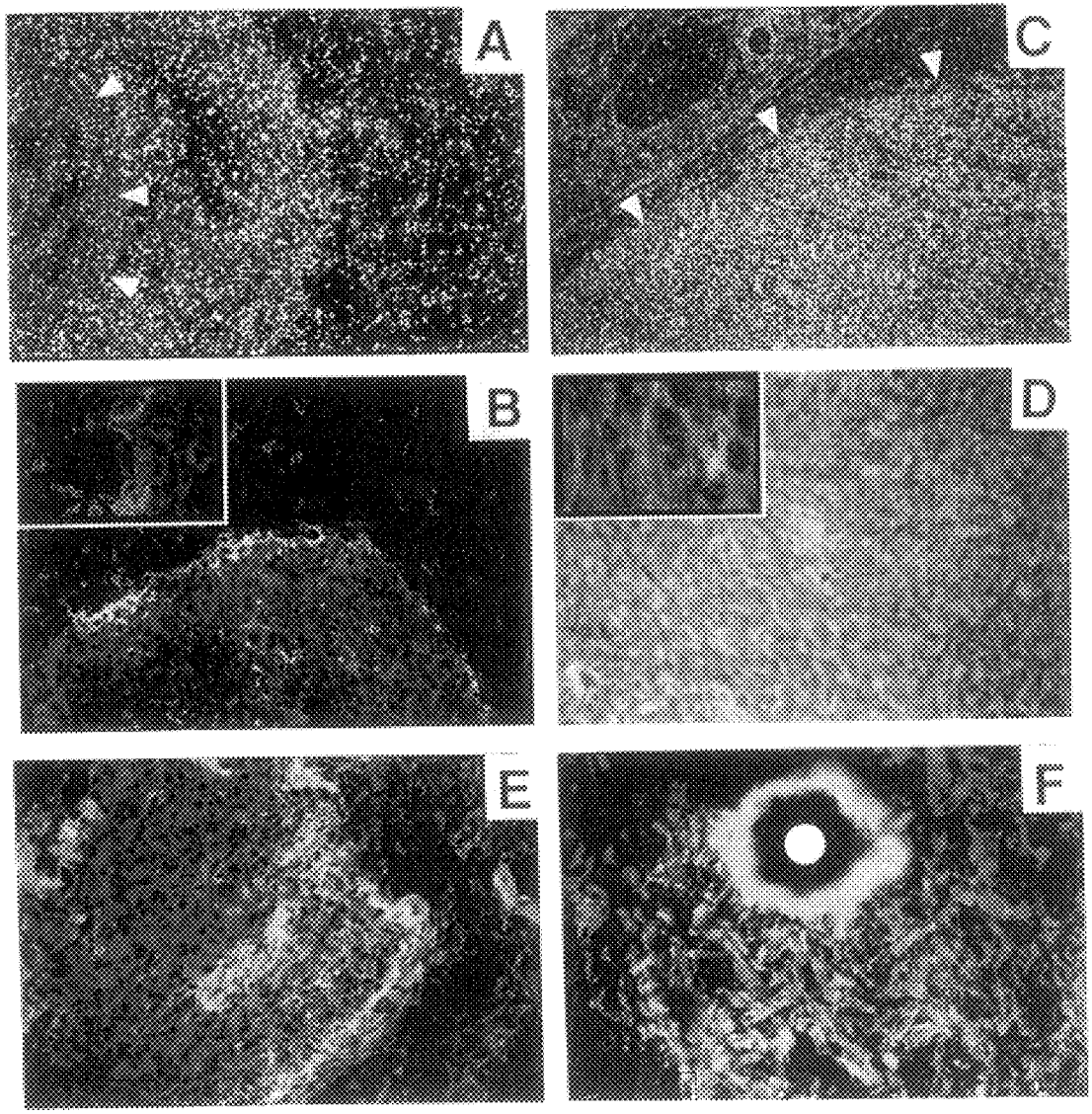

FIG. 8 shows how TGFβ1 in experimentally induced tumours triggers the transition from the epithelial to the fibroblastoid state as well as the invasivity of the cells:

FIGS. 8A–D: frozen sections of tumour stages on day 4 (A, B) and day 15 (C, D). The RNA in situ hybridisation shows that on day 4 the TGFβ1 expression is taking place in the outer periphery of the tumour (A), but on day 15 (C) it is occurring throughout the tumour. Arrow heads indicate the boundary between tumour and surrounding stroma.

FIGS. 8B, D: frozen sections were stained with an anti-TGFβ1-antibody (green fluorescence) and an anti-neomycin phosphotransferase-antibody, which recognises the donor cells (red fluorescence). The smaller diagrams show extracts at higher magnifications. It should be pointed out that at early stages of the tumour TGFβ1 is produced exclusively by the stroma around the tumour (B). By contrast, in 15 day-old tumours, TGFβ is also expressed in many donor cells within the tumour tissue (D, yellow fluorescence).

FIGS. 8E, F: Epithelial EpRas cells were injected subcutaneously into nude mice without (E) or together with 3-Elvax Slow Release Pellets charged with recombinant (active) TGFβ1 (F). Frozen sections obtained from 4 day old tumours were double-stained with antibodies against cytokeratin (red) and vimentin (green). What is noticeable is the dramatic migration of cells into the surrounding tissue induced in the vicinity of the TGFβ1 -releasing pellets (white circle).

Example 7
Effect of TGFβ1 on Normal Breast Epithelial Cells: Control of Milk Duct Morphogenesis by Regulating Cell Growth, Cell Polarisation and Apoptosis Since the TGFβ-super-family of polypeptide factors is involved primarily in morphogenetic processes during embryo development, the role of TGFβ1 in normal mammary gland development was also examined within the scope of the present invention. For this purpose normal breast epithelial cells of the cell line EpH4 were sown in serum-free collagen gels. Unlike in the experiments in Example 3, the serum needed during sowing for the collagen gel to set and washed out one day later was specially selected for a low content of TGFβ1. Under these conditions the in vitro organogenesis was completely inhibited, and no tubular structures were formed (FIG. 10A). When low concentrations of TGFβ1 (0.1 ng/ml) were added, the cells were able to proliferate and form atypical structures which generally lacked lumina (FIG. 10B). Further investigations showed, however, that these structures expressed ZO-1, a tight-junction protein, on the inside. Thus, these structures bore some resemblance to the end buds of the developing mammary gland.

By contrast, higher concentrations of TGFβ1 (>0.25 ng/ml), caused the normal epithelial cells to stop growing and die off by programmed cell death (apoptosis) (FIG. 5C). This is an important difference between the normal epithelial cells and the Ha-Ras-containing cells. Whereas the latter are not induced into apoptosis and undergo EFC without exception even concentrations of TGFβ1 which are 20 times higher (5 ng/ml), the TGFβ1 concentration which regulates the morphogenetic processes in normal breast epithelial cells is strictly laid down. Possibly, aberrant morphogenesis caused by excessively high TGFβ1 concentrations is prevented by the fact that growth inhibition and apoptosis are induced in the cells instead.

The fact that it was not possible to induce fully differentiated tubular structures consisting of polarised cells with low concentrations of TGFβ1, might be due to suboptimal culture conditions. On the other hand the complete organogenesis of tubular structures might depend on TGFβ1 only being present during certain phases of the organ development. In order to examine this, the cells were treated with 0.1 ng/ml TGFβ1, as described above, until structures had formed, then TGFβ1 was washed out of the collagen gel. Surprisingly, the atypical structures then reorganised themselves without lumina and formed well-shaped tubular structures with typical lumina (FIG. 10D, transient TGFβ1). These results lead one to conclude (i) that TGFβ1 is absolutely necessary for in vitro organogenesis, (ii) that the concentration is critical, with higher concentrations leading to apoptosis, and (iii) that TGFβ1 only has to act on the cells during certain phases of the organ development. This normal function of TGFβ1 in the development of breast epithelial cells is completely changed in the Ras-transformed cells, with TGFβ here causing an extremely abnormal form of tissue reorganisation which causes a transition from the epithelial to the fibroblastoid state (EFC) over a wide range of concentrations.

The next step was then to look for indications that TGFβ1, analogously to these in vitro findings, also controls the morphogenesis and programmed cell death of mammary gland epithelia in vivo. For this, mammary glands in mice during puberty were subjected to histological analysis combined with in situ hybridisation using a probe against TGFβ1.

During this phase the virginal mammary glands grow into the surrounding fatty tissue (fat pad). Growth, differentiation and morphogenesis of the mammary gland produced start from a structure which is termed the end bud and contains undifferentiated, not yet fully polarised epithelial cells.

Sections through the end bud (where the proliferation and subsequent organogenesis, such as e.g. the branching off of the milk ducts, take place) were compared with sections through fully differentiated ducts of the gland (cf. the schematic diagram in FIG. 11, centre). Whereas TGFβ1 is produced in the mesenchymal stroma which surrounds the growing end buds (FIG. 11, left-hand Table), no such production of TGFβ1 was seen in the stroma cells surrounding an already differentiated gland duct (right-hand Table). These findings largely correspond to the in vitro data, in which temporary, pulsed treatment of the breast epithelial cells with TGFβ1 was necessary for the tubular morphogenesis.

Similarly, there was an indication that TGFβ also regulates the programmed cell death (apoptosis) of breast epithelial cells in vivo. During reversion of the mammary gland after ablactation the alveolar cells undergo mass apoptosis, whereas the cells in the gland ducts survive and are retained. New growth of the mammary glands during another pregnancy starts from these cells. In order to examine the possible involvement of TGFβ1 in this process, frozen sections through the dying alveolar zone of a mammary gland and through an adjacent gland duct region were prepared three days after the end of lactation (FIG. 12, representation in the centre). In the region which had just undergone apoptosis, the mesenchymal cells surrounding the dying alveoli expressed high concentrations of TGFβ1 (FIG. 12, left-hand Table), while the mesenchymal cells surrounding the surviving ductal structures expressed no TGFβ1 (FIG. 12, right-hand Tables). In both cases it is probable that crosstalk takes place between the epithelial cells and the TGFβ1 production induced in the mesenchyme.

Figure 10:
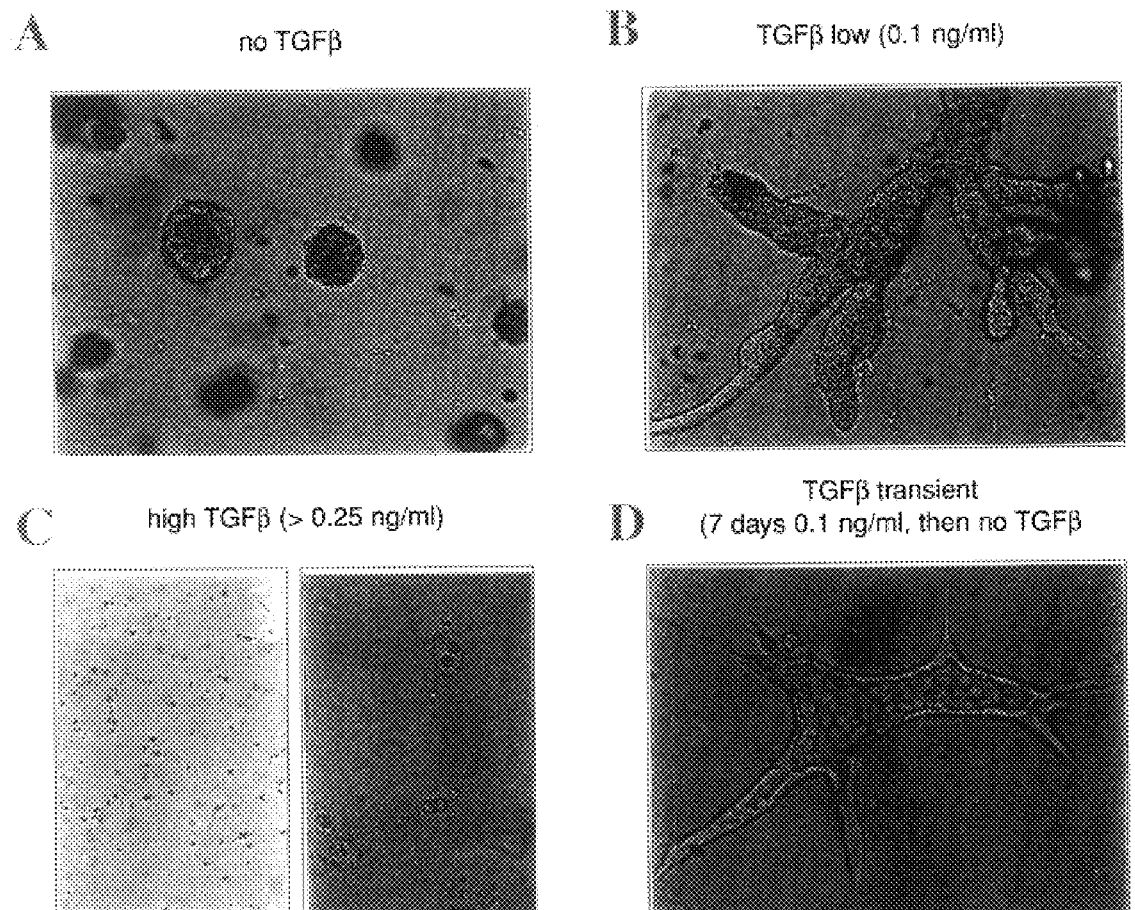

FIG. 10 shows that a low concentration of TGFβ1 controls the in vitro morphogenesis of normal mammary gland epithelial cells, particularly when the factor is given transiently. Higher concentrations of TGFβ1 cause apoptosis in the same cells.

Normal EpRas cells were sown in collagen gels, using a foetal calf serum selected for a particularly low TGFβ1 content during the sowing. Under these conditions the cells do not form any tubular structures (FIG. 10A). In the presence of 0.1 ng/ml of TGFβ1 the cells form branched structures, but these lack lumina (FIG. 10B). If the TGFβ1 is removed from cultures with such structures on day 7 by washing, the cells form distinct hollow structures (FIG. 10D). Higher concentrations of TGFβ1 cause cell death (apoptosis, FIG. 10C, lower magnification on the left, higher magnification on the right).

FIG. 11: shows the in vivo expression of TGFβ1 during the formation of the normal mammary gland during puberty (day 25).

Frozen sections through end buds of a virginal mammary gland (left-hand panels) or through already formed gland ducts (right-hand panels) were prepared as shown in the central diagram. Successive sections in a series of sections were subjected to RNA in situ hybridisation for TGFβ1 mRNA (upper panels) or histologically stained. It is clearly apparent that mesenchymal cells which surround the end bud strongly express TGFβ1 (left-hand panels), whereas in cells which surround the differentiated gland ducts, there is no detectable TGFβ1 expression.

FIG. 12 shows the in vivo expression of TGFβ1 in the breakdown of the fully developed mammary gland after ablactation.

Young mice were taken away from their nursing mothers, thus triggering the reversion of the fully developed mammary gland. 3 days later frozen sections were taken through the dying areas of the mammary gland (left-hand panels) as well as through the gland ducts unaffected by the apoptosis (right-hand panels) (cf. the diagram in the centre of the Figure) The sections were then examined for TGFβ1 expression, as described in the legend to FIG. 11. Whereas TGFβ1 producing cells are clearly detectable in the area surrounding the dying alveoli (left-hand panels) there are none around the surviving gland ducts.

Example 8

Coexpression of Vimentin and Cytokeratins in Human Tumour Tissue. Expression of TGFβ by Human Primary Tumours In the previous Examples a well characterised cell model, namely Ras-transformed breast epithelial cells from the mouse, was used. It was thus very important to assess how far the results obtained with this model system as to the activity of the TGFβ receptor on the phenotypical plasticity and invasivity of epithelial tumour cells applies to human carcinomas. For this purpose 31 kidney cell carcinomas and 64 breast tumours of different degrees of malignancy were examined by immunohistochemistry. Firstly, corresponding histological sections through such tumours were double-labelled with antibodies against general epithelial cytokeratins and antibodies against the mesenchymal marker vimentin. Tumour cells which coexpress both markers have probably undergone EFC. Secondly, adjacent sections from the breast tumours were labelled with antibodies against human TGFβ1 and TGFβ2, in order to find out whether the tumour cells also produce TGFβ.

As shown in the following Table, 74% of the kidney cell carcinomas expressed both cytokeratin and also vimentin in the degenerate epithelial tumour cells. As expected, the fibroblastoid cells of the tumour stroma expressed only vimentin, but no cytokeratin. In the breast carcinoma cells the percentage of tumours which coexpressed cytokeratin and vimentin was smaller, namely between 24 and 27%.

The results of the histochemical analysis of the same breast tumours for the expression of TGFβ were even clearer. Here, all the tumours tested showed clear staining of the tumour cells for TGFβ (Table). The tumour stroma was stained more weakly or not at all for most of the tumours. The specificity of the staining was also clear from the staining of normal tissue; on the skin, for example, as expected, only the basal cell layers of the keratinocytes were positive. As is also shown in the Table, the results of the histochemical staining were also fully confirmed by in-situ hybridisation for TGFβ as well as by RT-PCR.

These results show that for a significant proportion of the human tumours investigated, there were clear indications, in two ways, that the tumour cells corresponding to the model in FIG. 9 had both undergone EFC and had also highly regulated the production of TGFβ.

The Table shows that human kidney cell and breast carcinomas coexpress cytokeratin and vimentin. This is a clear indication that EFC has taken place. Similarly, all the tumours investigated produce TGFβ.

The upper part of Table (A) shows the results of the staining for cytokeratin and vimentin on frozen sections of the types of tumour specified. The lower part (B) shows the results of staining for TGFβ on sections through the same breast tumours. Footnotes give the results of control experiments for the TGFβ expression (by RT-PCR) and the expression of TGFβ in the tumour stroma.

A Coexpression of Vimentin and Basal Cytokeratins

| Type of tumour | Subtype | Number of tumours analysed | Number of tumours with vim./cytok. coexpr. |
|---|---|---|---|
| kidney cell carcinomas (RCC) | | 31 | 23/31 (74%) |
| breast tumours | | 64 | 18/64 (28%) |
| | fibroadenoma (FA) | 3 | 2/3 (66%) |
| | invasive ductal ca. (IDC) | 34 | 8/34 (24%) |
| | invasive lobular ca. (ILC) | 26 | 7/26 (27%) |
| | inv. ductal-lobular ca. (IDLC) | 1 | 1/1 |

B Expression of TGFβ-1/2

| Type of tumour | Subtype | Antibody staining | In situ hybridisation |
|---|---|---|---|
| breast tumours | fibroadenoma (FA) | 3/3 (100%) | |
| | invasive ductal ca. (IDC) | 33/33 (100%) | 13/13 (100%) |
| | invasive lobular ca. (ILC) | 23/23 (100%) | 9/9 (100%) |
| | inv. ductal-lobular ca. (IDLC) | 1/1 (100%) | |

Additional Analyses
1. RT-PCR of IDC and ILC: 11 cases positive with Ab are also positive with RT-PCR
2. expression in the tumour stroma: antibody: in 35/61 cases, slight staining In situ hybridisation: in 3/22 cases Example 9
Neutralising Antibodies Against TGFβ Prevent Invasive Growth of Human Tumour Cell Lines in Collagen Gel In Example 8 histochemical examination of sections through tumour tissue provided evidence that the hypotheses reached with the model system regarding TGFβ-induced EFC and the subsequent autocrine production of TGFβ also apply to many human tumours. In order to obtain more direct evidence of this, experiments were caried out to determine whether human tumour cells which grow invasively in the collagen gel can be converted into non-invasively growing cells by the administration of TGFβ-neutralising antibodies. The kidney carcinoma cell line MZ 1795 and the nasopharyngeal-carcinoma line KB were-used. The cells of both lines grew in collagen gels containing 5% FCS without TGFβ-antibodies or after the addition of TGFβ to form networks and strings of fibroblastoid cells (FIG. 13, right-hand panels). In the presence of TGFβ neutralising antibodies (cf. Example 5, FIG. 6), on the other hand, the cells formed compact clumps without any reference to invasive growth (FIG. 13, left-hand panels).

FIG. 13 shows that TGFβ neutralising antibodies prevent the invasive growth of human tumour cell lines in collagen gel.

MZ 1795 cells and KB cells were sown in serum-free collagen gels to which was added either 2% serum or 5 ng/ml of TGFβ (+TGFβ, right-hand panels) or to which a mixture of different antibodies against TGFβ (−TGFβ, left-hand panels; cf. Example 5, FIG. 6) was added. After 10 days microphotographs of the cells in the collagen gels were prepared. Whereas both the MZ 1795 cells (top panels, higher magnification, bottom panels; summaries, lower magnification) and also the KB cells (lower panels) grow en masse into the collagen gel, when TGFβ is present (right-hand panels), the same cells in the presence of TGFβ-neutralising antibodies form compact clumps without any cells growing out (left-hand panels).

Example 10
The Expression of a Dominant-negative TGFβ Receptor Prevents EF Conversion and Slows Down Tumour Growth of Ras-transformed Breast Epithelial Cells The most direct proof of the presumed mechanism of activity (proof of principle) for the activity of TGFβ receptor inhibitors in inhibiting tumour progression consists in demonstrating this activity directly in the tumour-bearing animal. This was not possible within the scope of these Examples with the TGFβ-neutralising antibodies used in Vitro, as the large amounts of antibody. needed for in vivo tests of this kind were not available. An alternative approach was therefore adopted.

There is a "kinase-dead" mutant of the human TGFβ receptor type II (TβRII-dn), which also acts as a dominant-negative receptor (i.e. one that switches off the function of the wild-type receptors). A cDNA of this TβRII-dn was expressed in Ras-transformed EpH4 cells (Ep-Ras) with the aid of retroviral vectors. The clones obtained grew very slowly and required medium with a high (20%) serum content, in order to be capable of expansion. After injection into nude mice these cells had formed either no tumours at all or only small tumours (FIG. 14, top) up to the time when the mice injected with control cells (Ep-Ras) had to be killed because of their excessively large tumours.

The tumour cells were isolated from the slowest-growing Ep-Ras-TβRII-dn tumour as well as from a control tumour induced by Ep-Ras cells and cultivated (cf. Example 1). Whilst the cells of the control tumour exhibited the expected fibroblastoid morphology (bottom of FIG. 14, left-hand Table) the tumour cells isolated from the slow-growing Ep-Ras–TβRII-dn exhibited a distinctly epitheloid morphology (bottom of FIG. 14, right-hand Table). This shows that the EF conversion occurring during tumour formation by Ep-Ras cells is inhibited by the expression of TβRII-dn and that this leads to a slowing down of tumour growth.

FIG. 14 shows that TβRII-dn expressing, Ras-transformed breast epithelial cells (Ep-Ras–TβRII-dn) exhibit slower growth in the animal and the cells isolated from these tumours have not undergone any EF conversion.

Four different clones of Ep-Ras–TβRII-dn cells as well as an Ep-Ras control clone were each injected subcutaneously into 3 nude mice (1×10$^6$ cells per animal). After 3 weeks the tumours were excised and weighed. The diagram in the upper part of FIG. 14 gives the mean values of the tumour weights obtained. The tumour cells from an Ep-Ras–TβRII-dn tumour, obtained from the slowest tumour-forming Ep-Ras–TβRII-dn clone, and an Ep-Ras control tumour were cultured, selected in G418 (cf. Example 1) and photographed after 10 days under phase contrast. The bottom left-hand panel shows the fibroblastoid cells which have grown from the Ep-Ras tumour, whereas the right-hand panel shows the epitheloid cells which have grown from the Ep-Ras-TβRII-dn tumour.

Example 11
Expression of TβRII-dn in Fibroblastoid, Highly Metastasising Colon Carcinoma Cells (CT26): Inhibition of the Invasive Growth of These Cells in vitro, Delaying of Tumour Formation and Inhibition of the Formation of Lung Metastases in Mice Once it was shown that the dominant-negative TGFβ receptor (TβRII-dn) could prevent both the EF conversion of EpRas cells and also dramatically slowed down the tumour growth of these cells, it was useful to examine the efficacy of this TβRII-dn in tumour cells which had already stably undergone EF conversion and were already highly metastatic. The mouse colon carcinoma cell line CT26, an established mouse model for lung metastasis formation from a primary tumour (Brattain et al. 1980), was chosen. These cells were infected with an TβRII-dn-expressing retrovirus (cf. Example 10), TβRII-dn-expressing clones were selected and various clones were subjected to analysis in vitro and in vivo.

Two types of TβRII-dn-expressing CT-26 clones (CT26–TβRII-dn) were obtained. The first type showed a distinctly epithelial, but still abnormal morphology on plastic and expressed small amounts of the epithelial markers E-cadherin and ZO-1. The second type of clone, on the other hand, on plastic formed lawns of cells with epithelial morphology which even formed hemicysts (domes). As expected, this second type of clone showed high lateral expression of the epithelial markers E-cadherin and ZO-1. Control CT26 cells which were infected with a retrovirus without an insert exhibited the expected fibroblastoid morphology on plastic and no expression of epithelial markers. It was thus shown that TβRII-dn is capable of converting the fibroblastoid CT26 cells into epithelial cells in vitro and thus effecting FE conversion.

Next, representative CT26–TβRII-dn clones of both types as well as CT26 control cells are sown in collagen gels with 5% FCS. FIG. 16 shows that the control cells grow into the expected enormous strings and networks of fibroblastoid cells (FIG. 15, top half of the picture, left-hand panels). By contrast the CT26–TβRII-dn clones of type 1 formed compact clumps with only a few single cells growing out (FIG. 15, top half of the picture, middle panels) whereas the CT26–TβRII-dn clones of type 2 only grew into tiny, compact groups of cells (FIG. 15, top half of the picture, right-hand panels). This showed that TβRII-dn prevents the invasive growth of CT26 cells in the collagen gel.

Then the same cell types were tested by the chicken heart invasion assay (cf. Example 4, FIG. 5). Whereas control-CT26 cells, as expected, grew very invasively in this assay (FIG. 16, bottom half of the picture, left-hand panel), the CT26–TβRII-dn clones of types 1 and 2 in this test were only slightly invasive or not invasive at all (FIG. 15, bottom half of the picture, middle and right-hand Table.)

These experiments show that TβRII-dn causes an FE conversion of CT26 cells and totally inhibits their invasive growth in two assay systems. It was therefore of great interest to examine the behaviour of these cells in the animal. Therefore, CT26 control cells as well as 6 CT26–TβRII-dn-clones of types 1 and 2 were injected into nude mice. Whereas the control animals had to be killed after 2–3 weeks on account of their excessively large tumours, the tumour growth in mice was delayed with CT26–TβRII-dn-clones of type 1 by about 3–4 weeks, whereas in mice with CT26–TβRII-dn-clones of type 2 it was delayed by 6–10 weeks or totally inhibited for 24 weeks (end of experiment) (3 animals, data not shown in the FIG.). These results show that TβRII-dn can also dramatically delay the growth of CT26-primary tumours in some cases.

Next, the ability of the CT26–TβRII-dn cells to colonise the lung from a primary tumour and form metastases was examined. As shown in FIG. 17 (diagram in bottom half), mice were injected with CT26 control cells (3 mice) or 7 different CT26–TβRII-dn-clones (type 1 and type 2, 3 mice per clone) and the growth of palpable tumours was awaited. After a certain tumour volume (4 cm$^3$) had been reached the primary tumour was excised so that no tumour cells remained at the injection site. The mice thus treated were examined for lung metastases after their death.

All control animals (3 mice) bearing CT26-tumours died after 2–4 weeks of lung metastases (FIG. 16, diagram in top half of picture, dotted line). By contrast the formation of lung metastases could not be detected in any of the animals injected with CT26–TβRII-dn-clones even after 18 weeks (FIG. 16, diagram in top half of picture, black lines). 5 animals in which there was a local recurrence of the primary tumour were not included in the evaluation.

These data clearly show that TβRII-dn fully inhibits the metastasisation of CT26-primary tumours. Finally, the stage of metastasisation which is inhibited by TβRII-dn was checked. It is possible that only the migration of the CT26 cells out of the primary tumour into the blood vessels is inhibited. However, the settling of the cells out of the circulation and in the lungs might also be affected. The latter is important because, for example, more tumour cells might enter the circulation of a person when a tumour was surgically removed. In order to test this, different quantities of CT26 control cells and a number of CT26–TβRII-dn clones of type 2 were injected intravenously into mice (3 animals per cell type). The animals were then examined for lung metastases after death. Preliminary tests showed that a mere 500 CT26 cells per animal are sufficient to form lung metastases in this way. Therefore 10 and 100 times the quantity of both cell types were injected. FIG. 17 shows that after 14 days (50,000 cells) and 28 days (5,000 cells) the CT26 control cells had formed lung metastases in all the animals. By contrast, even after 40 days, all the animals injected with CT26–TβRII-dn clones were still alive and had not yet formed any lung metastases, as confirmed on individual mice killed at this stage. Thus TβRII-dn can also prevent CT26 cells already in the circulation from settling in the lungs.

FIG. 15 shows that TβRII-dn inhibits both the invasive growth of CT26 cells in the collagen gel, and also suppresses the invasivity of the same cells in the chicken heart invasivity test.

For the first test (collagen gel assay, top half of the picture) CT26 control cells (CT26, left-hand panels) and a CT26–TβRII-dn clone of type I (middle panels) and type 2 (right-hand panels) were sown in collagen gels with 5% serum and after 10 days microphotographs of the collagen gels were prepared. The gels were photographed at two different magnifications (lower magnification, top panels, higher magnification, lower panels). Whereas the CT26 control cells grew into large network-shaped and string-like structures, consisting of spindle-shaped, fibroblastoid cells (left-hand panels), the CT26–TβRII-dn type 1 cells formed compact clumps of cells with very few cells growing into the gel (middle panels). The CT26–TβRII-dn clones of type 2 form only tiny compact cell groups without any ability to grow into the collagen gel (right-hand panels).

For the chicken heart invasion assay (bottom half of the picture) the test cells were charged with a fluorescent vital dye, brought into contact with chicken heart fragments and examined histologically after 7 days (cf. methods and Example 4). The control cells migrated efficiently into the chicken heart fragment (left-hand Table, light-coloured groups of cells and strings on the side of the boundary between test cells and chicken heart fragment indicated by a dotted line labelled H). By contrast type 1 clones migrated only slightly into the chicken heart tissue (middle panel, cf. the few light-coloured cells in the area marked H), while the CT26–TβRII-dn cells of type 2 did not grow invasively at all (all the light-coloured cells remained outside the chicken heart fragments H (dotted line).

FIG. 16 shows that the expression of TβRII-dn in CT26 cells blocks their ability to form lung metastases from a primary tumour.

The progress of the experiments is shown diagrammatically in the bottom half of the picture. 7 different CT26–TβRII-dn clones (type 1 and 2, CT26+TβRII-dn) as well as CT26 control cells were used in the test. Syngenic Balb-C mice (3 per cell type) were injected with $1 \times 10^6$ cells per animal and the growth of tumours was awaited. After the primary tumours reached a size of 4 cm$^3$ they were surgically removed and after they had died the mice were examined for lung metastases. The results are shown in the diagram (top half of the picture). Whereas the 3 control animals died within 4 weeks of lung metastases (dotted line), all the animals treated with CT26–TβRII-dn cells were still alive and free from lung metastases after 18 months (black lines). In the case of the line ending after 14 weeks (top diagram) the primary tumour reached the critical size so late that 18 weeks had not passed by the time the test ended.

FIG. 18 shows that TβRII-dn in CT26 cells also inhibits their ability to settle in the lungs from the bloodstream and form metastases there.

The diagram in the top part of the Figure shows the progress of the experiment. Syngenic Balb-C mice (3 per cell type and cell quantity) were injected intravenously (into the caudal vein) with CT26 control cells and several CT26–TβRII-dn clones. The Figure shows that all three mice treated with 5,000 or 50,000 control cells (CT26) had died of lung metastases after 28 or 14 days (+), whereas all the animals injected with CT26–TβRII-dn clones were still alive free from lung metastases after 40 days (−)

Example 12

The activated TGFβ receptor activates the transient transcription of a PAI-1-promoter-reporter gene construct, a process which is inhibited by TβRII-dn.

With a view to discoveing TGFβ-(receptor) inhibitors by means of cellular assay in a High Throughput screening (HTS) process a test cell is prepared as follows: a PAI-1-promoter-reporter gene construct is stably expressed in a suitable cell (Ep-Ras or CT26). At the same time the human TGFβ receptor chain (e.g. TβRII) selected for the screening is expressed in this cell. By contrast, an unrelated receptor which also induces PAI-1 transcription, e.g. an FGF receptor, is expressed in control cells in addition to the PAI-1-reporter construct.

A prerequisite for the development of a test cell line of this kind is that the TGFβ-induced PAI-I expression (suppressed by the inhibitor) is correlated with the tumour formation or metastasisation of the corresponding cells in transient transfection tests. In order to check this, CT26 control cells and 5 CT26–TβRII-dn clones already tested in mice (cf. Example 11, FIG. 16) were transfected with the 3TP-lux PAI-1-reporter gene construct (Wrana et al., 1992), stimulated with TGFβ or left untreated and tested for PAI-1 expression (measurement of luciferase activity). As positive and negative controls a constitutively active TGFβR chain (TβRI(T204D); Wrana et al. 1994) as well as TβRII-dn DNA together with the PAI-1 reporter construct were co-transfected into untreated CT26 cells. FIG. 18 shows that untreated CT26 cells (CT26 controls) without TGFβ treatment have a basal activity which corresponds to that of the negative controls (cotransfection of TβRII-dn). In the same control cells TGFβ activates the reporter gene transcription to levels which are attained in the positive controls by cotransfection of a constitutively active TGFβ receptor.

Different TβRII-dn expressing CT26 clones behaved differently in this test (FIG. 18, CT26–TβRII-dn 1–5). In two clones (CT26–TβRII-dn 3 and 4) the luciferase activity achieved after TGFβ stimulation was below or at the levels found in the negative controls, irrespective of whether the cells were tested before injection or after isolation from the very slow-growing tumour. In the three remaining clones (in which the tumours induced grew faster) the luciferase activity was at the level of the negative controls only before injection into the animal, after isolation from the tumour intermediate levels or even activities comparable to those in the positive controls were found (FIG. 18). It can be assumed that in the latter clones there was selection for cells in which the expression of TβRII-dn was down-regulated. This assumption was supported by the fact that renewed selection of the cells from the tumour in puromycin again killed off many cells and the surviving puromycin-resistant cells no longer exhibited increased PAI-1 transcription after TGFβ stimulation. The results of these experiments show that the tumour formation/metastasisation in the animal is clearly correlated with the TGFβ-activatability of a PAI-1 promoter-reporter gene construct.

FIG. 18 shows that the expression of TβRII-dn in CT26 cells suppresses the TGFβ-induced transcription of a PAI-1 promoter-reporter gene construct.

CT26-control cells (CT26 controls) and 5 clones of CT26–TβRII-dn cells (CT26TβRII-dn 1–5) were transfected with a PAI-1 promoter-reporter gene construct (3TP-lux), the cells were stimulated with TGFβ (+TGFβ) or left unstimulated (−TGFβ) and the luciferase activity was measured in cell extracts. As positive controls the cDNA of a constitutively active TGFβ receptor chain 1 (TβRI(T204D; Wrana et al., 1994) as well as the TβRII-dn-cDNA together with 3TP-lux were cotransfected into the cells. This measurement was carried out in cells before injection into the animal (before tumour induction) and after isolation and cultivation of the tumour cells for 3 days (isolated tumour cells) (cf. legend, box at top right). The bars indicate the standardised luciferase activity from extracts with the same protein content (cf. methods).

BIBLIOGRAPHY

Andrejauskas, E., and Moroni, C. (1989), EMBO J. 8, 2575–2581.
Antonelli-Orlidge, A., Saunders, K. B., Smith, S. R., and D'Amore, P. A. (1989), Proc. Natl. Acad. Sci. U.S.A. 86, 4544–4548.
Aznavoorian, S., Murphy, A. N., Stetler, S. W., and Liotta, L. A. (1993), Cancer 71, 1368–1383.
Beham, A. et al., (1992), Virchows Archiv A Pathol. Anat., Vol. 421, 209–215.
Behrens, J., Vakaet, L., Friis, R., Winterhager, E., Van, R. F., Mareel, M. M., and Birchmeier, W. (1993), J. Cell Biol. 120, 757–766.
Birchmeier, W., Weidner, K. M., and Behrens, J. (1993), J. Cell. Sci. (Suppl) 17, 159–164.
Border, A. I., and Ruoslahti, V. (1992), J. Clin. Invest. 90, 1–7.
Bos, J. L. (1989), Cancer Res. 49, 4682–4689.
Brattain, M. G., Strobel-Stevens, J., Find, D., Webb, M., and Sarrif, A. M. (1980), Cancer Res. 40, 2142–2452.

Braunwalder et al. (1996), Annal. Biochem. 238, 159–164
Buchmann, A., Ruggeri, B., Klein, S. A., and Balmain, A. (1991), Cancer Res. 51, 4097–4101.
Castle, V., Varani, J., Fligiel, S., Prochownik, E. V., and Dixit, V. (1991), J. Clin Invest. 87, 1883–1888.
Caulin, C., Scholl, F. G., Frontelo, P., Gamallo, C., and Quintanilla, M. (1995), Cell Growth & Differentiation 6, 1027–1035.
Chomczynski, P., and Sacchi, N. (1987), Anal. Biochem. 162, 156–159.
Clark, G. J., and Der, C. J. (1995), Breast Cancer Research & Treatment 35, 133–144.
De Bortoli, M., Abou-Issa, H., Haley, B. E., and Cho-Chung, Y. S. (1985), Biochem. Biophys. Res. Commun. 127, 699–706.
de Brito, P. A., Silverberg, S. G. and Orenstein, J. M. (1993), Hum. Pathol. Feb. 24 (2), 132–42.
Derynck, R., Jarret, J. A., Chen, E. Y., Eaton, D. H., Bell, J. R., Assoian, R. K., Roberts, A. B., Sporn, M. B., and Goeddel, D. V. (1985), Nature 316, 701–705.
Dvorak, H. F. (1986), N. Engl. J. Med. 315, 1650–1659.
Eaton, S., and Simons, K. (1995), Cell 82, 5–8.
Edwards, D. R., Murphy, G., Reynolds, J. J., Whitham, S. E., Docherty, A. J. P., Angel, P., and Heath, J. K. (1987), EMBO J. 6, 1899–1904.
Fearon, E. R., and Vogelstein, B. (1990), Cell 61, 759–767.
Fakhrai H. et al. (1996), Proc. Nat. Acad. Sci. 93, 2909–2914
Fialka, I., Schwarz, H., Reichmann, E., Busslinger, M., and Beug, H. (1995), J. Cell Biol. 132, 1115–1132.
Frisch, S. M., and Francis, H. (1994), J. Cell Biol. 124, 619–626.
Furth, M. E., Davies, L. J., Fleurdelys, B., and Scolnick, E. M. (1982), J. Virol. 43, 294–304.
Gabbert, H., Wagner, R., Moll, R., and Gerharz, C. D. (1985), Clin. exp. Metastasis 3, 257–279.
Guarino, M., Reale, D., Micoli, G. and Forloni, B. (1993), Histopathology, May 22(5), 493–8.
Guldberg, G. (1923), Scand. 4, 276–284.
Hand, P., Thor, A., Wunderlich, D., Maurano, R., Caruso, A., and Schlom, J. (1984), Proc. Natl. Acad. Sci. U.S.A. 81, 5227–5231.
Hartmann, G., Weidner, K. M., Schwarz, H., and Birchmeier, W. (1994), J. Biol. Chem. 269, 21936–21939.
Hayman, M. J., Meyer, S., Martin, F., Steinlein, P., and Beug, H. (1993), Cell 74, 157–169.
Heatly, M. et al., (1993), J. Clin. Pathol. 46, 441–445
Heider, K.-H. et al. (1995), Eur. J. Cancer, 31A, 2385–2391
Heider, K.-H. et al., 1996, Virchows Archiv 428, 267–273
Hoosein, N. M., McKnight, M. K., Levine, A. E., Mulder, K. M., Childress, K. E., Brattain, D. E., and Brattain, M. G. (1989), Exp. Cell Res. 181, 442–453.
Jenkins, D. C., Stables, J. N., Wilkinson, J., Topley, P., Holmes, L. S., Linstead, D. J., and Rapson, E. B. (1993), Br. J. Cancer 68, 856–861.
Kemler, R. (1993), Trends Genet 9:317–321.
Kern, F. G., Cheville, A. L., and Liu, Y. L. (1990), Semin Cancer Biol 1, 317–328.
Keski-Oja, J., Loef, E. B., Lyons, R. M., Coffey, R. J. J., and Moses, H. L. (1987), J. Cell. Biochem. 33, 95–107.
Kim, S. J., Jeang, K. T., Glick, A. B., Sporn, M. B., and Roberts, A. B. (1989), J. Biol. Chem. 264, 7041–7045.
Kohl, N. E., Mosser, S. D., deSolms, S. J., Giuliani, E. A. et al., (1993), Science 260, 1934–1937.
Kohl, N. E., Wilson, F. R., Mosser, S. D., Giuliani, E. et al., (1994), Proc Natl Acad Sci USA 91, 9141–9145
Kohl, N. E., Omer, C. A., Conner, M. W., Anthony, N. J. et al., (1995), Nature Med 1, 792–797.
Kraus, M. H., Yuasa, Y., and Aaronson, S. A. (1984),Proc. Natl. Acad. Sci. U.S.A. 81, 5384–5388.
Laiho, M., Saksela, O., and Keski-Oja, J. (1987), J. Biol. Chem. 262, 17467–17474.
Land, H., Parada, L. F., and Weinberg, R. A. (1983), Nature 304, 596–602.
LeJeune, S., Leek, R., Horak, E., Plowman, G., Greenall, M., and Harris, A. L. (1993), Cancer Res. 53, 3597–3602.
Leonard, M. W., Lim, K. C., and Engel, J. D. (1993), Development 119, 519–531.
Lin H. Y.; Wang X. F.; Ng-Eaton E.; Weinberg R. A.; Lodish H. F. (1992) Cell 68(4), 775–785, erratum in Cell (1992) 70(6), 1068.
Liotta, L. A., Steeg, P. S., and Stetler-Stevenson, W. G. (1991), Cell 64, 327–336.
Liotta, L. A., and Stetler-Stevenson, W. G. (1991), Cancer Res. 51, 5054–5059.
Macauley, A., and Pawson, T. (1988), J. Virol. 62, 4712–4721.
Maniatis, T., Fritsch, E. F., and Sambrook, J. (1982), Molecular cloning. Cold Spring Harbor Laboratory, Cold Spring Harbor, N.Y.
Mareel, M., Kint, J., and Meyvisch, C. (1979), Virchows Arch. (B) 30, 95–111.
Mareel, M. M. (1983), Cancer Metastasis Rev. 2, 201–218.
Mareel, M. M. (1980), Int. Rev. exp. Pathology 22, 65–129.
Mareel, M. M., Behrens, J., Birchmeier, W., De Bruyne, G. K., Vleminckx, K., Hoodgewus, A., Fiers, W. C., and Van Roy, F. M. (1991), Int. J. Cancer 47, 922–928.
Matsui et al., (1992), Hum. Pathol. Vol. 23, 1289–97.
Miettinen, P. J., Ebner, R., Lopez, A. R., and Derynck, R. (1994), J. Cell Biol. 127, 2021–2036.
Monia, B. P. et al. (1996), Proc. Nat. Acad. Sci. 93, 15481–15484.
Morgenstern, J., P. and Land, H. (1990), Nuc. Acid. Res. 18(12), 3587–3596.
Murthy, U., Anzano, M. A., and Creig, R. G. (1989), Int. J. Cancer 44, 110–115.
Nishihara, K. and Tsuneyoshi, M. (1993), Hum. Pathol. Dec. 24(12), 1298–305.
Oft, M., Bohm, S., Wilczynski, S. P., and Iftner, T. (1993), Int. J. Cancer 53, 924–931.
Parker, T. G., Packer, S. E., and Schneider, M. D. (1990), J Clin Invest 85, 507–514.
Payne, A., Olson, E. N., Hsiau, P., Roberts, R., Perryman, M. B., and Schneider, M. D. (1987), Proc. Natl. Acad. Sci. USA 84, 8956–8960.
Pear, W.,S., Nolan, G., P., Scott, M., L., Baltimore, D. (1993) Proc. Natl. Acad. Sci. USA 90(18) 8392–8396.
Powell, S. M., Petersen, G. M., Krush, A. J., Booker, S., Jen, J., Giardiello, F. M., Hamilton, S. R., Vogelstein, B., and Kinzler, K. W. (1993), N. Engl. J. Med. 329, 1982–1987.
Quilliam, L. A., Kato, K., Rabun, K. M., Hisaka, M. M., Huff, S. Y., Campbell-Burk, S., and Der, C. J. (1994), Mol Cell Biol 14, 1113–1121.
Redmond, S. M., Reichmann, E., Mueller, R. G., Friis, R. R., Groner, B., and Hynes, N. E. (1988), Oncogene 2, 259–265.
Reichmann, E. (1994), Semin Cancer Biol 5, 157–165.
Reichmann, E., Ball, R., Groner, B., and Friis, R. R. (1989), J. Cell Biol. 108, 1127–1138.
Reichmann, E., Schwarz, H., Deiner, E. M., Leitner, I., Eilers, M., Berger, J., Busslinger, M., and Beug, H. (1992), Cell 71, 1103–1116.
Remington's Pharmaceutical Sciences, 1980, Mack Publ. Co., Easton, PA, Osol (ed.).
Roberts, A. B., and Sporn, M. B. (1992), Cancer Surv. 14, 205–220.

Roberts, A. B., Sporn, M. B., Assoian, R. K., Smith, J. M., Roche, N. S., Wakefield, L. M., Heine, U. I., Liotta, L. A., Falanga, V., Kehrl, J. H., and Fauci, A. S. (1986), Proc. Natl. Acad. Sci. U.S.A. 83, 4167–4171.

Sandford, K. K., Dunn, T. B., Westfall, B. B., Covalesky, B. B., Covalesky, A. B., Dupree, L. T., and Earle, W. R. (1961), J. Nat. Cancer Inst. 26, 1139–1193.

Sato, Y., Tsuboi, R., Lyons, R., Moses, H., and Rifkin, D. B. (1990), J. Cell Biol. 111, 757–763.

Schoenenberger, C. A., Zuk, A., Zinkl, G. M., Kendall, D., and Matlin, K. S. (1994), J. Cell Sci. 107, 527–541.

Schultz-Cherry, S., Ribeiro, S., Gentry, L., and Murphy-Ullrich, J. E. (1994), J Biol Chem 269, 26775–26782.

Schwarz, H. (1994), Immunolabelling of ultrathin resin sections for immunofluorescence and electron microscopy. In Electron microscopy 1994 ICEM, B. Jouffrey and C. Colliex, eds. (Paris: Les editions de physique, Les Ulis, France), pp. 255–256.

Schwarz, H., Mueller-Schmidt, A., and Hoffmann, W. (1993), Cell Tissue Res. 273, 417–425.

Seliger, B., Höhne, A., Knuth, A., Bernhard, H., Ehring, B., Tampé, R., and Huber, C. (.1996), Clin. Canc. Res. 2, 1427–1433.

Slamon, D., J., de Kernion, J. B., Verma, I. M., and Cline, M. J. (1984), Science 224, 256–262.

Sonnenberg, A., Daams, H., Calafat, J., and Hilgers, J. (1986), Cancer Res. 46, 5913–5922.

Soriano, J. V., Pepper, M. S., Nakamura, T., Orci, L., and Montesano, R. (1995), J. Cell Sci. 108, 413–430.

Stacey, D. W., Feig, L. A., and Gibbs, J. B. (1991), Mol. Cell. Biol. 11, 4053–4064.

Stoler, A. B., Stenback, F., and Balmain, A. (1993), J. Cell. Biol. 122, 1103–1117.

Strange, R., Li, F., Friis, R. R., Reichmann, E., Haenni, B., and Burri, P. H. (1991), Cell. Growth Differ. 2, 549–559.

Thompson, A. M., Kerr, D. J., and Steel, C. M. (1991), Br. J. Cancer 63, 609–614.

Thompson, T. C., Truong, L. D., Timme, T. L., Kadmon, D., McCune, B. K., Flanders, K. C., Scardino, P. T., and Park, S. H. (1992), J Cell Biochem Suppl, 54–61.

Thompson, T. C., Truong, L. D., Timme, T. L., Kadmon, D., McCune, B. K., Flanders, K. C., Scardino, P. T., and Park, S. H. (1993), Cancer (Suppl.) 71, 1165–1171.

Thorburn, A., Thorburn, J., Chen, S. Y., Powers, S., Shubeita, H. E., Feramisco, J. R., and Chien, K. R. (1993), J. Biol. Chem. 268, 2244–2249.

Vogelstein, B., and Kinzler, K. W. (1993), Trends Genet. 9, 138–141.

Wargotz, E. S. and Norris, H. J. (1989), Cancer October 64(7), 1490–9.

Wrana, J., L., Attisano, L., Carcamo, J., Zentella, A., Doody, J., Laiho, M., Wang, X-F.,and Massagué, J. (1992) Cell, 71, 1003–1014.

Wrana, J., L., Attisano, L., Wieser, R., Ventura, F., and Massagué, J. (1994), Nature 370, 341–347.

Welch, D. R., Fabra, A., and Nakajima, M. (1990), Proc. Natl. Acad. Sci. U.S.A.87, 7678–7682.

Whitman, M., and Melton, D. A. (1992), Nature 357, 252–254.

Wong, S. Y., Purdie, A. T., and Han, P. (1992), Am. J Pathol. 140, 1473–1482.

Wright, J. H., McDonnell, S., Portella, G., Bowden, G. T., Balmain, A., and Matrisian, L. M. (1994), Mol. Carcinog. 10, 207–215.

Zambruno, G., Marchisio, P. C., Marconi, A., Vaschieri, C., Melchiori, A., Giannetti, A., and De Luca, M. (1995), J. Cell Biol. 129, 853–865.

What is claimed is:

1. A process for screening a test substance to identify the presence therein of a pharmacologically active substance, useful for the treatment of epithelial, invasive tumour disease, comprising:

contacting a mammalian cell with said test substance, and determining whether the signal transduction pathway initiated by TGFβ in said mammalian cell is inhibited, wherein said pharmacologically active substance is detected by the inhibition of said signal transduction pathway and said pharmacologically active substance is not TGFβ, anti-TGFβ antibody or antisense TGFβ RNA.

2. The process according to claim 1, wherein said pharmacologically active substance is an anti-tumour agent, wherein said anti-tumour agent inhibits the growth of epithelial invasive tumour disease cells.

3. The process according to claim 2, wherein said epithelial invasive tumour disease cells are characterized by a reversible transition of the cells from an epithelial, non-invasive state into an invasive state.

4. The process according to claim 1, wherein said mammalian cell is transformed with (a) a plasmid containing a reporter gene which is under the control of the regulatory sequence of a cell protein regulated by TGFβ; or (b) a plasmid containing a DNA sequence coding for a functional mammalian TGFβ receptor.

5. The process according to claim 4, wherein said mammalian cell is grown in culture.

6. The process according to claim 4, wherein said mammalian cell is a human cell.

7. The process according to claim 4, wherein said cell is transformed with a plasmid containing a DNA sequence coding for TGFβ receptor type II.

8. The process according to claim 4, wherein said reporter gene is under the control of the regulatory sequence of the plasminogen activator inhibitor.

9. The process according to claim 4, wherein said inhibition is determined by measuring the modulation, by said test substance, of the autophosphorylation of (a) the TGFβ receptor type II or (b) the cytoplasmic domain of said TGFβ receptor type II.

10. The process according to claim 4, wherein said inhibition is determined by measuring the modulation, by said test substance, of the ability of the TGFβ receptor type II to phosphorylate the TGFβ receptor type I or its GS domain.

11. The process according to claim 1, wherein said mammalian cell is a human cell.

12. The process according to claim 1, comprising:

measuring the rate of TGFβ signal transduction in a first mammalian cell comprising a functional TGFβ receptor wherein said receptor is activated by the addition or presence of a selected concentration of TGFβ;

contacting a second mammalian cell comprising said functional TGFβ receptor with said test substance;

activating the functional TGFβ receptor in said second mammalian cell by the addition or presence of said selected concentration of TGFβ;

measuring the rate of TFGβ signal transduction in said second mammalian cell;

wherein the presence of said pharmacologically active substance in said test substance is detected when the measured rate of TGFβ signal transduction in said second mammalian cell is less than the measured rate of TGFβ signal transduction in said first mammalian cell.

13. The process according to claim 12, wherein said first mammalian cell and said second mammalian cell are transformed with
   (a) a plasmid containing a reporter gene which is under the control of the regulatory sequence of a cell protein regulated by TGFβ; or
   (b) a plasmid containing a DNA sequence coding for a functional mammalian TGFβ receptor.

14. A process for screening a test substance to identify the presence therein of a pharmacologically active substance, useful for the treatment of epithelial, invasive tumour disease, comprising:

contacting a test substance with a mammalian cell, wherein said mammalian cell is transformed with
   (a) a plasmid containing a reporter gene which is under the control of the regulatory sequence of a cell protein regulated by TGFβ, or
   (b) a plasmid containing a DNA sequence coding for a functional mammalian TGFβ receptor; and
determining whether the signal transduction pathway initiated by TGFβ in said mammalian cell is inhibited;
wherein said pharmacologically active substance is detected by the inhibition of said signal transduction pathway and said pharmacologically active substance is not TGFβ, anti-TGFβ antibody or antisense TGFβ RNA.

* * * * *